US008476420B2

(12) United States Patent
Showe et al.

(10) Patent No.: US 8,476,420 B2
(45) Date of Patent: Jul. 2, 2013

(54) METHOD FOR DIAGNOSING LUNG CANCERS USING GENE EXPRESSION PROFILES IN PERIPHERAL BLOOD MONONUCLEAR CELLS

(75) Inventors: Michael Showe, Media, PA (US); Louise Showe, Media, PA (US); Malik Yousef, Dabburiya Village (IL); Steven M. Albelda, Bala Cynwyd, PA (US); Anil Vachani, Merion Station, PA (US); Andrei V. Kossenkov, Huntingdon Valley, PA (US)

(73) Assignees: The Wistar Institute of Anatomy and Biology, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 422 days.

(21) Appl. No.: 12/745,991

(22) PCT Filed: Dec. 5, 2008

(86) PCT No.: PCT/US2008/013450
§ 371 (c)(1),
(2), (4) Date: Jun. 3, 2010

(87) PCT Pub. No.: WO2009/075799
PCT Pub. Date: Jun. 18, 2009

(65) Prior Publication Data
US 2010/0255486 A1   Oct. 7, 2010

Related U.S. Application Data

(60) Provisional application No. 61/005,569, filed on Dec. 5, 2007.

(51) Int. Cl.
C12N 15/11    (2006.01)
C12N 15/113   (2010.01)
C12N 15/12    (2006.01)
C07H 21/04    (2006.01)
C12Q 1/68     (2006.01)

(52) U.S. Cl.
USPC ....... 536/24.3; 536/23.1; 536/23.2; 536/23.5; 435/6.14

(58) Field of Classification Search
None
See application file for complete search history.

(56) References Cited

U.S. PATENT DOCUMENTS

| 6,040,138 | A  | 3/2000  | Lockhart et al. |
| 7,081,340 | B2 | 7/2006  | Baker et al. |
| 7,640,114 | B2 | 12/2009 | Showe et al. |
| 2006/0105360 | A1 | 5/2006  | Croce et al. |
| 2006/0134639 | A1 | 6/2006  | Huffel et al. |
| 2006/0199204 | A1 | 9/2006  | Dix et al. |
| 2006/0223127 | A1 | 10/2006 | Yip et al. |
| 2007/0003972 | A1 | 1/2007  | Hanash et al. |
| 2007/0026424 | A1 | 2/2007  | Powell et al. |
| 2007/0053921 | A1 | 3/2007  | Raitano et al. |
| 2007/0099196 | A1 | 5/2007  | Kauppinen et al. |
| 2007/0105114 | A1 | 5/2007  | Li et al. |
| 2007/0105133 | A1 | 5/2007  | Clarke et al. |
| 2007/0299030 | A1 | 12/2007 | Dmitrovsky et al. |
| 2008/0076674 | A1 | 3/2008  | Litman et al. |
| 2008/0182245 | A1 | 7/2008  | Brown et al. |

FOREIGN PATENT DOCUMENTS

| WO | WO 2004/105573  | 12/2004 |
| WO | WO 2007142936   | 12/2007 |
| WO | WO 2008/073923  | 6/2008  |
| WO | WO 2009/075799  | 6/2009  |
| WO | WO 2010/054233  | 5/2010  |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Chung, et al, Sequential molecular genetic changes in lung cancer development, Oncogene, 11(12):2591-2598, (Dec. 21, 1995).
De Andrés, et al, Improved method for mRNA extraction from paraffin-embedded tissues, BioTechniques, 18(1):42, 44, (Jan. 1995).
Hod, Y., A simplified ribonuclease protection assay, BioTechniques, 13(6):852-854, (Dec. 1992).
Talmadge, JE., et al, Immunologic attributes of cytokine mobilized peripheral blood stem cells and recovery following transplantation, Bone Marrow Transplantation, 17(1):101-109, (Jan. 1996).
Benson et al, Genbank, Nucleic Acids Research, 35(Database Issue):D21-25 (Jan. 2007).
International Search Report for PCT/US2008/013450 dated Jan. 28, 2009.
Written Opinion of the International Searching Authority dated Jan. 28, 2009.
International Search Report dated Mar. 5, 2010 issued in International Patent Applicaitn No. PCT/US09/63603.

(Continued)

Primary Examiner — James Martinell
(74) Attorney, Agent, or Firm — Howson & Howson LLP

(57) ABSTRACT

Methods and compositions are provided for diagnosing lung cancer in a mammalian subject by use of three or more selected genes, e.g., a gene expression profile, from the peripheral blood mononuclear cells (PBMC) of the subject which is characteristic of disease, a stage of the disease, or enables prognosis of recurrence of disease. The gene expression profile includes three or more genes of Table I, Table II, Table III, Table IV, Table V, Table VI or Table VII herein. Detection of changes in expression in the selected genes forming the gene expression profile from that of a reference gene expression profile are correlated with non-small cell lung cancer (NSCLC). One composition for use in such diagnosis includes three or more PCR primer-probe sets, wherein each primer-probe set amplifies a different polynucleotide sequence from the gene expression profile. Another composition for similar use contains a plurality of polynucleotides immobilized on a substrate, which probes hybridize to three or more gene expression products from genes in the gene expression profile. Still another composition involves detection of the protein expression products of genes from the gene expression profile.

7 Claims, 6 Drawing Sheets

OTHER PUBLICATIONS

Office Action dated Sep. 18, 2008 issued in U.S. Appl. No. 10/558,252.
Response to Office Action dated Dec. 18, 2008 submitted in U.S. Appl. No. 10/558,252.
Office Action dated Feb. 25, 2009 issued in U.S. Appl. No. 10/558,252.
Response to Office Action dated May 26, 2009 submitted in U.S. Appl. No. 10/558,252.
Office Action dated Jul. 14, 2009 issued in U.S. Appl. No. 10/558,252.
Response to Office Action dated Aug. 10, 2009 submitted in U.S. Appl. No. 10/558,252.
Amos, CI, et al, Genome-wide association scan of tag SNPs identifies a susceptibility locus for lung cancer at 15q25.1, Nature Genetics, 40(5):616-22, May 2008, Epublication: Apr. 2, 2008.
Bach, PB, Computed tomography screening and lung cancer outcomes, JAMA, Journal of the American Medical Association 297 (9):953-961 Mar. 7, 2007.
Belinsky, SA, et al, Promoter hypermethylation of multiple genes in sputum precedes lung cancer incidence in a high-risk cohort, Cancer Research, 66:3338-3344 Mar. 15, 2006.
Benito, M., et al., Adjustment of systematic microarray data biases, Bioinformatics, 20 (1):105-114, Jan. 1, 2004.
Bhattacharjee, A., et al., Classification of human lung carcinomas by mRNA expression profiling reveals distinct adenocarcinoma subclasses, Proceedings of the National Academy of Sciences of the United States, 98(24):13790-13795, Nov. 20, 2001.
Borczuk, A.C., et al., Non-small-cell lung cancer molecular signatures recapitulate lung developmental pathways, The American Journal of Pathology, 163 (5):1949-1960, Nov. 2003.
Brichory FM, et al, An immune response manifested by the common occurrence of annexins I and II autoantibodies and high circulating levels of IL-6 in lung cancer, Proceedings of the National Acadamy of Sciences of the U S A, 98 (17):9824-9829 Aug. 14, 2001.
Bull, TM, et al, Gene Microarray Analysis of Peripheral Blood Cells in Pulmonary Arterial Hypertension, The American Journal of Respiratory Critical Care Medicine, 170(8):911-919, Oct. 2004.
Burczynski, ME, et al., Molecular classification of Crohn's disease and ulcerative colitis patients using transcriptional profiles in peripheral blood mononuclear cells, Journal of Molecular Diagnostics 8(1):51-61, Feb. 2006.
Burczynski, M.E., et al., Clinical pharmacogenomics and transcriptional profiling in early phase oncology clinical trials, Current Molecular Medicine, 5(1):83-102, Feb. 2005.
Chang, H.Y., et al., Diversity, topographic differentiation, and positional memory in human fibroblasts, Proceedings of the National Academy Sciences of the United States of America, 99(20):12877-82, Oct. 1, 2002, Epublication: Sep. 24, 2002.
Critchley-Thorne, R.J., et al., Down-regulation of the interferon signaling pathway in T lymphocytes from patients with metastatic melanoma, PLoS Medicine, 4(5):e176, May 2007.
Deng, MC, et al., Noninvasive discrimination of rejection in cardiac allograft recipients using gene expression profiling, American Journal of Transplantation, 6(1):150-160, Jan. 2006.
Deprimo, S.E., et al., Expression profiling of blood samples from an SU5416 Phase III metastatic colorectal cancer clinical trial: a novel strategy for biomarker identification, BMC Cancer, 3(3):1-12, Feb. 7, 2003, Epublication: Feb. 7, 2003.
Ding and Cantor, A high-throughput gene expression analysis technique using competitive PCR and matrix-assisted laser desorption ionization time-of-flight MS, Proceedings of National Acadamy of Sciences of USA, 100(6):3059-3064, Mar. 18, 2003, Epublication: Mar. 6, 2003.
Eady, J.J., et al., Variation in gene expression profiles of peripheral blood mononuclear cells from healthy volunteers, Physiological Genomics, 22(3):402-411, Aug. 11, 2005, Epublication: Jul. 12, 2005.
Eberle, J., et al, Downregulation of endothelin B receptor in human melanoma cell lines parallel to differentiation genes, Journal of Investigative Dermatology, 112(6):925-9324, Jun. 1999.
Forrest, M.S., et al., Discovery of novel biomarkers by microarray analysis of peripheral blood mononuclear cell gene expression in benzene-exposed workers, Environmental Health Perspectives, 113(6): 801-807, Jun. 2005.
Godfrey, T.E., et al, Quantitative mRNA expression analysis from formalin-fixed, paraffin-embedded tissues using 5' nuclease quantitative reverse transcription-polymerase chain reaction, Journal of Molecular Diagnostics, 2(2):84-91, May 2000.
Golub, Molecular Classification of Cancer: Class Discovery and Class Prediction by Gene Expression Monitoring, Science, 286(5439):531-537, Oct. 15, 1999.
Haiman, C.A., et al., Ethnic and racial differences in the smoking-related risk of lung cancer, The New England Journal of Medicine, 354(4):333-342, Jan. 26, 2006.
Hamalainen, H., et al, Distinct gene expression profiles of human type 1 and type 2 T helper cells, Genome Biology,2(7):Research. 0022, Jun. 2001, Epublication: Jun. 21, 2001.
Henschke, CI, et al, Survival of patients with stage I lung cancer detected on CT screening, The New England Journal of Medicine, 355(17):1763-1771, Oct. 26, 2006.
Hirano, T., et al., Genesis of squamous cell lung carcinoma. Sequential changes of proliferation, DNA ploidy, and p53 expression, American Journal of Pathology, 144(12):296-302, Feb. 1994.
Hirsch, F.R., et al., Early Detection of Lung Cancer: Clinical Perspectives of Recent Advances in Biology and Radiology, Clinical Cancer Research, 7(1):5-22, Jan. 2001.
Ikeda, K, et al, Differential diagnosis of ground-glass opacity nodules: CT number analysis by three-dimensional computerized quantification, Chest, 132(3):984-990, Sep. 2007, Epublication: Jun. 15, 2007.
Jemal et aL, Cancer statistics, 2006, Journal for Clinicians, 56(2):106-130, Mar.-Apr. 2006.
Jett, J.R., Limitations of Screening for Lung Cancer with Low-Dose Spiral Computed Tomography, Clinical Cancer Research, 11(13 Pt 2):4988s-4992s, Jul. 1, 2005.
Karube, Y et al, Reduced expression of Dicer associated with poor prognosis in lung cancer patients, Cancer Science, 96(2):111-115; Feb. 17, 2005.
Kari, L., et al., Classification and prediction of survival in patients with the leukemic phase of cutaneous T cell lymphoma, The Journal of Experimental Medicine, 197(11):1477-1488, Jun. 2. 2003.
Karimi, K., et al., Toll-like receptor-4 mediates cigarette smoke-induced cytokine production by human macrophages, Respiratory Research, 7:66, Apr. 19, 2006.
Khan, J et al., Classification and diagnostic prediction of cancers using gene expression profiling and artificial neural networks, Nature Medicine,7(6):673-679, Jun. 2001.
Kunkel, E.J., and E.C. Butcher, Chemokines and the tissue-specific migration of lymphocytes, Immunity,16(1):1-4, Jan. 2002.
Lampe, J.W., et al., Signatures of environmental exposures using peripheral leukocyte gene expression: tobacco smoke, Cancer Epidemiology, Biomarkers & Prevention, 13(3): 445-453, Mar. 2004.
Liang, Y, et al, Characterization of microRNA expression profiles in normal human tissues, BMC Genomics, 8:166, Jun. 12, 2007.
Machida, EO, et al. Hypermethylation of ASC/TMS1 is a sputum marker for late-stage lung cancer, Cancer Research, 66(12):6210-6218, Jun. 15, 2006.
MacMahon, H., et al., Guidelines for management of small pulmonary nodules detected on CT scans: a statement from the Fleischner Society, Radiology, 237(2):395-400, Nov. 2005.
Marcus et al, Lung Cancer Mortality in the Mayo Lung Project: Impact of Extended Follow-up, Journal of the National Cancer Institute, 92(16):1308-1316, Aug. 16, 2000.
Mukherjee, S., et al., Estimating dataset size requirements for classifying DNA microarray data, Journal of Computational Biology, 10(2):119-142, Apr. 2003.
Mulshine, J.L., Clinical issues in the management of early lung cancer, Clinical Cancer Research, 11(13 Pt 2):4993s-4998s, Jul. 1, 2005.
Nebozhyn, M., et al., Quantitative PCR on 5 genes reliably identifies CTCL patients with 5% to 99% circulating tumor cells with 90% accuracy, Blood, 107(8):3189-3196, Apr. 15, 2006, Epublication: Jan. 10, 2006.

Obata-Onai, A., et al, Comprehensive gene expression analysis of human NK cells and CD8(+) T lymphocytes, International Immunology, 14(10):1085-1098, Oct. 2002.

Oudijk, E.J., et al., Systemic inflammation in COPD visualised by gene profiling in peripheral blood neutrophils, Thorax, 60(7):538-544, Jul. 2005.

Palmisano et al, Predicting lung cancer by detecting aberrant promoter methylation in sputum, Cancer Research, 60(21):5954-5958, Nov. 1, 2000.

Patz EF, Jr.et al, Panel of serum biomarkers for the diagnosis of lung cancer, Journal of Clinical Oncology, 25(35):5578-5583, Dec. 10, 2007.

Raychaudhuri, Basic Microarray analysis: grouping and feature reduction, Trends in Biotechnology, 19(5):189-193, May 2001.

Redente, E.F., et al., Tumor signaling to the bone marrow changes the phenotype of monocytes and pulmonary macrophages during urethane-induced primary lung tumorigenesis in A/J mice, American Journal of Pathology, 170(2):693-708, Feb. 2007.

Russo, A.L., et al., Differential DNA hypermethylation of critical genes mediates the stage-specific tobacco smoke-induced neoplastic progression of lung cancer, Clinical Cancer Research, 11(7):2466-2470, Apr. 1, 2005.

Sharma, P., et al., Early detection of breast cancer based on gene-expression patterns in peripheral blood cells, Breast Cancer Research, 7(5):R634-R644, Jun. 2005.

Sharp, F.R., et al., The future of genomic profiling of neurological diseases using blood, Archives of Neurology, 63(11):1529-1536, Nov. 2006.

Sorlie, T., et al., Gene expression patterns of breast carcinomas distinguish tumor subclasses with clinical implications, Proceedings of the National Academy of Sciences of the U S A, 98(19):10869-10874, Sep. 11, 2001.

Specht et al., Quantitative gene expression analysis in microdissected archival formalin-fixed and paraffin-embedded tumor tissue, The American Journal of Pathology, 158(2):419-429, Feb. 2001.

Spira, A., et al., Effects of cigarette smoke on the human airway epithelial cell transcriptome, Proceedings of the National Academy of Sciences of the United States of America, 101(27):10143-10148, Jul. 6, 2004, Epublication: Jun. 21, 2004.

Talbot, SG, et al., Gene expression profiling allows distinction between primary and metastatic squamous cell carcinomas in the lung, Cancer Research, 65(8):3063-3071, Apr. 15, 2005.

Theodoro, T.R., et al., Heparanase expression in circulating lymphocytes of breast cancer patients depends on the presence of the primary tumor and/or systemic metastasis, Neoplasia, 9(6):504-510, Jun. 2007.

Tibshirani, R., et al., Diagnosis of multiple cancer types by shrunken centroids of gene expression, Proceedings of the National Academy of Sciences in USA, 99(10):6567-6572, May 14, 2002.

Tonon, G., et al., High-resolution genomic profiles of human lung cancer, Proceedings of the National Acadamy of Sciences in USA, 102(27):9625-9630, Jul. 5, 2005, Epublication: Jun. 27, 2005.

Twine, N., et al., Disease-associated expression profiles in peripheral blood mononuclear cells from patients with advanced renal cell carcinoma, Cancer Research, 6:6069-6075, Sep. 2003.

Vachani, A., et al., A 10-gene classifier for distinguishing head and neck squamous cell carcinoma and lung squamous cell carcinoma, Clinical Cancer Research, 13(10):2905-2915, May 15, 2007.

Van Leeuwen, D.M., et al., Cigarette smoke-induced differential gene expression in blood cells from monozygotic twin pairs, Carcinogenesis, 28(3):691-697, Mar. 2007, Epublication: Oct. 19, 2006.

Virok, D., et al., Infection of U937 monocytic cells with Chlamydia pneumoniae induces extensive changes in host cell gene expression, Journal of Infectious Diseases, 188(9):1310-1321, Nov. 2003, Epublication: Oct. 13, 2003.

Whitney, A.R., et al., Individuality and variation in gene expression patterns in human blood, Proceedings of the National Academy of Sciences of the United States of America 100(4):1896-1901, Feb. 18, 2003.

Yanaihara, N. et al, Unique microRNA molecular profiles in lung cancer diagnosis and prognosis, Cancer Cell, 9(3):189-198, Mar. 2006.

Loboda, A., et al., Classification of cancers by gene expression profiles from peripheral blood, Proceedings of the European Conference on Computational Biology, GE-19:383-384, Sep. 2003.

Betel, D, Wilson M, Gabow A, Marks DS, Sander C., Nucleic Acids Research, the microRNA.org resource: targets and expression, 36(Database issue):D149-53, Jan. 2008, Epublished: Dec. 23, 2007.

Eisen, et al, Cluster analysis and display of genome-wide expression patterns, Proceedings of the National Academy of Sciences of the United States of America, 95(25):14863-14868, Dec. 8, 1998.

Guyon, I., et al., Gene Selection for Cancer Classification using Support Vector Machines, Machine Learning, 46(1-3):389-422, Jan. 2002.

Heid, et al., Real time quantitative PCR, Genome Research, 6(10):986 994, Oct. 1996.

Osman, I, et al, Novel blood biomarkers of human urinary bladder cancer, Clinical Cancer Research, 12(11):3374-80, Jun. 1, 2006.

Ramaswamy, et al, Multiclass cancer diagnosis using tumor gene expression signatures, Proceedings of the National Academy of Sciences of the United States of America, 98(26):15149-54, Dec. 2001.

International Preliminary Report on Patentability dated Jun. 8, 2010 issued in PCT/US2008/013450.

Affymetric Human Geneonme U133 Plus 2.0 Array, Gene Expression Omnibus, 1-3, Nov. 7, 2003—cited by EPO in Supplementary Partial EP Search Report.

GeneAnnot for the Gene Symbols HBXAP (a.k.a RSF1), DYRK2, YY1, Cl9orf12 for HG-U95, HG-I133 and HG-I133 Plus 2.0, 1-3, Apr. 21, 2011—cited by EPO in Supplementary Partial EP Search Report.

EP Communication dated Dec. 28, 2010 in corresponding European Appln No. 08859692.9.

Response to EP Communication dated Dec. 28, 2010 in corresponding European Appln No. 08859692.9 dated Mar. 7, 2011.

Extended Partial EP Search Report dated May 23, 2011 in corresponding European Appln No. 08859692.9.

EP Communication dated Jun. 9, 2011 in corresponding European Appln No. 08859692.9.

Response to EP Communication dated Jun. 9, 2011 in corresponding European Appln No. 08859692.9 filed Dec. 19, 2011.

* cited by examiner

METHOD FOR DIAGNOSING LUNG CANCERS USING GENE EXPRESSION PROFILES IN PERIPHERAL BLOOD MONONUCLEAR CELLS

CROSS-REFERENCE TO RELATED APPLICATIONS

This application is a national stage of International Patent Application No. PCT/US2008/013450, filed Dec. 5, 2008, which claims the benefit of the priority of U.S. Provisional Patent Application No. 61/005,569, filed Dec. 5, 2007 (expired), which applications are incorporated herein by reference in their entirety.

STATEMENT REGARDING FEDERALLY SPONSORED RESEARCH OR DEVELOPMENT

This invention was made with government support under Grant No. R01 CA125749 awarded by the National Institutes of Health. The government has certain rights in this invention.

BACKGROUND OF THE INVENTION

Lung cancer is the most common worldwide cause of cancer mortality. In the United States, lung cancer is the second most prevalent cancer in both men and women and will account for more than 174,000 new cases per year and more than 162,000 cancer deaths. In fact, lung cancer accounts for more deaths each year than from breast, prostate and colorectal cancers combined[2].

The high mortality (80-85% in five years), which has shown little or no improvement in the past 30 years, emphasizes the fact that new and effective tools to facilitate early diagnoses prior to metastasis to regional nodes or beyond the lung are needed[6].

High risk populations include smokers, former smokers, and individuals with markers associated with genetic predispositions[91-93]. Because surgical removal of early stage tumors remains the most effective treatment for lung cancer, there has been great interest in screening high-risk patients with low dose spiral CT (LDCT)[12,14,15,94]. This strategy identifies non-calcified pulmonary nodules in approximately 30-70% of high risk individuals but only a small proportion of detected nodules are ultimately diagnosed as lung cancers (0.4 to 2.7%)[16,95,96]. Currently, the only way to differentiate subjects with lung nodules of benign etiology from subjects with malignant nodules is an invasive biopsy, surgery, or prolonged observation with repeated scanning. Even using the best clinical algorithms 20-55% of patients selected to undergo surgical lung biopsy for indeterminate lung nodules, are found to have benign disease[15] and those that do not undergo immediate biopsy or resection require sequential imaging studies. The use of serial CT in this group of patients runs the risk of delaying potential curable therapy, along with the costs of repeat scans, the not-insignificant radiation doses, and the anxiety of the patient.

Ideally, a diagnostic test would be easily accessible, inexpensive, demonstrate high sensitivity and specificity, and result in improved patient outcomes (medically and financially). Efforts are in progress to develop non-invasive diagnostics using sputum, blood or serum and analyzing for products of tumor cells, methylated tumor DNA[7,8], single nucleotide polymorphism (SNPs)[9] expressed messenger RNA[10] or proteins[11]. This broad array of molecular tests with potential utility for early diagnosis of lung cancer has been discussed in the literature. Although each of these approaches has its own merits, none has yet passed the exploratory stage in the effort to detect patients with early stage lung cancer, even in high-risk groups, or patients which have a preliminary diagnosis based on radiological and other clinical factors[12]. A simple blood test, a routine event associated with regular clinical office visits, would be an ideal diagnostic test.

One established method to achieve the goal of genetic diagnosis has been the use of microarray signatures from tumor tissue[20]. This approach has been tested and validated by numerous investigators[89]. An increasing number of studies have shown that peripheral blood mononuclear cells (PBMC) profiles can be used to diagnose and classify systemic diseases, including cancer, and to monitor therapeutic response.[21] The validity of using PBMC profiles in patients with cancer has been previously reported in the use of microarrays to compare PBMC from patients with late stage renal cell carcinoma compared to normal controls[20,42]. A more recent publication[43] describes the development of a 37 gene classifier for detecting early breast cancer from peripheral blood samples with 82% accuracy. Another study identified gene expression profiles in the PBMC of colorectal cancer patients that could be correlated with response to therapy[44]. Some of the present inventors previously suggested[22] that chemokines and cytokines released by malignant cells could impose a tumor specific signature on immune cells of patients with non-hematopoietic cancers. Gene expression profiles have now been generated from PBMC that identify blood signatures associated with a variety of cancers, including metastatic melanoma[23], breast[24], renal[25,26] and bladder cancer[27]. Most of these studies focused on late stage cancers or response to therapy and used younger healthy control groups for comparison.

While the effect of chronic obstruction pulmonary disease (COPD) on PBMC gene expression is relatively unstudied to date, there are some limited reports about the effect of cigarette smoke[33]. Exposure of peripheral blood lymphocytes (PBL) ex vivo to cigarette smoke induced many changes in gene expression[34]. Changes could be detected in the transcriptosome of blood neutrophils in COPD patients versus normals[35]. One study distinguished "between 85 individuals exposed and unexposed to tobacco smoke on the basis of mRNA expression in peripheral leukocytes"[36]. No data is apparently available regarding similar changes in blood that may be present in former-smokers. Gene expression in airway epithelia of smokers, ex-smokers and non-smokers has been compared[37]. Although many clinical manifestations of smoking rapidly returned to normal after smoking cessation, there was a subset of genes whose expression remained altered. Differential gene hypermethylation[38] and dysregulated macrophage cytokine production[33] have also been linked to cigarette smoke. However, to date, there are no reports of gene expression profile or signature useful in the diagnosis of lung cancer.

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. In particular, once a patient is diagnosed with cancer, there is a strong need for methods that allow the physician to predict the expected course of disease, including the likelihood of cancer recurrence, long-term survival of the patient, and the like, and select the most appropriate treatment option accordingly. There also remains a need in the art for a less invasive diagnostic test that could more accurately determine the risk of malignant disease in patients with lung nodules and would reduce unnecessary surgery, biopsies, PET scans, and/or repeated CT scans.

SUMMARY OF THE INVENTION

In one aspect, a composition for diagnosing or evaluating a lung cancer in a mammalian subject includes (a) three or more polynucleotides or oligonucleotides, wherein each polynucleotide or oligonucleotide hybridizes to a different gene, gene fragment, gene transcript or expression product from mammalian peripheral blood mononuclear cells (PBMC), or (b) three or more ligands, wherein each ligand binds to a different gene expression product from mammalian peripheral blood mononuclear cells (PBMC). Each gene, gene fragment, gene transcript or expression product is selected from (i) the genes of Table I; (ii) the genes of Table II; (iii) the genes of Table III; (iv) the genes of Table IV, or (v) a combination of genes from more than one of these Tables.

Thus, in one embodiment, a composition for diagnosing or evaluating lung cancer in a mammalian subject includes three or more PCR primer-probe sets, wherein each primer-probe set amplifies a different polynucleotide or oligonucleotide sequence from a gene expression product of three or more informative genes selected from a gene expression profile in the peripheral blood mononuclear cells (PBMC) of the subject. The gene expression profile includes three or more genes of Table I or Table II or Table III or Table IV or a combination thereof. This composition enables amplification of genes in the gene expression profile and detection of changes in expression in the genes in the subject's gene expression profile from that of a reference gene expression profile. The various reference gene expression profiles are described below. Such changes correlate with a lung cancer, such as a non-small cell lung cancer (NSCLC).

Thus, in another aspect, a composition for diagnosing or evaluating a lung cancer in a mammalian subject is composed of a plurality of polynucleotides or oligonucleotides immobilized on a substrate. The plurality of genomic probes hybridizes to three or more gene expression products of three or more informative genes selected from a gene expression profile in the PBMC of the subject. The gene expression profile includes three or more genes of Table I or Table II or Table III or Table IV or a combination thereof. This composition enables detection of changes in expression in said genes in said gene expression profile from that of a reference gene expression profile, said changes correlated with a diagnosis, prognosis or evaluation of a lung cancer, e.g., NSCLC.

Thus, in another embodiment, a composition or kit for diagnosing or evaluating a lung cancer in a mammalian subject includes a plurality of ligands that bind to three or more gene expression products of three or more informative genes selected from a gene expression profile in the PBMC of the subject. The gene expression profile includes three or more genes of Table I or Table II or Table III or Table IV or a combination thereof. This composition enables detection of changes in expression in said genes in said gene expression profile from that of a reference gene expression profile, said changes correlated with a lung cancer, such as NSCLC.

Thus, in still another embodiment, a composition for diagnosing or evaluating a lung cancer in a mammalian subject includes a plurality of gene expression products of three or more informative genes selected from a gene expression profile in the PBMC of the subject immobilized on a substrate for detection or quantification of antibodies in the PBMC of the subject. The gene expression profile comprises three or more genes of Table I or Table II or Table III or Table VII or a combination thereof. This composition enables detection of changes in expression in the genes in the gene expression profile from that of a reference gene expression profile, said changes correlated with a diagnosis or evaluation of a lung cancer, such as NSCLC.

In another aspect, any of the compositions described above employ polynucleotides, oligonucleotides, or ligands that hybridize, amplify or bind to the genes or products of the informative genes from Table I that include three or more genes selected from the group consisting of IGSF6, HSPA8 (A), LYN, DNCL1, HSPA1A, DPYSL2, HAGK, HSPA8(I), NFKBIA, FGL2, CALM2, CCL5, RPS2, DDIT4 and C1orf63.

In still a further aspect, any of the compositions described above employ polynucleotides, oligonucleotides, or ligands that hybridize, amplify or bind to the genes or products of the informative genes from Table II that include three or more genes selected from the group consisting of ETS1, CCL5, DDIT4, CXCR4, DNCL1, MS4ABA, ATP5B, HSPA8(A), ADM PTPN6, ARHGAP9, S100A8, DPYSL2, HSPA1A, and NFKBIA.

In another aspect, any of the compositions described above employ polynucleotides, oligonucleotides, or ligands that hybridize, amplify or bind to the genes or products of the informative genes from Table III that include three or more genes selected from the group consisting of TSC22D3, CXCR4, DNCL1, RPS3, DDIT4, GAMB, BTG1, HSPA8(I), RPL12, SLA, RUNX3, MGC17330, HSPA1A, IL18RAP and CIRBP.

In another aspect, a method for diagnosing or evaluating a lung cancer in a mammalian subject involves identifying changes in the expression of three or more genes from the peripheral blood mononuclear cells (PBMC) of a subject, said genes selected from (a) the genes of Table I; (b) the genes of Table II; (c) the genes of Table III; or (d) the genes of Table IV; or (v) a combination thereof, and comparing that subject's gene expression levels with the levels of the same genes in a reference or control, wherein changes in expression of said gene expression correlates with a diagnosis or evaluation of a lung cancer. In one embodiment, the lung cancer is a NSCLC.

In another aspect, a method for diagnosing or evaluating a lung cancer in a mammalian subject involves identifying a gene expression profile in the PBMC of a subject, the gene expression profile comprising three or more gene expression products of three or more informative genes having increased or decreased expression in lung cancer. The three or more informative genes are selected from the genes of Table I or Table II or Table III or Table IV or a combination thereof. The subject's gene expression profile is compared with a reference gene expression profile from a variety of sources described below. Changes in expression of the informative genes correlate with a diagnosis or evaluation of a lung cancer, e.g., NSCLC.

In still a further aspect, a method of predicting the likelihood of recurrence or evaluating the progression, regression or other response of a lung cancer to therapy in a mammalian subject is provided. This method includes identifying a gene expression profile in the PBMC of a subject after solid tumor resection or chemotherapy. The gene expression profile comprises three or more gene expression products of three or more informative genes from the above noted tables, particularly Table III. The subject's post-surgical or post-therapeutic gene expression profile is then compared with said subject's pre-surgical or pre-therapeutic gene expression profile. Changes in expression of the informative genes correlate with a decreased likelihood of recurrence, a recurrence of cancer, a regression of cancer or some other therapy-related response.

In another aspect of this method, a gene expression profile indicative of low recurrence post-surgery or post-therapy is identifiable in the PBMC of a subject that has a background of smoking and/or has COPD.

In another aspect, a novel method for selecting significant genes in comparative gene expression studies is provided. This novel method, i.e., SVM-RCE, combines K-means and Support Vector Machines (SVMs) to identify and score (rank) those gene clusters for the purpose of classification by (i) initially using K-means to group genes into clusters; and (ii) using recursive cluster elimination (RCE) to iteratively remove those clusters of genes that contribute the least to the classification performance.

In yet a further aspect, a composition for diagnosing or evaluating a lung cancer in a mammalian subject is provided. This composition includes (a) three or more polynucleotides or oligonucleotides, wherein each polynucleotide or oligonucleotide hybridizes to a different gene, gene fragment, gene transcript or expression product from mammalian peripheral blood mononuclear cells (PBMC), or (b) three or more ligands, wherein each ligand binds to a different gene expression product from mammalian peripheral blood mononuclear cells (PBMC). The gene, gene fragment, gene transcript or expression product is selected from among (i) the genes of Table V; (ii) the genes of Table VI; (iii) the genes of Table VII, or (iv) genes from a combination of these Tables.

In one embodiment, the composition includes polynucleotides or oligonucleotides that hybridize to, or ligands that bind the expression products of, the first 29 genes of Table V (hereinafter referred to as "the 29 gene classifier") or a subset thereof. This embodiment is particularly useful for diagnosis of a lung cancer, such as a NSCLC, and distinguishing between subjects with cancer and subjects with non-cancer lung disease.

In another embodiment, the composition includes polynucleotides or oligonucleotides that hybridize to, or ligands that bind the expression products of, the first four genes of Table VI, or a subset thereof. This embodiment is particularly useful for determining the prognosis of post-surgical lung cancer subjects.

In another embodiment, the composition includes polynucleotides or oligonucleotides that hybridize to, or ligands that bind the expression products of, the 24 genes of Table VII, or a subset thereof. This embodiment is particularly useful for diagnosis of a lung cancer and distinguishing between subjects with cancer and subjects with benign lung nodules.

In still another aspect, a method for diagnosing or evaluating lung cancer in a mammalian subject comprising identifying changes in the expression of three or more genes from the peripheral blood mononuclear cells (PBMC) of said subject. The genes are selected from (a) the genes of Table V; (b) the genes of Table VI; (c) the genes of Table VII, and (d) the genes from a combination of these tables. The subject's gene expression levels of the selected genes or gene signature are compared with the levels of the same genes or profile in a reference or control. Changes in expression of these genes between the subject and the control correlates with a diagnosis or prognosis of a lung cancer, or an evaluation of recurrence or other response to therapy.

Other aspects and advantages of these compositions and methods are described further in the following detailed description of the preferred embodiments thereof.

DETAILED DESCRIPTION OF THE INVENTION

Figure 1:
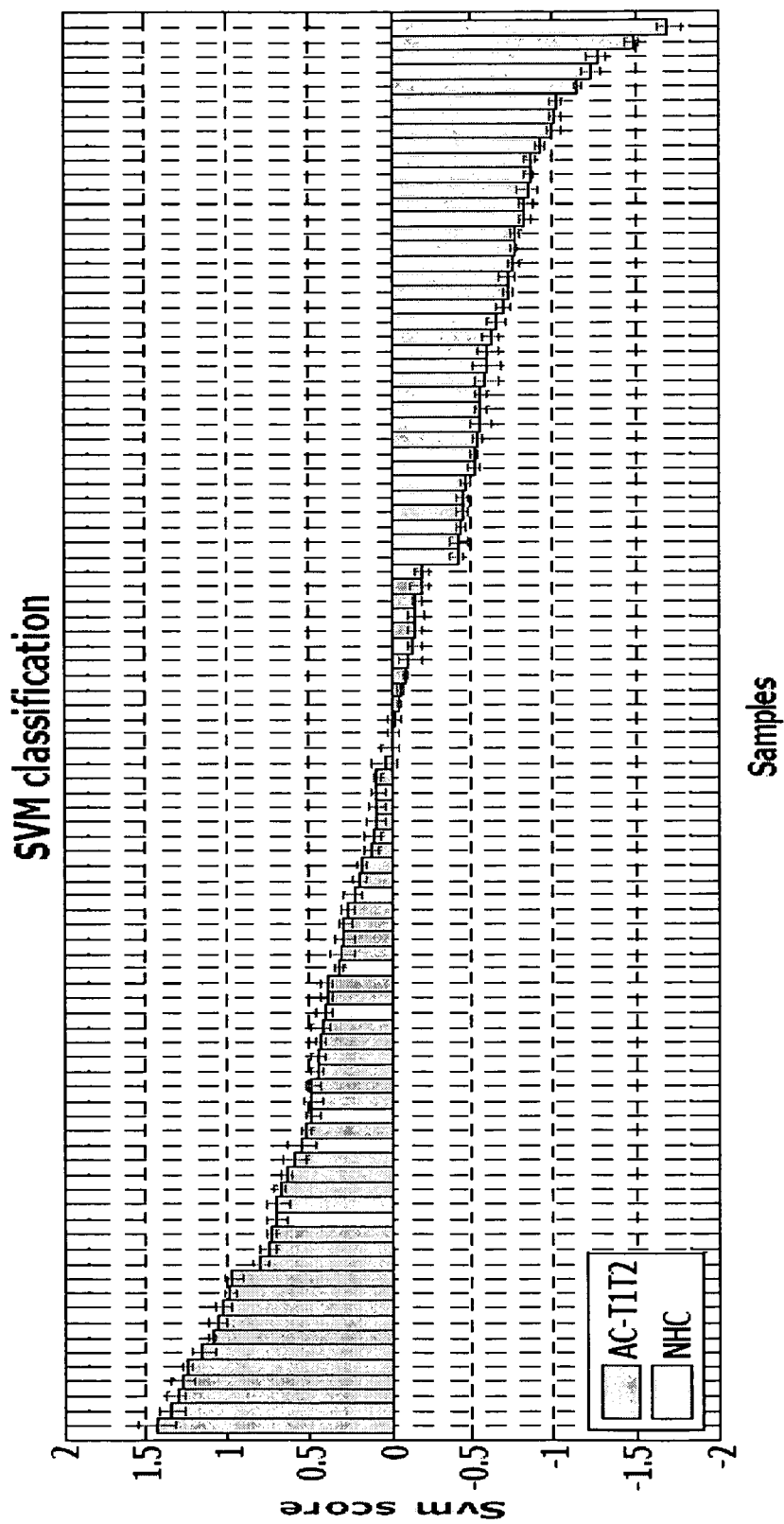
FIG. 1 is a bar graph showing the SVM classification scores for 44 early stage adenocarcinoma (AC T1T2) patient samples (dark bars) and 52 non-healthy controls (NHC, indicated by lighter bars) using 15 genes selected by SVM-RFE. See the 15 genes of Table IV, column labeled "AC/NHC". SVM-scores are calculated as an average across all SVM-scores assigned to a sample when it is in a test set during cross-validation. Each column represents one sample. Error bars represent the standard deviation of the classifications over the 100 resamplings. The ROC curve for the 15 gene classifier performance produced an AUC=area under curve of 0.92 (curve not shown).

The methods and compositions described herein apply gene expression technology to blood screening for the detection, diagnosis, and monitoring of response to treatment of lung cancer. The compositions and methods described herein permit the diagnosis of a disease or its stage generally, and lung cancers particularly, by determining a characteristic RNA expression profile of the genes of the peripheral blood mononuclear cells (PBMC) or peripheral blood lymphocytes (PBL) of a mammalian, preferably human, subject. The profile is established by comparing the profiles of numerous subjects of the same class (e.g., patients with a certain type and stage of lung cancer, or a mixture of types and stages) with numerous subjects of a class from which these individuals must be distinguished in order to provide a useful diagnosis.

These methods of lung cancer screening employ compositions suitable for conducting a simple and cost-effective and non-invasive blood test using gene expression profiling that could alert the patient and physician to obtain further studies, such as a chest radiograph or CT scan, in much the same way that the prostate specific antigen is used to help diagnose and follow the progress of prostate cancer. The gene expression profiles described herein provide the basis for a variety of classifications related to this diagnostic problem. The application of these profiles provides overlapping and confirmatory diagnoses of the type of lung disease, beginning with the initial test for malignant vs. non-malignant disease.

I. Definitions

"Patient" or "subject" as used herein means a mammalian animal, including a human, a veterinary or farm animal, a domestic animal or pet, and animals normally used for clinical research. In one embodiment, the subject of these methods and compositions is a human.

"Control" or "Control subject" as used herein refers to the source of the reference gene expression profiles as well as the particular panel of control subjects identified in the examples below. For example, the control subject in one embodiment can be controls with lung cancer, such as a subject who is a current or former smoker with malignant disease, a subject with a solid lung tumor prior to surgery for removal of same; a subject with a solid lung tumor following surgical removal of said tumor; a subject with a solid lung tumor prior to therapy for same; and a subject with a solid lung tumor during or following therapy for same. In other embodiments, the controls for purposes of the compositions and methods described herein include any of the following classes of reference human subject with no lung cancer. Such non-healthy controls (NHC) include the classes of smoker with non-malignant disease, a former smoker with non-malignant disease (including patients with lung nodules), a non-smoker who has chronic obstructive pulmonary disease (COPD), and a former smoker with COPD. In still other embodiments, the control subject is a healthy non-smoker with no disease or a healthy smoker with no disease. In yet other embodiments, the control or reference is the same subject in which the genes or gene profile was assessed prior to surgery, or at another earlier timepoint to enable assessment of surgical or treatment efficacy or prognosis or progression of disease. Selection of the particular class of controls depends upon the use to which the diagnostic/monitoring methods and compositions are to be put by the physician.

In the examples below, the selected control group, non-healthy controls, is specifically chosen to match as closely as possible the patients with malignant disease. The match includes both smoking status and smoking-related diseases such as COPD. All subjects of both classes were either current or former smokers when they presented with symptoms of disease. The most informative genes identified below can distinguish smokers with malignant disease from smokers with non-malignant disease. These informative genes do not include those previously found to distinguish smokers from non-smokers, for example CYP1B1, HML2, CCR2, NRG1.[36]

"Sample" as used herein means any biological fluid or tissue that contains immune cells and/or cancer cells. The most suitable sample for use in this invention includes peripheral blood, more specifically peripheral blood mononuclear cells. Other useful biological samples include, without limitation, whole blood, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a patient having cancer. Such samples may further be diluted with saline, buffer or a physiologically acceptable diluent. Alternatively, such samples are concentrated by conventional means.

"Immune cells" as used herein means B-lymphocytes, T-lymphocytes, NK cells, macrophages, mast cells, monocytes and dendritic cells.

As used herein, the term "cancer" refers to or describe the physiological condition in mammals that is typically characterized by unregulated cell growth. More specifically, as used herein, the term "cancer" means any lung cancer. In one embodiment, the lung cancer is non-small cell lung cancer (NSCLC). In a more specific embodiment, the lung cancer is lung adenocarcinoma (AC or LAC). In another more specific embodiment, the lung cancer is lung squamous cell carcinoma (SCC or LSCC). In another embodiment, the lung cancer is a stage I or stage II NSCLC. In still another embodiment, the lung cancer is a mixture of early and late stages and types of NSCLC.

The term "tumor," as used herein, refers to all neoplastic cell growth and proliferation, whether malignant or benign, and all pre-cancerous and cancerous cells and tissues.

By "diagnosis" or "evaluation" refers to a diagnosis of a lung cancer, a diagnosis of a stage of lung cancer, a diagnosis of a type or classification of a lung cancer, a diagnosis or detection of a recurrence of a lung cancer, a diagnosis or detection of a regression of a lung cancer, a prognosis of a lung cancer, or an evaluation of the response of a lung cancer to a surgical or non-surgical therapy.

By "change in expression" is meant an upregulation of one or more selected genes in comparison to the reference or control; a downregulation of one or more selected genes in comparison to the reference or control; or a combination of certain upregulated genes and down regulated genes.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

By "non-tumor genes" as used herein is meant genes which are normally expressed in other cells, preferably immune cells, of a healthy mammal, and which are not specifically products of tumor cells.

By "informative genes" as used herein is meant those genes the expression of which changes (either in an up-regulated or down-regulated manner) characteristically in the presence of lung cancer. A statistically significant number of such informative genes thus form suitable gene expression profiles for use in the methods and compositions.

The term "statistically significant number of genes" in the context of this invention differs depending on the degree of change in gene expression observed. The degree of change in gene expression varies with the type of cancer and with the size or spread of the cancer or solid tumor. The degree of change also varies with the immune response of the individual and is subject to variation with each individual. For example, in one embodiment of this invention, a large change, e.g., 2-3 fold increase or decrease in a small number of genes, e.g., in from 3 to 8 characteristic genes, is statistically significant. This is particularly true for cancers without solid tumors. In another embodiment, a smaller relative change in about 10, 20, 24, 29, or 30 or more genes is statistically significant. This is particularly true for cancers with solid tumors. Still alternatively, if a single gene is profiled as up-regulated or expressed significantly in cells which normally do not express the gene, such up-regulation of a single gene may alone be statistically significant. Conversely, if a single gene is profiled as down-regulated or not expressed significantly in cells which normally do express the gene, such down-regulation of a single gene may alone be statistically significant. As an example, a single gene, which is expressed about the same in all members of a population of patients, is 4-fold down regulated in only 1% of individuals without cancer. Four such independently regulated genes in one individual, all 4 fold down-regulated, would occur by chance only one time in 100 million. Therefore those 4 genes are a statistically significant number of genes for that cancer. Alternatively, if normal variance is higher, e.g., one healthy person in 10 has the gene 4-fold down-regulated, then a larger panel of genes is required to detect variance for a particular cancer.

Thus, the methods and compositions described herein contemplate examination of the expression profile of a "statistically significant number of genes" ranging from 1 to about 100 genes in a single profile. In one embodiment, the gene profile is formed by a statistically significant number of 1 or more genes. In another embodiment, the gene profile is formed by a statistically significant number of 3 or more genes. In still another embodiment, the gene profile is formed by 4 or more genes. In still another embodiment, the gene profile is formed by at least 5 to 15 or more genes. In still another embodiment, the gene profile is formed by 24 or 29 or more genes. In still other embodiments, the gene profiles examined as part of these methods, particularly in cases in which the cancers are characterized by solid tumors, contain, as statistically significant numbers of genes, from 5, 10, 15, 20, 30, 40, 50, 60, 70, 80, or 90 or more genes in a panel, and any numbers therebetween.

Tables I to VII below refer to collections of known genes. Tables I, II and III include the top 100 genes in each classification identified by the inventors as capable of forming a gene expression profile for three distinct classifications of disease. Table I identifies the top 100 genes that can be used in a gene expression profile to identify the presence of a lung cancer, e.g., any NSCLC. Table II identifies the top 100 genes that can be used in a gene expression profile to distinguish the occurrence of a lung cancer, and in one embodiment are useful to distinguish AC from any other NSCLC. Table III identifies the top 100 genes that can be used in a gene expression profile to identify the changes consistent with post-surgical improvement of and/or the maintenance of post-surgical improvement of a lung cancer, such as an NSCLC. This latter collection of genes is also anticipated to be useful in tracking improvement during or following therapeutic treatment of a lung cancer, such as an NSCLC. Table IV shows the top 15 gene classifiers for a gene expression profile to identify the presence of a lung cancer, such as NSCLC (i.e., taken from Table I), to identify an AC (i.e., taken from Table II), and to identify the post-surgical status of a subject (i.e., taken from Table III).

Table V identifies an additional 136 genes useful in forming gene profiles for use in diagnosing patients with a lung cancer, such as an NSCLC, from a control, particularly non-healthy controls. The top ranked 29 genes in this table are referenced as "the 29 gene classifier" in Examples 14-18 below. Table VI identifies another set of 50 genes useful in a gene expression profile to identify the changes consistent with post-surgical improvement of and/or the maintenance of post-surgical improvement of a lung cancer. Similarly these genes are useful as a gene signature to monitor cancer progression or regression in a patient treated non-surgically for a lung cancer. Table VII identifies a set of 24 genes useful in discriminating between a subject having a lung cancer, e.g., NSCLC, and subjects having benign (non-malignant) lung nodules.

The genes identified in Tables I through VII are publicly available. One skilled in the art may readily reproduce the compositions and methods described herein by use of the sequences of the genes, all of which are publicly available from conventional sources, such as GenBank.

The term "microarray" refers to an ordered arrangement of hybridizable array elements, preferably polynucleotide or oligonucleotide probes, on a substrate.

The term "polynucleotide," when used in singular or plural form, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as lung cancer, relative to its expression in a control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects, non-health controls and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is a statistically significant ($p<0.05$) difference in gene expression between the subject and control samples.

The term "over-expression" with regard to an RNA transcript is used to refer to the level of the transcript determined by normalization to the level of reference mRNAs, which might be all measured transcripts in the specimen or a particular reference set of mRNAs.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "prognosis" is used herein to refer to the prediction of the likelihood of cancer-attributable death or progression, including recurrence, metastatic spread, and drug resistance, of a neoplastic disease, such as lung cancer. The term "prediction" is used herein to refer to the likelihood that a patient will respond either favorably or unfavorably to a drug or set of drugs, and also the extent of those responses, or that a patient will survive, following surgical removal of the primary tumor and/or chemotherapy for a certain period of time without cancer recurrence. The predictive methods of the present invention can be used clinically to make treatment decisions by choosing the most appropriate treatment modalities for any particular patient. The predictive methods described herein are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 1 year, more preferably for at least 3 years, most preferably for at least 7 years following surgery or other treatment.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher is the relative temperature which can be used. As a result, it follows that higher relative temperatures would tend to make the reaction conditions more stringent, while lower temperatures less so. Various published texts[69,77] provide additional details and explanation of stringency of hybridization reactions.

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

"Moderately stringent conditions" may be identified conventionally[70], and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like, by use of manufacturer's instructions (see, e.g., Illumina system instructions).

In the context of the compositions and methods described herein, reference to "three or more," "at least five," etc. of the genes listed in any particular gene set (e.g., Table I to VII) means any one or any and all combinations of the genes listed. For example, suitable gene expression profiles include profiles containing any number between at least 3 through 100 genes from those Tables. In one embodiment, gene profiles formed by genes selected from a table are preferably used in rank order, e.g., genes ranked in the top of the list demonstrated more significant discriminatory results in the tests, and thus may be more significant in a profile than lower ranked genes. However, in other embodiments the genes forming a useful gene profile do not have to be in rank order and may be any gene from the respective table.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product[71]. In theory the term "intron" refers to any segment of DNA that is transcribed but removed from within the transcript by splicing together the exons on either side of it. Operationally, exon sequences occur in the mRNA sequence of a gene. Operationally, intron sequences are the intervening sequences within the genomic DNA of a gene, bracketed by exon sequences and having GT and AG splice consensus sequences at their 5' and 3' boundaries.

As used herein, "labels" or "reporter molecules" are chemical or biochemical moieties useful for labeling a nucleic acid (including a single nucleotide), polynucleotide, oligonucleotide, or protein ligand, e.g., amino acid or antibody. "Labels" and "reporter molecules" include fluorescent agents, chemiluminescent agents, chromogenic agents, quenching agents, radionucleotides, enzymes, substrates, cofactors, inhibitors, magnetic particles, and other moieties known in the art. "Labels" or "reporter molecules" are capable of generating a measurable signal and may be covalently or noncovalently joined to an oligonucleotide or nucleotide (e.g., a non-natural nucleotide) or ligand.

Unless defined otherwise in this specification, technical and scientific terms used herein have the same meaning as commonly understood by one of ordinary skill in the art to which this invention belongs and by reference to published texts[72,73], which provide one skilled in the art with a general guide to many of the terms used in the present application.

II. The Gene Expression Profiles

The inventors identified diagnostic gene expression profiles in the peripheral blood lymphocytes of lung cancer patients. The inventors have discovered that the gene expression profiles of the PBMCs of lung cancer patients differ significantly from those seen in appropriately matched (i.e. by age, sex, smoking history) controls. For example, changes in the gene expression products of the genes of these profiles can be observed and detected by the methods of this invention in the normal circulating PBMC of patients with early stage solid lung tumors.

The gene expression profiles described herein provide new diagnostic markers for the early detection of lung cancer and could prevent patients from undergoing unnecessary procedures (i.e. if a small lung nodule is discovered) or potential be used to screen high risk patients. Since the risks are very low, the benefit to risk ratio is very high. The methods and compositions described herein may also be useful in other populations, i.e., to screen certain high-risk lung cancer populations, such as asbestos exposed smokers. In yet another embodiment, the methods and compositions described herein may be used in conjunction with clinical risk factors to help physicians make more accurate decisions about how to manage patients with lung nodules. Another advantage of this invention is that diagnosis may occur early since diagnosis is not dependent upon detecting circulating tumor cells which are present in only vanishing small numbers in early stage lung cancers.

Because the effects of smoking and/or chronic obstructive pulmonary diseases on the PBMC profile have the potential to obscure the results of diagnostic methods based on gene profiles, as detailed below, the effects of current smoking, former smoking, and COPD are specifically addressed in the compositions and methods herein by use of appropriate populations of matched controls. In one embodiment, the appropriate control class for the comparative studies is at risk smokers and ex-smokers with non-malignant lung disease so that the smoking related histories of both patient subject and control subjects are very similar. The data presented in the examples below clearly indicate that the inventors detect a cancer signature in the presence of a background of smoking and/or COPD.

In one embodiment, a novel gene expression profile or signature can identify and distinguish patients with early stage (T1/T2-primarily Stage I/II) non small cell cancers of the lung (NSCLC) from the appropriate control group of smokers and ex-smokers at high risk for developing lung cancer matched by age, gender, and race. See for example the genes identified in Table I which may form a suitable gene expression profile and those of Table IV, column "ALL/NHC". In another embodiment, a novel gene expression profile or signature can identify patients with early stage (T1/T2) AC tumors (primarily Stage I and II), in comparison to the closely related NHC control. See Table II and Table IV, column "AC/NHC". The validity of these methods and gene expression profiles is supported in experimental data measuring the lung cancer "score" in patients before and after surgery. In another embodiment, the gene collections in Table III and Table IV, column PRE/POST provide a discrete number of genes that form a suitable profile. These patient/control populations were distinguished by generating a discriminant score based on differences in gene expression profiles as exemplified below. In one embodiment, a 15 gene classifier, i.e., a set of genes that form a gene expression profile, can distinguish between early stage AC tumor vs. non healthy control profiles with an accuracy of 85%. That gene expression profile is identified in Table IV, column "ALL/NHC" below. Additionally, the inventors have identified a gene expression profile classifier that distinguishes both AC and LSCC patients from NHC with an accuracy of 83% also requiring 15 genes for the profile. That gene expression profile is identified in Table IV, col. "AC/NHC" below. A similar gene expression profile to distinguish pre-surgery from post-surgery patients is also found in Table IV, col. "PRE/POST" below. The data shown in the examples clearly indicates that there is a shared early stage cancer-specific signature that is separate from the patterns that discriminate cancer types (AC vs. LSCC) and that discriminate cancer stage (early vs. late).

More recent data described in Examples 14-18 below provide a new 29 gene expression signature to diagnose subjects with lung cancer from healthy or non-healthy controls (Table V, genes ranked 1-29), as well as additional genes from that table that can form other signatures. The relatively small panel of 29 genes can distinguish early stage NSCLC (Stage 1A-1B) from a highly similar control group with good accuracy. Additionally, a set of 4 genes from the 50 gene selection of Table VI is useful to distinguish and track post-surgical improvement. Further, a new 24 gene expression profile to discriminate between lung cancer subjects and subjects with benign lung nodules is provided in Table VII. The data shown in these examples demonstrates lung cancer gene signatures useful in both diagnosis and evaluating the progress of treatment.

As described in detail in the examples below, by comparing gene expression in PBMC from a large group of NSCLC patients to a comparable group of patients with non-malignant lung diseases, a tumor induced signature was detected, in smokers and non-smokers, which can be distinguished from effects of smoking induced non-malignant lung disease. As demonstrated in the examples below, diagnostic signatures are identified in PBMC that distinguish patients with early stage NSCLC from at-risk controls with non-malignant lung disease balanced for smoking, age and gender as well as incidence of COPD. There were also 14 NSCLC patients in these examples that had no prior history of smoking. Lung cancer in individuals who have never smoked has been shown to have several important differences from tobacco associated lung tumors and some molecular changes that occur have been suggested to be unique to non-smokers[28,29]. 11 of the 14 never-smokers were correctly classified as cancer by the 29 gene classifier, suggesting that the effect on PBMC gene expression of lung cancers in smokers and non-smokers is similar, at least with respect to the PBMC gene signatures.

Fourteen genes associated with nicotinate and nicotinamide metabolism were statistically significantly lower in NSCLC patients when compared to all the controls or compared only to controls with benign lung nodules suggesting these pathways may be suppressed in NSCLC patients. Differences detected in PBMC between patients before and after surgical resection were numerous. However, 2 of the 4 most informative genes that distinguish the pre-versus post surgery samples have mitochondrial functions. Mitochondrial genes in general are higher pre-surgery suggesting the increased requirements for energy described for tumors are also reflected in the PBMC when the tumor is present. Highly significant pathways that were higher in pre-surgery samples were associated with NK cell function, and ceramide signaling, [NK: 29 genes ($p<2.08\times10^{-8}$), ceramide: 17 genes ($p<8.83\times10^{-5}$)]. The most significantly down regulated pathways included apoptosis and death receptor genes (Apoptosis: 15 genes ($p<1.74\times10^{-2}$), Death receptor: 13 genes ($p<1.37\times10^{-3}$) patterns also characteristic of tumors[31,32]. The observed reduction of the NSCLC cancer signature and the highly significant common differences shown by patients post-surgery supports the conclusion that the signatures described herein are tumor induced.

Specific interactions between the tumor, lymphocytes and tumor-released factors contribute to the changes seen in PBMC gene expression and these effects are enhanced in tumor progression, as evidenced by the increased accuracy of our gene panel in classifying late stage NSCLC.

The validity of these signatures was established on samples collected at different locations by different groups and in a cohort of patients with undiagnosed lung nodules. The gene expression profiles identified below by use of ILLUMINA arrays provide global diagnostic signatures to identify patients with lung cancers of various cell types, and provide cell type specific diagnostic signatures. Further the profiles take into account race, gender and smoking history. The inventors have also tested samples from a group of patients before and after lung cancer surgery, thus eliminating person-to person-variability in assessing the tumor effect. The lung cancer signature consistently diminishes or disappears after removal of the tumor. This result, as discussed in the examples below, strongly supports the identification of a PBMC signature for early stage lung cancer. This data (see Example 12) shows a consistent decrease in each patient's lung cancer score after surgical removal of the cancer as compared to that score before surgery.

The lung cancer signatures or gene expression profiles identified herein and through use of the gene collections of Tables I-VII may be further optimized to reduce the numbers of gene expression products necessary and increase accuracy of diagnosis.

While not wishing to be bound by theory, the inventors' use of gene expression studies of PBMC in disease is based on the proposition that circulating PBMC (peripheral blood mononuclear cells-primarily monocytes and lymphocytes) are affected by localized processes that involve inflammation and/or tumors. This can occur by at least two mechanisms. First, the cells can directly interact in the tissues of the inflammation or tumor. Clearly, a key function of lymphocytes is to "patrol" the tissues of the body, temporary arrest in abnormal areas, egress from tissues, interact with lymph nodal tissues, become activated, and then re-enter the circulation (with some reentering the tissues). This close interaction clearly alters their phenotype. A second, and probably equally important process is the response of the PBMC to circulating factors released by cells in the inflammatory response or tumors. Many such factors have been described, including colony stimulating factors (such as G-CSF, GM-CSF), cytokines (i.e., TNF, IL-2, IL-3, IL4, and IL-, IL-7, IL-15, etc), chemokines (MCP-1, SDF-1), growth factors (such as Flt-3 ligand, VEGF), immunosuppressive factors (such as IL-10, COX-1, TGF-β), etc. These factors affect immature cells in the bone marrow which are then released into the circulation, as well as cells already in the circulating compartment. This later mechanism likely affects both the phenotype of released cells and the type of cells released (i.e. early after infection there is an influx of immature neutrophils in the circulation).

Although inflammatory lesions and tumors have some similarities, there are many differences, a very important one being the well known ability of tumors to suppress immune responses. The cancer signatures established by the gene expression profiles described herein can be differentiated from an inflammatory signature.

III. Gene Expression Profiling Methods

Methods of gene expression profiling that were used in generating the profiles useful in the compositions and methods described herein or in performing the diagnostic steps using the compositions described herein are known and well summarized in U.S. Pat. No. 7,081,340. Such methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization[74]; RNAse protection assays[75]; and PCR-based methods, such as RT-PCR[76]. Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

A. Polymerase Chain Reaction (PCR) Techniques

The most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure. The first step is the isolation of mRNA from a target sample (e.g., typically total RNA isolated from human PBMC in this case). mRNA can be extracted, for example, from frozen or archived paraffin-embedded and fixed (e.g. formalin-fixed) tissue samples.

General methods for mRNA extraction are well known in the art, such standard textbooks of molecular biology[77]. Methods for RNA extraction from paraffin embedded tissues are known[78,79]. In particular, RNA isolation can be performed using purification kit, buffer set and protease from commercial manufacturers, according to the manufacturer's instructions. Exemplary commercial products include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test). Conventional techniques such as cesium chloride density gradient centrifugation may also be employed.

The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. See, e.g., manufacturer's instructions accompanying the product GENEAMP RNA PCR kit (Perkin Elmer, Calif., USA). The derived cDNA can then be used as a template in the subsequent RT-PCR reaction.

The PCR step generally uses a thermostable DNA-dependent DNA polymerase, such as the Taq DNA polymerase, which has a 5'-3' nuclease activity but lacks a 3'-5' proofreading endonuclease activity. Thus, TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment. In a preferred embodiment, the 5' nuclease procedure is run on a real-time quantitative PCR device such as the ABI PRISM 7900® Sequence Detection System®. The system amplifies samples in a 96-well format on a thermocycler. During amplification, laser-induced fluorescent signal is collected in real-time through fiber optic cables for all 96 wells, and detected at the CCD. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

Real time PCR is comparable both with quantitative competitive PCR, where internal competitor for each target sequence is used for normalization, and with quantitative comparative PCR using a normalization gene contained within the sample, or a housekeeping gene for RT-PCR.[110]

In another PCR method, i.e., the MassARRAY-based gene expression profiling method (Sequenom, Inc., San Diego, Calif.), following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derived PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated[82].

Still other embodiments of PCR-based techniques which are known to the art and may be used for gene expression profiling include, e.g., differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) in a rapid assay for gene expression; and high coverage expression profiling (HiCEP) analysis.

As described in more detail in the examples, below, the gene expression profiles for lung cancer classifications were collected as follows. RNA expression profiles are obtained by purification of PBMC from the blood of subjects by centrifugation using a CPT tube, a Ficoll gradient or equivalent density separation to remove red cells and granulocytes and subsequent extraction of the RNA using TRIZOL tri-reagent, RNALATER reagent or a similar reagent to obtain RNA of high integrity. The amount of individual messenger RNA species was determined using microarrays and/or Quantitative polymerase chain reaction.

After analysis of the RNA concentration, RNA repair and/or amplification steps the RNA is reverse transcribed using gene specific promoters followed by RT-PCR. Finally, the data are analyzed to identify the characteristic gene expression pattern identified in the PBMC sample examined. The expression profiles characteristics of the disease to be diagnosed were compared and analyzed pairwise with an SVM algorithm (SVM-RCE)[1] (described in Examples 4 and 5) and with an alternative methodology described in Example 14 below. These methods can also be demonstrated using the a similar machine-learning algorithm, such as SVM with Recursive Feature Elimination (SVM-RFE) or other classification algorithm such as Penalized Discriminant Analysis (PDA) (see International Patent Application Publication No WO 2004/105573, published Dec. 9, 2004) to obtain a mathematical function whose coefficients act on the input RNA gene express values and output a "SCORE" whose value determines the class of the individual and the confidence of the prediction. Having determined this function by analysis of numerous subjects known to be of the classes whose members are to be subsequently distinguished, it is used to classify subjects for their disease states.

In performing assays and methods of this invention, these same techniques are used, the patient's profile compared with the appropriate reference profile, and diagnosis or treatment recommendation selected based on this information.

B. Microarrays

Differential gene expression can also be identified, or confirmed using the microarray technique. Thus, the expression profile of lung cancer-associated genes can be measured in either fresh or paraffin-embedded tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR for the purposes of the methods and compositions herein, the source of mRNA is total RNA isolated from PBMC of controls and patient subjects.

In one embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels. Microarray analysis can be performed by commercially available equipment, following manufacturer's protocols.

Other useful methods summarized by U.S. Pat. No. 7,081,340, and incorporated by reference herein include Serial Analysis of Gene Expression (SAGE) and Massively Parallel Signature Sequencing (MPSS).

C. Immunohistochemistry

Immunohistochemistry methods are also suitable for detecting the expression levels of the gene expression products of the informative genes described for use in the methods and compositions herein. Antibodies or antisera, preferably polyclonal antisera, and most preferably monoclonal antibodies, or other protein-binding ligands specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Protocols and kits for immunohistochemical analyses are well known in the art and are commercially available.

D. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. by mass spectrometry or N-terminal sequencing, and (3) analysis of the data using bioinformatics. Proteomics methods are valuable supplements to other methods of gene expression profiling, and can be used, alone or in combination with other methods, to detect the gene expression products of the gene profiles described herein.

IV. Compositions Of The Invention

The methods for diagnosing lung cancer utilizing defined gene expression profiles permits the development of simplified diagnostic tools for diagnosing lung cancer, e.g., NSCLC or diagnosing a specific stage (early, stage I, stage II or late) of lung cancer, diagnosing a specific type of lung cancer (e.g., AC vs. LSCC) or monitoring the effect of therapeutic or surgical intervention for determination of further treatment or evaluation of the likelihood of recurrence of the cancer.

Thus, a composition for diagnosing non-small cell lung cancer in a mammalian subject as described herein can be a kit or a reagent. For example, one embodiment of a composition includes a substrate upon which said polynucleotides or oligonucleotides or ligands are immobilized. In another embodiment, the composition is a kit containing the relevant three or more polynucleotides or oligonucleotides or ligands, optional detectable labels for same, immobilization substrates, optional substrates for enzymatic labels, as well as other laboratory items. In still another embodiment, at least one polynucleotide or oligonucleotide or ligand is associated with a detectable label.

Such a composition contains in one embodiment three or more polynucleotides or oligonucleotides, wherein each polynucleotide or oligonucleotide hybridizes to a different gene, gene fragment, gene transcript or expression product from mammalian peripheral blood mononuclear cells (PBMC), wherein said gene, gene fragment, gene transcript or expression product is selected from (i) the genes of Table I; (ii) the genes of Table II; (iii) the genes of Table III; and (iv) the genes of Table IV. In another embodiment, such a composition contains three or more polynucleotides or oligonucleotides, wherein each polynucleotide or oligonucleotide hybridizes to a different gene, gene fragment, gene transcript or expression product from mammalian peripheral blood mononuclear cells (PBMC), wherein said gene, gene fragment, gene transcript or expression product is selected from (i) the genes of Table V; (ii) the genes of Table VI; or (iii) the genes of Table VII.

In another embodiment, such a composition contains three or more ligands, wherein each ligand binds to a different gene expression product from mammalian peripheral blood mononuclear cells (PBMC), wherein the gene expression product is the product of a gene selected from (i) the genes of Table I; (ii) the genes of Table II; (iii) the genes of Table III; and (iv) the genes of Table IV. In still another embodiment, such a composition contains three or more ligands, wherein each ligand binds to a different gene expression product from mammalian peripheral blood mononuclear cells (PBMC), wherein the gene expression product is the product of a gene selected from (i) the genes of Table V; (ii) the genes of Table VI; or (iii) the genes of Table VII.

In one embodiment, a composition for diagnosing lung cancer in a mammalian subject includes three or more PCR primer-probe sets. Each primer-probe set amplifies a different polynucleotide sequence from a gene expression product of three or more informative genes found in the peripheral blood mononuclear cells (PBMC) of the subject. These informative genes are selected to form a gene expression profile or signature which is distinguishable between a subject having lung cancer and a selected reference control. Changes in expression in the genes in the gene expression profile from that of a reference gene expression profile are correlated with a lung cancer, such as non-small cell lung cancer (NSCLC).

In one embodiment of this composition, the informative genes are selected from among the genes identified in Table I below. Table I contains the approximately top 100 genes identified by the inventors as representative of a genomic signature indicative of the presence of any NSCLC lung cancer. This collection of genes is those for which the gene product expression is altered (i.e., increased or decreased) versus the same gene product expression in the PBMC of a reference control. In one embodiment, polynucleotide or oligonucleotides, such as PCR primers and probes, are generated to three or more informative genes from Table I for use in the composition. An example of such a composition contains primers and probes to a targeted portion of the first three genes in that Table. In another embodiment, PCR primers and probes are generated to at least six informative genes from Table I for use in the composition. An example of such a composition contains primers and probes to a targeted portion of the first six genes in that Table. In still another embodiment, PCR primers and probes are generated to at least fifteen informative genes from Table I for use in the composition. An example of such a composition contains primers and probes to a targeted portion of the first fifteen genes in that Table. Still other embodiments employ primers and probes to a targeted portion of other combinations of the genes in the Tables. The selected genes from the Table need not be in rank order; rather any combination that clearly shows a difference in expression between the reference control to the diseased patient is useful in such a composition.

In one specific embodiment, the informative genes from Table I comprise three or more genes selected from the group consisting of IGSF6, HSPA8(A), LYN, DNCL1, HSPA1A, DPYSL2, HAGK, HSPA8(I), NFKBIA, FGL2, CALM2, CCL5, RPS2, DDIT4 and C1orf63.

In another embodiment of this composition, the informative genes are selected from among the genes identified in Table II below. Table II contains the approximately top 100 genes identified by the inventors as representative of a genomic signature indicative of the presence of a specific NSCLC, i.e., lung adenocarcinoma. This collection of genes is those for which the gene product expression is altered (i.e., increased or decreased) versus the same gene product expression in the PBMC of a reference control. In one embodiment, PCR primers and probes are generated to three or more informative genes from Table II for use in the composition. An example of such a composition contains primers and probes to a targeted portion of the first three genes in Table II. In another embodiment, PCR primers and probes are generated to at least six informative genes from Table II for use in the composition. An example of such a composition contains primers and probes to a targeted portion of the first six genes in Table II. In still another embodiment, PCR primers and probes are generated to at least fifteen informative genes from Table II for use in the composition. An example of such a composition contains primers and probes to a targeted portion of the first fifteen genes in that Table II. Still other embodiments employ primers and probes to a targeted portion of other combinations of the genes in Table II. The selected genes from Table II need not be in rank order; rather any combination that clearly shows a difference in expression between the reference control to the diseased patient is useful in such a composition.

In one specific embodiment, the informative genes from Table II comprise three or more genes selected from the group consisting of ETS1, CCL5, DDIT4, CXCR4, DNCL1, MS4ABA, ATP5B, HSPA8(A), ADM PTPN6, ARHGAP9, S100A8, DPYSL2, HSPA1A, and NFKBIA.

In another embodiment of this composition, the informative genes are selected from among the genes identified in Table III. Table III contains the top 100 genes identified by the inventors as representative of a genomic signature indicative of the effect of surgical resection of the tumor of a patient with an NSCLC. This collection of genes is those for which the gene product expression is altered (i.e., increased or decreased) versus the same gene product expression in the PBMC of a patient before and after surgery. In one embodiment, PCR primers and probes are generated to three or more informative genes from Table III for use in the composition. An example of such a composition contains primers and probes to a targeted portion of the first three genes in Table III. In another embodiment, PCR primers and probes are generated to at least six informative genes from Table III for use in the composition. An example of such a composition contains primers and probes to a targeted portion of the first six genes in Table III. In still another embodiment, PCR primers and probes are generated to at least fifteen informative genes from Table III for use in the composition. An example of such a composition contains primers and probes to a targeted portion of the first fifteen genes in that Table III. Still other embodiments employ primers and probes to a targeted portion of other combinations of the genes in Table III. The selected genes from Table III need not be in rank order; rather any combination that clearly shows a difference in expression between pre-surgery NSCLC patient compared with post-surgery NSCLC patient is useful in such a composition.

In another embodiment of this composition, the informative genes are selected from among the genes identified in Table IV. Table IV contains embodiments of 15 genes useful as representative genomic signatures or profiles for three diagnostic uses, i.e., to distinguish between NSCLC and all controls, to distinguish between NSCLC in general and adenocarcinoma and to distinguish between and thus track progression of disease in pre and post-surgical subjects. In one embodiment, PCR primers and probes are generated to all 15 informative genes from Table IV, col. 1 for use in a diagnostic composition. In another embodiment, PCR primers and probes are generated to 15 informative genes from Table IV, col. 2 for use in a diagnostic composition. In still another embodiment, PCR primers and probes are generated to fifteen informative genes from Table IV, col. 3 for use in a diagnostic composition. Still other embodiments employ primers and probes to a targeted portion of other combinations of the genes in Table IV. The selected genes from Table IV need not be in rank order; rather any combination that clearly shows a difference between test subject and the compared groups is useful in such a composition.

In another embodiment of this composition, the informative genes are selected from among the genes identified in Table V. Table V contains embodiments of 136 genes useful as representative genomic signatures or profiles to distinguish between NSCLC and all controls, primarily non-healthy controls. In one embodiment, PCR primers and probes are generated to the top ranked 29 informative genes from Table V, thereby forming the 29 gene classifier of the examples below for use in a diagnostic composition. In still another embodiment, PCR primers and probes are generated to any desired number of informative genes from Table V for use in a diagnostic composition. The selected genes from Table V need not be in rank order; rather any combination that clearly shows a difference between test subject and the compared groups is useful in such a composition.

In another embodiment of this composition, the informative genes are selected from among the genes identified in Table VI. Table VI contains embodiments of 50 genes useful as representative genomic signatures or profiles to distinguish between presurgical and postsurgical subjects. In one embodiment, PCR primers and probes are generated to the top ranked 2 informative genes, e.g., CYP2R1 and MYO5B, from Table VI for use in a diagnostic composition. In still another embodiment, PCR primers and probes are generated to the top four gene, e.g., CYP2R1, MYO5B, DGUOK and DYNLL1, from Table VI for use in a diagnostic composition. In a further composition, oligonucleotides or polynucleotides, such as PCR primers and probes, that hybridize or amplify any desired number of informative genes from Table VI are useful in a diagnostic composition. The selected genes from Table VI need not be in rank order; rather any combination that clearly shows a difference between test subject and the compared groups is useful in such a composition.

In another embodiment of this composition, the informative genes are selected from among the genes identified in Table VII. Table VII contains embodiments of 24 genes useful as representative genomic signatures or profiles to distinguish between NSCLC subjects and subjects with benign lung nodules. In one embodiment, oligonucleotides or polynucleotides, such as PCR primers and probes, are generated to all 24 informative genes from Table VII for use in a diagnostic composition. In still another embodiment, PCR primers and probes are generated to any small number of genes from Table VII for use in a diagnostic composition. The selected genes from Table VII need not be in rank order; rather any combination that clearly shows a difference between test subject and the compared groups is useful in such a composition.

In one embodiment of the compositions described above, the reference control is a non-healthy control (NHC) as described above. In other embodiments, the reference control may be any class of controls as described above in "Definitions". A composition containing polynucleotides or oligonucleotides that hybridize to the members of the selected gene expression profile prepared from a selection of genes listed in these tables is desirable not only for diagnosis, but for monitoring the effects of surgical or non-surgical therapeutic treatment to determine if the positive effects of resection/chemotherapy are maintained for a long period after initial treatment. These profiles also permit a determination of recurrence or the likelihood of recurrence of a lung cancer, e.g., NSCLC, if the results demonstrate a return to the pre-surgery/pre-chemotherapy profiles. It is further likely that these compositions may also be employed for use in monitoring the efficacy of non-surgical therapies for lung cancer.

The compositions based on the genes selected from Tables I through VII described herein, optionally associated with detectable labels, can be presented in the format of a microfluidics card, a chip or chamber, or a kit adapted for use with the PCR, RT-PCR or Q PCR techniques described above. In one aspect, such a format is a diagnostic assay using TAQ-MAN® Quantitative PCR low density arrays. Preliminary results suggest the number of genes required is compatible with these platforms. When a sample of PBMC from a selected patent subject is contacted with the primers and probes in the composition, PCR amplification of targeted informative genes in the gene expression profile from the patient permits detection of changes in expression in the genes in the gene expression profile from that of a reference gene expression profile. Significant changes in the gene expression of the informative genes in the patient's PBMC from that of the reference gene expression profile correlate with a diagnosis of lung cancer when using compositions directed to the genes of Table I or V, or of lung adenocarcinoma when using compositions directed to the genes of Table II. Similarly, when a sample of PBMC from a selected post-surgical patent subject is contacted with the primers and probes in the composition, PCR amplification of targeted informative genes selected from those of Table III or VI in the gene expression profile from the patient permits detection of changes in expression in the genes in the gene expression profile from that of a reference gene expression profile. In this circumstance a preferred reference profile is that obtained from the same patient (or a similar patient) prior to surgery. Significant changes in the gene expression of the informative genes in the patient's PBMC from that of the reference gene expression profile correlate with a positive effect of surgery, and/or maintenance of the positive effect.

Tables I through VII and the identifying information on the genes listed therein are described below.

TABLE I

| GENE NAME | Symbol | Score | Rank |
|---|---|---|---|
| TSC22 domain family, member 3 (TSC22D3), transcript variant 2, mRNA. (A) | TSC22D3 | 0.9522 | 1 |
| chemokine (C—X—C motif) receptor 4 (CXCR4), transcript variant 1, mRNA. (A) | CXCR4 | 0.9444 | 2 |
| dynein, cytoplasmic, light polypeptide 1 (DNCL1), mRNA. (S) | DNCL1 | 0.8668 | 3 |
| ribosomal protein S3 (RPS3), mRNA. (S) | RPS3 | 0.8556 | 4 |
| DNA-damage-inducible transcript 4 (DDIT4), mRNA. (S) | DDIT4 | 0.8502 | 5 |
| granzyme B (granzyme 2, cytotoxic T-lymphocyte-associated serine esterase 1) (GZMB), mRNA. (S) | GZMB | 0.8148 | 6 |
| B-cell translocation gene 1, anti-proliferative (BTG1), mRNA. (S) | BTG1 | 0.8 | 7 |
| heat shock 70 kDa protein 8 (HSPA8), transcript variant 1, mRNA. (I) | HSPA8 | 0.793 | 8 |
| ribosomal protein L12 (RPL12), mRNA. (S) | RPL12 | 0.7564 | 9 |
| Src-like-adaptor (SLA), mRNA. (S) | SLA | 0.7322 | 10 |
| runt-related transcription factor 3 (RUNX3), transcript variant 2, mRNA. (I) | RUNX3 | 0.7306 | 11 |
| HGFL gene (MGC17330), mRNA. (S) | MGC17330 | 0.6982 | 12 |
| heat shock 70 kDa protein 1A (HSPA1A), mRNA. (S) | HSPA1A | 0.684 | 13 |
| interleukin 18 receptor accessory protein (IL18RAP), mRNA. (S) | IL18RAP | 0.6728 | 14 |
| cold inducible RNA binding protein (CIRBP), mRNA. (S) | CIRBP | 0.67 | 15 |
| adrenomedullin (ADM), mRNA. (S) | ADM | 0.662 | 16 |
| CCAAT/enhancer binding protein (C/EBP), beta (CEBPB), mRNA. (S) | CEBPB | 0.654 | 17 |
| PREDICTED: similar to heterogeneous nuclear ribonucleoprotein A1 (LOC645385), mRNA. (S) | LOC645385 | 0.654 | 18 |
| CCAAT/enhancer binding protein (C/EBP), delta (CEBPD), mRNA. (S) | CEBPD | 0.6416 | 19 |

TABLE I-continued

| GENE NAME | Symbol | Score | Rank |
|---|---|---|---|
| Kruppel-like factor 9 (KLF9), mRNA. (S) | KLF9 | 0.6392 | 20 |
| PREDICTED: hypothetical protein LOC440345, transcript variant 6 (LOC440345), mRNA. (I) | LOC440345 | 0.6358 | 21 |
| inhibitor of DNA binding 2, dominant negative helix-loop-helix protein (ID2), mRNA. (S) | ID2 | 0.617 | 22 |
| killer cell Ig-like receptor, two domains, long cytoplasmic tail, 3 (KIR2DL3), transcript variant 2, mRNA(A) | KIR2DL3 | 0.6126 | 23 |
| arachidonate 5-lipoxygenase-activating protein (ALOX5AP), mRNA. (S) | ALOX5AP | 0.6106 | 24 |
| immunoglobulin superfamily, member 6 (IGSF6), mRNA. (S) | IGSF6 | 0.6068 | 25 |
| heat shock 70 kDa protein 8 (HSPA8), transcript variant 2, mRNA. (A) | HSPA8 | 0.6032 | 27 |
| Tubulin, alpha, ubiquitous (K-ALPHA-1), mRNA. (S) | K-ALPHA-1 | 0.6002 | 28 |
| protein kinase C, delta (PRKCD), transcript variant 2, mRNA. (A) | PRKCD | 0.5992 | 29 |
| PR domain containing 1, with ZNF domain (PRDM1), transcript variant 1, mRNA. (A) | PRDM1 | 0.594 | 30 |
| CD55 antigen, decay accelerating factor for complement (Cromer blood group) (CD55), mRNA. (S) | CD55 | 0.5722 | 31 |
| cystatin F (leukocystatin) (CST7), mRNA. (S) | CST7 | 0.5698 | 32 |
| myeloid-associated differentiation marker (MYADM), transcript variant 4, mRNA. (A) | MYADM | 0.568 | 33 |
| major histocompatibility complex, class I, F (HLA-F), mRNA. (S) | HLA-F | 0.568 | 34 |
| SH2 domain protein 2A (SH2D2A), mRNA. (S) | SH2D2A | 0.5656 | 35 |
| potassium channel tetramerisation domain containing 12 (KCTD12), mRNA. (S) | KCTD12 | 0.5638 | 36 |
| Ras-GTPase-activating protein SH3-domain-binding protein (G3BP), transcript variant 1, mRNA. (A) | G3BP | 0.5636 | 37 |
| fibrinogen-like 2 (FGL2), mRNA. (S) | FGL2 | 0.5552 | 38 |
| CCAAT/enhancer binding protein (C/EBP), alpha (CEBPA), mRNA. (S) | CEBPA | 0.5368 | 39 |
| DnaJ (Hsp40) homolog, subfamily A, member 1 (DNAJA1), mRNA. (S) | DNAJA1 | 0.5306 | 40 |
| capping protein (actin filament) muscle Z-line, alpha 2 (CAPZA2), mRNA. (S) | CAPZA2 | 0.5244 | 41 |
| general transcription factor IIIA (GTF3A), mRNA. (S) | GTF3A | 0.523 | 42 |
| IBR domain containing 2 (IBRDC2), mRNA. (S) | IBRDC2 | 0.5228 | 43 |
| interferon stimulated exonuclease gene 20 kDa (ISG20), mRNA. (S) | ISG20 | 0.5208 | 44 |
| PREDICTED: similar to ribosomal protein L13a, transcript variant 4 (LOC649564), mRNA. (A) | LOC649564 | 0.5134 | 45 |
| G protein-coupled receptor 171 (GPR171), mRNA. (S) | GPR171 | 0.5124 | 46 |
| killer cell immunoglobulin-like receptor, two domains, long cytoplasmic tail, 4 (KIR2DL4), mRNA. (S) | KIR2DL4 | 0.5044 | 47 |
| sin3-associated polypeptide, 30 kDa (SAP30), mRNA. (S) | SAP30 | 0.4972 | 48 |
| PREDICTED: meteorin, glial cell differentiation regulator-like (METRNL), mRNA. (I) | METRNL | 0.4936 | 49 |
| chloride intracellular channel 3 (CLIC3), mRNA. (S) | CLIC3 | 0.4926 | 50 |
| eukaryotic translation initiation factor 3, subunit 12 (EIF3S12), mRNA. (S) | EIF3S12 | 0.4912 | 51 |
| insulin receptor substrate 2 (IRS2), mRNA. (S) | IRS2 | 0.4824 | 52 |
| hepatitis A virus cellular receptor 2 (HAVCR2), mRNA. (S) | HAVCR2 | 0.4758 | 53 |
| HD domain containing 2 (HDDC2), mRNA. (S) | HDDC2 | 0.4754 | 54 |
| nuclear RNA export factor 1 (NXF1), mRNA. (S) | NXF1 | 0.468 | 55 |
| perforin 1 (pore forming protein) (PRF1), mRNA. (S) | PRF1 | 0.4642 | 56 |
| SAM domain, SH3 domain and nuclear localisation signals, 1 (SAMSN1), mRNA. (S) | SAMSN1 | 0.4614 | 57 |
| TERF1 (TRF1)-interacting nuclear factor 2 (TINF2), mRNA. (S) | TINF2 | 0.4604 | 58 |
| endoplasmic reticulum-golgi intermediate compartment (ERGIC) 1 (ERGIC1), transcript variant 1, mRNA. (I) | ERGIC1 | 0.4554 | 59 |
| tumor necrosis factor, alpha-induced protein 2 (TNFAIP2), mRNA. (S) | TNFAIP2 | 0.455 | 60 |
| AT-hook transcription factor (AKNA), mRNA. (S) | AKNA | 0.4548 | 61 |
| adipose differentiation-related protein (ADFP), mRNA. (S) | ADFP | 0.4546 | 62 |
| pyruvate dehydrogenase kinase, isozyme 4 (PDK4), mRNA. (S) | PDK4 | 0.4538 | 63 |
| apoptotic peptidase activating factor (APAF1), transcript variant 5, mRNA. (A) | APAF1 | 0.4486 | 64 |
| signal transducer and activator of transcription 4 (STAT4), mRNA. (S) | STAT4 | 0.4478 | 65 |

TABLE I-continued

| GENE NAME | Symbol | Score | Rank |
|---|---|---|---|
| aldo-keto reductase family 1, member C3 (3-alpha hydroxysteroid dehydrogenase, type II), mRNA. (S) | AKR1C3 | 0.4454 | 66 |
| SH2 domain containing 3C (SH2D3C), transcript variant 2, mRNA. (I) | SH2D3C | 0.4444 | 67 |
| heat shock 105 kDa/110 kDa protein 1 (HSPH1), mRNA. (S) | HSPH1 | 0.4396 | 68 |
| phosphoinositide-3-kinase, regulatory subunit 1 (p85 alpha) (PIK3R1), transcript variant 2, mRNA. (A) | PIK3R1 | 0.4312 | 69 |
| presenilin associated, rhomboid-like (PSARL), mRNA. (S) | PSARL | 0.4284 | 70 |
| deoxyguanosine kinase, nuclear gene encoding mitochondrial protein, transcript variant 1, mRNA. (A) | DGUOK | 0.4272 | 71 |
| pleckstrin homology, Sec7 and coiled-coil domains, binding protein (PSCDBP), mRNA. (S) | PSCDBP | 0.4206 | 72 |
| uridine phosphorylase 1 (UPP1), transcript variant 2, mRNA. (A) | UPP1 | 0.4188 | 73 |
| solute carrier family 35 (CMP-sialic acid transporter), member A1 (SLC35A1), mRNA. (S) | SLC35A1 | 0.4176 | 74 |
| mitogen-activated protein kinase kinase kinase 8 (MAP3K8), mRNA. (S) | MAP3K8 | 0.4162 | 75 |
| chromosome 15 open reading frame 39 (C15orf39), mRNA. (S) | C15orf39 | 0.411 | 76 |
| ribosomal protein L35 (RPL35), mRNA. (S) | RPL35 | 0.4106 | 77 |
| rho/rac guanine nucleotide exchange factor (GEF) 2 (ARHGEF2), mRNA. (S) | ARHGEF2 | 0.4074 | 78 |
| chromosome 19 open reading frame 37 (C19orf37), mRNA. (S) | C19orf37 | 0.4072 | 79 |
| RNA binding motif protein 14 (RBM14), mRNA. (S) | RBM14 | 0.4068 | 80 |
| hypothetical protein MGC7036 (MGC7036), mRNA. (S) | MGC7036 | 0.4056 | 81 |
| poly(A) polymerase alpha (PAPOLA), mRNA. (S) | PAPOLA | 0.4044 | 82 |
| RAB10, member RAS oncogene family (RAB10), mRNA. (S) | RAB10 | 0.403 | 83 |
| chromosome 2 open reading frame 28 (C2orf28), transcript variant 2, mRNA. (A) | C2orf28 | 0.403 | 84 |
| LIM domain only 2 (rhombotin-like 1) (LMO2), mRNA. (S) | LMO2 | 0.3972 | 85 |
| polymerase (RNA) III (DNA directed) polypeptide G (32 kD) like (POLR3GL), mRNA. (S) | POLR3GL | 0.3968 | 86 |
| zinc finger and BTB domain containing 16 (ZBTB16), transcript variant 1, mRNA. (A) | ZBTB16 | 0.3948 | 87 |
| eukaryotic translation initiation factor 3, subunit 5 epsilon, 47 kDa (EIF3S5), mRNA. (S) | EIF3S5 | 0.3924 | 88 |
| HSCARG protein (HSCARG), mRNA. (S) | HSCARG | 0.3916 | 89 |
| synaptotagmin-like 3 (SYTL3), mRNA. (S) | SYTL3 | 0.3896 | 90 |
| hypothetical protein FLJ32028 (FLJ32028), mRNA. (S) | FLJ32028 | 0.3886 | 91 |
| leucine rich repeat containing 33 (LRRC33), mRNA. (S) | LRRC33 | 0.3862 | 92 |
| chromosome 1 open reading frame 162 (C1orf162), mRNA. (S) | C1orf162 | 0.3846 | 93 |
| cytochrome P450, family 2, subfamily R, polypeptide 1 (CYP2R1), mRNA. (S) | CYP2R1 | 0.3846 | 94 |
| jun D proto-oncogene (JUND), mRNA. (S) | JUND | 0.381 | 95 |
| melanoma antigen family D, 1 (MAGED1), transcript variant 1, mRNA. (A) | MAGED1 | 0.3806 | 96 |
| autism susceptibility candidate 2 (AUTS2), mRNA. (S) | AUTS2 | 0.3806 | 97 |
| oligodendrocyte transcription factor 1 (OLIG1), mRNA. (S) | OLIG1 | 0.379 | 98 |
| eukaryotic translation elongation factor 1 delta (guanine nucleotide exchange protein) (EEF1D), transcript variant 1, mRNA. (A) | EEF1D | 0.3776 | 99 |
| killer cell lectin-like receptor subfamily K, member 1 (KLRK1), mRNA. (S) | KLRK1 | 0.3736 | 100 |

TABLE II

| GENE NAME | Symbol | Score | Rank |
|---|---|---|---|
| v-ets erythroblastosis virus E26 oncogene homolog 1 (avian) (ETS1), mRNA. (S) | ETS1 | 0.9612 | 1 |
| chemokine (C-C motif) ligand 5 (CCL5), mRNA. (S) | CCL5 | 0.9438 | 2 |
| DNA-damage-inducible transcript 4 (DDIT4), mRNA. (S) | DDIT4 | 0.9024 | 3 |
| chemokine (C—X—C motif) receptor 4 (CXCR4), transcript variant 1, mRNA. (A) | CXCR4 | 0.8098 | 4 |

TABLE II-continued

| GENE NAME | Symbol | Score | Rank |
|---|---|---|---|
| dynein, cytoplasmic, light polypeptide 1 (DNCL1), mRNA. (S) | DNCL1 | 0.8058 | 5 |
| membrane-spanning 4-domains, subfamily A, member 6A (MS4A6A), transcript variant 2, mRNA. (I) | MS4A6A | 0.796 | 6 |
| ATP synthase, H+ transporting, mitochondrial F1 complex, beta polypeptide (ATP5B), nuclear gene encoding mitochondrial protein, mRNA. (S) | ATP5B | 0.7754 | 7 |
| heat shock 70 kDa protein 8 (HSPA8), transcript variant 1, mRNA. (I) | HSPA8 | 0.7718 | 8 |
| adrenomedullin (ADM), mRNA. (S) | ADM | 0.7708 | 9 |
| protein tyrosine phosphatase, non-receptor type 6 (PTPN6), transcript variant 3, mRNA. (A) | PTPN6 | 0.7576 | 10 |
| Rho GTPase activating protein 9 (ARHGAP9), mRNA. (S) | ARHGAP9 | 0.7548 | 11 |
| S100 calcium binding protein A8 (calgranulin A) (S100A8), mRNA. (S) | S100A8 | 0.7336 | 12 |
| dihydropyrimidinase-like 2 (DPYSL2), mRNA. (S) | DPYSL2 | 0.724 | 13 |
| heat shock 70 kDa protein 1A (HSPA1A), mRNA. (S) | HSPA1A | 0.7156 | 14 |
| nuclear factor of kappa light polypeptide gene enhancer in B-cells inhibitor, alpha (NFKBIA), mRNA. (S) | NFKBIA | 0.7132 | 15 |
| N-acetylglucosamine kinase (NAGK), mRNA. (S) | NAGK | 0.7098 | 16 |
| immunoglobulin superfamily, member 6 (IGSF6), mRNA. (S) | IGSF6 | 0.7088 | 17 |
| major histocompatibility complex, class II, DM beta (HLA-DMB), mRNA. (S) | HLA-DMB | 0.704 | 18 |
| family with sequence similarity 100, member B (FAM100B), mRNA. (S) | FAM100B | 0.7016 | 19 |
| myosin, light polypeptide 6, alkali, smooth muscle and non-muscle, transcript variant 1, mRNA. (A) | MYL6 | 0.6962 | 20 |
| solute carrier family 2 (facilitated glucose transporter), member 3 (SLC2A3), mRNA. (S) | SLC2A3 | 0.6738 | 21 |
| heat shock 70 kDa protein 8 (HSPA8), transcript variant 2, mRNA. (A) | HSPA8 | 0.653 | 22 |
| H2A histone family, member Z (H2AFZ), mRNA. (S) | H2AFZ | 0.6422 | 23 |
| Kruppel-like factor 9 (KLF9), mRNA. (S) | KLF9 | 0.6354 | 24 |
| tumor necrosis factor, alpha-induced protein 3 (TNFAIP3), mRNA. (S) | TNFAIP3 | 0.6312 | 25 |
| selenoprotein W, 1 (SEPW1), mRNA. (S) | SEPW1 | 0.6164 | 26 |
| sorting nexin 2 (SNX2), mRNA. (S) | SNX2 | 0.609 | 27 |
| dual specificity phosphatase 1 (DUSP1), mRNA. (S) | DUSP1 | 0.6076 | 28 |
| cystatin F (leukocystatin) (CST7), mRNA. (S) | CST7 | 0.5858 | 29 |
| PREDICTED: similar to 60S acidic ribosomal protein P1, transcript variant 4 (LOC440927), mRNA. (A) | LOC440927 | 0.5844 | 30 |
| PR domain containing 1, with ZNF domain (PRDM1), transcript variant 1, mRNA. (A) | PRDM1 | 0.581 | 31 |
| cold inducible RNA binding protein (CIRBP), mRNA. (S) | CIRBP | 0.5786 | 32 |
| cat eye syndrome chromosome region, candidate 1 (CECR1), transcript variant 1, mRNA. (A) | CECR1 | 0.575 | 33 |
| ATP synthase, H+ transporting, mitochondrial F1 complex, alpha subunit 1, cardiac muscle (ATP5A1), nuclear gene encoding mitochondrial protein, transcript variant 1, mRNA. (A) | ATP5A1 | 0.5664 | 34 |
| LIM domain only 2 (rhombotin-like 1) (LMO2), mRNA. (S) | LMO2 | 0.5608 | 35 |
| ral guanine nucleotide dissociation stimulator (RALGDS), mRNA. (S) | RALGDS | 0.5572 | 36 |
| G protein-coupled receptor 171 (GPR171), mRNA. (S) | GPR171 | 0.5536 | 37 |
| RNA binding motif protein 5 (RBM5), mRNA. (S) | RBM5 | 0.5532 | 38 |
| IL2-inducible T-cell kinase (ITK), mRNA. (S) | ITK | 0.545 | 39 |
| CTD (carboxy-terminal domain, RNA polymerase II, polypeptide A) small phosphatase 2 (S) | CTDSP2 | 0.542 | 40 |
| general transcription factor IIIA (GTF3A), mRNA. (S) | GTF3A | 0.5394 | 41 |
| myeloid-associated differentiation marker (MYADM), transcript variant 4, mRNA. (A) | MYADM | 0.5394 | 42 |
| NACHT, leucine rich repeat and PYD (pyrin domain) containing 1, transcript variant 5, mRNA. (I) | NALP1 | 0.5384 | 43 |
| DEAD (Asp-Glu-Ala-Asp) box polypeptide 17 (DDX17), transcript variant 2, mRNA. (A) | DDX17 | 0.5304 | 44 |
| thrombospondin 1 (THBS1), mRNA. (S) | THBS1 | 0.5278 | 45 |

TABLE II-continued

| GENE NAME | Symbol | Score | Rank |
|---|---|---|---|
| arachidonate 5-lipoxygenase (ALOX5), mRNA. (A) | ALOX5 | 0.523 | 46 |
| sparc/osteonectin, cwcv and kazal-like domains proteoglycan (testican) 2 (SPOCK2), mRNA. (S) | SPOCK2 | 0.5186 | 47 |
| hypothetical protein MGC7036 (MGC7036), mRNA. (S) | MGC7036 | 0.5182 | 48 |
| phosphoinositide-3-kinase, regulatory subunit 1 (p85 alpha) (PIK3R1), transcript variant 2, mRNA. (A) | PIK3R1 | 0.5176 | 49 |
| myeloid cell nuclear differentiation antigen (MNDA), mRNA. (S) | MNDA | 0.5158 | 50 |
| solute carrier family 35 (CMP-sialic acid transporter), member A1 (SLC35A1), mRNA. (S) | SLC35A1 | 0.5142 | 51 |
| chromosome 19 open reading frame 37 (C19orf37), mRNA. (S) | C19orf37 | 0.514 | 52 |
| granzyme M (lymphocyte met-ase 1) (GZMM), mRNA. (S) | GZMM | 0.5066 | 53 |
| transferrin receptor (p90, CD71) (TFRC), mRNA. (S) | TFRC | 0.5024 | 54 |
| mixed lineage kinase domain-like (MLKL), mRNA. (I) | MLKL | 0.501 | 55 |
| COMM domain containing 3 (COMMD3), mRNA. (S) | COMMD3 | 0.4976 | 56 |
| RAB24, member RAS oncogene family (RAB24), transcript variant 2, mRNA. (A) | RAB24 | 0.497 | 57 |
| PREDICTED: similar to heterogeneous nuclear ribonucleoprotein A1 (LOC645385), mRNA. (S) | LOC645385 | 0.4966 | 58 |
| RNA binding motif protein 14 (RBM14), mRNA. (S) | RBM14 | 0.4948 | 59 |
| pleckstrin homology, Sec7 and coiled-coil domains 4 (PSCD4), mRNA. (S) | PSCD4 | 0.4928 | 60 |
| zinc finger, DHHC-type containing 7 (ZDHHC7), mRNA. (S) | ZDHHC7 | 0.489 | 61 |
| protein kinase C, eta (PRKCH), mRNA. (S) | PRKCH | 0.4886 | 62 |
| hypothetical protein MGC11257 (MGC11257), mRNA. (S) | MGC11257 | 0.4854 | 63 |
| heat shock 105 kDa/110 kDa protein 1 (HSPH1), mRNA. (S) | HSPH1 | 0.4812 | 64 |
| retinoid X receptor, alpha (RXRA), mRNA. (S) | RXRA | 0.481 | 65 |
| bicaudal D homolog 2 (Drosophila) (BICD2), transcript variant 1, mRNA. (A) | BICD2 | 0.4756 | 66 |
| solute carrier family 27 (fatty acid transporter), member 3 (SLC27A3), mRNA. (S) | SLC27A3 | 0.47 | 67 |
| CD96 antigen (CD96), transcript variant 1, mRNA. (A) | CD96 | 0.4688 | 68 |
| ribosomal protein S2 (RPS2), mRNA. (S) | RPS2 | 0.4662 | 69 |
| insulin receptor substrate 2 (IRS2), mRNA. (S) | IRS2 | 0.4654 | 70 |
| protein tyrosine phosphatase, non-receptor type substrate 1 (PTPNS1), mRNA. (S) | PTPNS1 | 0.4612 | 71 |
| ral guanine nucleotide dissociation stimulator-like 2 (RGL2), mRNA. (S) | RGL2 | 0.457 | 72 |
| PREDICTED: similar to Translationally-controlled tumor protein (TCTP) (p23) (Histamine-releasing factor) (HRF) (Fortilin) (LOC643870), mRNA. (S) | LOC643870 | 0.4566 | 73 |
| MID1 interacting protein 1 (gastrulation specific G12-like (zebrafish)) (MID1IP1), mRNA. (S) | MID1IP1 | 0.454 | 74 |
| solute carrier family 7 (cationic amino acid transporter, y+ system), member 7 (SLC7A7), mRNA. (S) | SLC7A7 | 0.4502 | 75 |
| FK506 binding protein 11, 19 kDa (FKBP11), mRNA. (S) | FKBP11 | 0.4492 | 76 |
| SH2 domain containing 3C (SH2D3C), transcript variant 2, mRNA. (I) | SH2D3C | 0.4454 | 77 |
| rho/rac guanine nucleotide exchange factor (GEF) 2 (ARHGEF2), mRNA. (S) | ARHGEF2 | 0.4444 | 78 |
| nucleoporin 62 kDa (NUP62), transcript variant 1, mRNA. (A) | NUP62 | 0.4424 | 79 |
| hypothetical protein FLJ20186 (FLJ20186), transcript variant 1, mRNA. (I) | FLJ20186 | 0.438 | 80 |
| ATPase, H+ transporting, lysosomal 56/58 kDa, V1 subunit B, isoform 2 (ATP6V1B2), mRNA. (S) | ATP6V1B2 | 0.436 | 81 |
| v-yes-1 Yamaguchi sarcoma viral related oncogene homolog (LYN), mRNA. (S) | LYN | 0.4358 | 82 |
| tumor necrosis factor, alpha-induced protein 2 (TNFAIP2), mRNA. (S) | TNFAIP2 | 0.433 | 83 |
| ST3 beta-galactoside alpha-2,3-sialyltransferase 1 (ST3GAL1), transcript variant 2, mRNA. (A) | ST3GAL1 | 0.4318 | 84 |

TABLE II-continued

| GENE NAME | Symbol | Score | Rank |
|---|---|---|---|
| GABA(A) receptor-associated protein like 1 (GABARAPL1), mRNA. (S) | GABARAPL1 | 0.4276 | 85 |
| DCP2 decapping enzyme homolog (*S. cerevisiae*) (DCP2), mRNA. (S) | DCP2 | 0.4272 | 86 |
| family with sequence similarity 46, member A (FAM46A), mRNA. (S) | FAM46A | 0.4266 | 87 |
| mitochondrial ribosomal protein L51 (MRPL51), nuclear gene encoding mitochondrial protein, mRNA. (S) | MRPL51 | 0.4256 | 89 |
| chemokine (C-C motif) ligand 4-like 1 (CCL4L1), mRNA. (S) | CCL4L1 | 0.4208 | 90 |
| deoxyguanosine kinase, nuclear gene encoding mitochondrial protein, transcript variant 1, mRNA. (A) | DGUOK | 0.4204 | 91 |
| frequently rearranged in advanced T-cell lymphomas 2 (FRAT2), mRNA. (S) | FRAT2 | 0.4202 | 92 |
| SH3-domain kinase binding protein 1 (SH3KBP1), transcript variant 1, mRNA. (I) | SH3KBP1 | 0.4172 | 93 |
| dual specificity phosphatase 2 (DUSP2), mRNA. (S) | DUSP2 | 0.4172 | 94 |
| eukaryotic translation initiation factor 2B, subunit 4 delta, 67 kDa, transcript variant 1, mRNA. (A) | EIF2B4 | 0.4136 | 95 |
| fibrinogen-like 2 (FGL2), mRNA. (S) | FGL2 | 0.4126 | 96 |
| glucosidase, alpha; neutral AB (GANAB), transcript variant 2, mRNA. (A) | GANAB | 0.4112 | 97 |
| CCAAT/enhancer binding protein (C/EBP), alpha (CEBPA), mRNA. (S) | CEBPA | 0.41 | 98 |
| prolylcarboxypeptidase (angiotensinase C) (PRCP), transcript variant 2, mRNA. (A) | PRCP | 0.4046 | 99 |
| succinate-CoA ligase, GDP-forming, beta subunit (SUCLG2), mRNA. (S) | SUCLG2 | 0.4012 | 100 |

TABLE III

| GENE NAME | Symbol | Score | Rank |
|---|---|---|---|
| TSC22 domain family, member 3 (TSC22D3), transcript variant 2, mRNA. (A) | TSC22D3 | 0.9522 | 1 |
| chemokine (C—X—C motif) receptor 4 (CXCR4), transcript variant 1, mRNA. (A) | CXCR4 | 0.9444 | 2 |
| dynein, cytoplasmic, light polypeptide 1 (DNCL1), mRNA. (S) | DNCL1 | 0.8668 | 3 |
| ribosomal protein S3 (RPS3), mRNA. (S) | RPS3 | 0.8556 | 4 |
| DNA-damage-inducible transcript 4 (DDIT4), mRNA. (S) | DDIT4 | 0.8502 | 5 |
| granzyme B (granzyme 2, cytotoxic T-lymphocyte-associated serine esterase 1) (GZMB), mRNA. (S) | GZMB | 0.8148 | 6 |
| B-cell translocation gene 1, anti-proliferative (BTG1), mRNA. (S) | BTG1 | 0.8 | 7 |
| heat shock 70 kDa protein 8 (HSPA8), transcript variant 1, mRNA. (I) | HSPA8 | 0.793 | 8 |
| ribosomal protein L12 (RPL12), mRNA. (S) | RPL12 | 0.7564 | 9 |
| Src-like-adaptor (SLA), mRNA. (S) | SLA | 0.7322 | 10 |
| runt-related transcription factor 3 (RUNX3), transcript variant 1, mRNA. (I) | RUNX3 | 0.7306 | 11 |
| HGFL gene (MGC17330), mRNA. (S) | MGC17330 | 0.6982 | 12 |
| heat shock 70 kDa protein 1A (HSPA1A), mRNA. (S) | HSPA1A | 0.684 | 13 |
| interleukin 18 receptor accessory protein (IL18RAP), mRNA. (S) | IL18RAP | 0.6728 | 14 |
| cold inducible RNA binding protein (CIRBP), mRNA. (S) | CIRBP | 0.67 | 15 |
| adrenomedullin (ADM), mRNA. (S) | ADM | 0.662 | 16 |
| CCAAT/enhancer binding protein (C/EBP), beta (CEBPB), mRNA. (S) | CEBPB | 0.654 | 17 |
| PREDICTED: similar to heterogeneous nuclear ribonucleoprotein A1 (LOC645385), mRNA. (S) | LOC645385 | 0.654 | 18 |
| CCAAT/enhancer binding protein (C/EBP), delta (CEBPD), mRNA. (S) | CEBPD | 0.6416 | 19 |
| Kruppel-like factor 9 (KLF9), mRNA. (S) | KLF9 | 0.6392 | 20 |
| PREDICTED: hypothetical protein LOC440345, transcript variant 6 (LOC440345), mRNA. (I) | LOC440345 | 0.6358 | 21 |
| inhibitor of DNA binding 2, dominant negative helix-loop-helix protein (ID2), mRNA. (S) | ID2 | 0.617 | 22 |
| killer cell Ig-like receptor, two domains, long cytoplasmic tail 3, transcript variant 2, mRNA. (A) | KIR2DL3 | 0.6126 | 23 |
| arachidonate 5-lipoxygenase-activating protein (ALOX5AP), mRNA. (S) | ALOX5AP | 0.6106 | 24 |

TABLE III-continued

| GENE NAME | Symbol | Score | Rank |
|---|---|---|---|
| immunoglobulin superfamily, member 6 (IGSF6), mRNA. (S) | IGSF6 | 0.6068 | 25 |
| heat shock 70 kDa protein 8 (HSPA8), transcript variant 2, mRNA. (A) | HSPA8 | 0.6032 | 27 |
| tubulin, alpha, ubiquitous (K-ALPHA-1), mRNA. (S) | K-ALPHA-1 | 0.6002 | 28 |
| protein kinase C, delta (PRKCD), transcript variant 2, mRNA. (A) | PRKCD | 0.5992 | 29 |
| PR domain containing 1, with ZNF domain (PRDM1), transcript variant 1, mRNA. (A) | PRDM1 | 0.594 | 30 |
| CD55 antigen, decay accelerating factor for complement (Cromer blood group) (CD55), mRNA. (S) | CD55 | 0.5722 | 31 |
| cystatin F (leukocystatin) (CST7), mRNA. (S) | CST7 | 0.5698 | 32 |
| myeloid-associated differentiation marker (MYADM), transcript variant 4, mRNA. (A) | MYADM | 0.568 | 33 |
| major histocompatibility complex, class I, F (HLA-F), mRNA. (S) | HLA-F | 0.568 | 34 |
| SH2 domain protein 2A (SH2D2A), mRNA. (S) | SH2D2A | 0.5656 | 35 |
| potassium channel tetramerisation domain containing 12 (KCTD12), mRNA. (S) | KCTD12 | 0.5638 | 36 |
| Ras-GTPase-activating protein SH3-domain-binding protein (G3BP), transcript variant 1, mRNA. (A) | G3BP | 0.5636 | 37 |
| fibrinogen-like 2 (FGL2), mRNA. (S) | FGL2 | 0.5552 | 38 |
| CCAAT/enhancer binding protein (C/EBP), alpha (CEBPA), mRNA. (S) | CEBPA | 0.5368 | 39 |
| DnaJ (Hsp40) homolog, subfamily A, member 1 (DNAJA1), mRNA. (S) | DNAJA1 | 0.5306 | 40 |
| capping protein (actin filament) muscle Z-line, alpha 2 (CAPZA2), mRNA. (S) | CAPZA2 | 0.5244 | 41 |
| general transcription factor IIIA (GTF3A), mRNA. (S) | GTF3A | 0.523 | 42 |
| IBR domain containing 2 (IBRDC2), mRNA. (S) | IBRDC2 | 0.5228 | 43 |
| interferon stimulated exonuclease gene 20 kDa (ISG20), mRNA. (S) | ISG20 | 0.5208 | 44 |
| PREDICTED: similar to ribosomal protein L13a, transcript variant 4 (LOC649564), mRNA. (A) | LOC649564 | 0.5134 | 45 |
| G protein-coupled receptor 171 (GPR171), mRNA. (S) | GPR171 | 0.5124 | 46 |
| killer cell immunoglobulin-like receptor, two domains, long cytoplasmic tail, 4 (KIR2DL4), mRNA. (S) | KIR2DL4 | 0.5044 | 47 |
| sin3-associated polypeptide, 30 kDa (SAP30), mRNA. (S) | SAP30 | 0.4972 | 48 |
| PREDICTED: meteorin, glial cell differentiation regulator-like (METRNL), mRNA. (I) | METRNL | 0.4936 | 49 |
| chloride intracellular channel 3 (CLIC3), mRNA. (S) | CLIC3 | 0.4926 | 50 |
| eukaryotic translation initiation factor 3, subunit 12 (EIF3S12), mRNA. (S) | EIF3S12 | 0.4912 | 51 |
| insulin receptor substrate 2 (IRS2), mRNA. (S) | IRS2 | 0.4824 | 52 |
| hepatitis A virus cellular receptor 2 (HAVCR2), mRNA. (S) | HAVCR2 | 0.4758 | 53 |
| HD domain containing 2 (HDDC2), mRNA. (S) | HDDC2 | 0.4754 | 54 |
| nuclear RNA export factor 1 (NXF1), mRNA. (S) | NXF1 | 0.468 | 55 |
| perforin 1 (pore forming protein) (PRF1), mRNA. (S) | PRF1 | 0.4642 | 56 |
| SAM domain, SH3 domain and nuclear localisation signals, 1 (SAMSN1), mRNA. (S) | SAMSN1 | 0.4614 | 57 |
| TERF1 (TRF1)-interacting nuclear factor 2 (TINF2), mRNA. (S) | TINF2 | 0.4604 | 58 |
| endoplasmic reticulum-golgi intermediate compartment (ERGIC) 1, transcript variant 1, mRNA. (I) | ERGIC1 | 0.4554 | 59 |
| tumor necrosis factor, alpha-induced protein 2 (TNFAIP2), mRNA. (S) | TNFAIP2 | 0.455 | 60 |
| AT-hook transcription factor (AKNA), mRNA. (S) | AKNA | 0.4548 | 61 |
| adipose differentiation-related protein (ADFP), mRNA. (S) | ADFP | 0.4546 | 62 |
| pyruvate dehydrogenase kinase, isozyme 4 (PDK4), mRNA. (S) | PDK4 | 0.4538 | 63 |
| apoptotic peptidase activating factor (APAF1), transcript variant 5, mRNA. (A) | APAF1 | 0.4486 | 64 |
| signal transducer and activator of transcription 4 (STAT4), mRNA. (S) | STAT4 | 0.4478 | 65 |
| aldo-keto reductase family 1, member C3 (3-alpha hydroxysteroid dehydrogenase, type II), mRNA. (S) | AKR1C3 | 0.4454 | 66 |
| SH2 domain containing 3C (SH2D3C), transcript variant 2, mRNA. (I) | SH2D3C | 0.4444 | 67 |
| heat shock 105 kDa/110 kDa protein 1 (HSPH1), mRNA. (S) | HSPH1 | 0.4396 | 68 |
| phosphoinositide-3-kinase, regulatory subunit 1 (p85 alpha) (PIK3R1), transcript variant 2, mRNA. (A) | PIK3R1 | 0.4312 | 69 |
| presenilin associated, rhomboid-like (PSARL), mRNA. (S) | PSARL | 0.4284 | 70 |
| deoxyguanosine kinase, nuclear gene encoding mitochondrial protein, transcript variant 1, mRNA. (A) | DGUOK | 0.4272 | 71 |
| pleckstrin homology, Sec7 and coiled-coil domains, binding protein (PSCDBP), mRNA. (S) | PSCDBP | 0.4206 | 72 |

TABLE III-continued

| GENE NAME | Symbol | Score | Rank |
|---|---|---|---|
| uridine phosphorylase 1 (UPP1), transcript variant 2, mRNA. (A) | UPP1 | 0.4188 | 73 |
| solute carrier family 35 (CMP-sialic acid transporter), member A1 (SLC35A1), mRNA. (S) | SLC35A1 | 0.4176 | 74 |
| mitogen-activated protein kinase kinase kinase 8 (MAP3K8), mRNA. (S) | MAP3K8 | 0.4162 | 75 |
| chromosome 15 open reading frame 39 (C15orf39), mRNA. (S) | C15orf39 | 0.411 | 76 |
| ribosomal protein L35 (RPL35), mRNA. (S) | RPL35 | 0.4106 | 77 |
| rho/rac guanine nucleotide exchange factor (GEF) 2 (ARHGEF2), mRNA. (S) | ARHGEF2 | 0.4074 | 78 |
| chromosome 19 open reading frame 37 (C19orf37), mRNA. (S) | C19orf37 | 0.4072 | 79 |
| RNA binding motif protein 14 (RBM14), mRNA. (S) | RBM14 | 0.4068 | 80 |
| hypothetical protein MGC7036 (MGC7036), mRNA. (S) | MGC7036 | 0.4056 | 81 |
| poly(A) polymerase alpha (PAPOLA), mRNA. (S) | PAPOLA | 0.4044 | 82 |
| RAB10, member RAS oncogene family (RAB10), mRNA. (S) | RAB10 | 0.403 | 83 |
| chromosome 2 open reading frame 28 (C2orf28), transcript variant 2, mRNA. (A) | C2orf28 | 0.403 | 84 |
| LIM domain only 2 (rhombotin-like 1) (LMO2), mRNA. (S) | LMO2 | 0.3972 | 85 |
| polymerase (RNA) III (DNA directed) polypeptide G (32 kD) like (POLR3GL), mRNA. (S) | POLR3GL | 0.3968 | 86 |
| zinc finger and BTB domain containing 16 (ZBTB16), transcript variant 1, mRNA. (A) | ZBTB16 | 0.3948 | 87 |
| eukaryotic translation initiation factor 3, subunit 5 epsilon, 47 kDa (EIF3S5), mRNA. (S) | EIF3S5 | 0.3924 | 88 |
| HSCARG protein (HSCARG), mRNA. (S) | HSCARG | 0.3916 | 89 |
| synaptotagmin-like 3 (SYTL3), mRNA. (S) | SYTL3 | 0.3896 | 90 |
| hypothetical protein FLJ32028 (FLJ32028), mRNA. (S) | FLJ32028 | 0.3886 | 91 |
| leucine rich repeat containing 33 (LRRC33), mRNA. (S) | LRRC33 | 0.3862 | 92 |
| chromosome 1 open reading frame 162 (C1orf162), mRNA. (S) | C1orf162 | 0.3846 | 93 |
| cytochrome P450, family 2, subfamily R, polypeptide 1 (CYP2R1), mRNA. (S) | CYP2R1 | 0.3846 | 94 |
| jun D proto-oncogene (JUND), mRNA. (S) | JUND | 0.381 | 95 |
| melanoma antigen family D, 1 (MAGED1), transcript variant 1, mRNA. (A) | MAGED1 | 0.3806 | 96 |
| autism susceptibility candidate 2 (AUTS2), mRNA. (S) | AUTS2 | 0.3806 | 97 |
| oligodendrocyte transcription factor 1 (OLIG1), mRNA. (S) | OLIG1 | 0.379 | 98 |
| eukaryotic translation elongation factor 1 delta (guanine nucleotide exchange protein) (EEF1D), transcript variant 1, mRNA. (A) | EEF1D | 0.3776 | 99 |
| killer cell lectin-like receptor subfamily K, member 1 (KLRK1), mRNA. (S) | KLRK1 | 0.3736 | 100 |

TABLE IV

Top 15 Gene Classifiers

| Rank | ALL/NHC | AC/NHC | PRE/POST |
|---|---|---|---|
| 1 | IGSF6 | ETS1 | TSC22D3 |
| 2 | HSPA8(A) | CCL5 | CXCR4 |
| 3 | LYN | DDIT4 | DNCL1 |
| 4 | DNCL1 | CSCR4 | RPS3 |
| 5 | HSPA1A | DNCL1 | DDIT4 |
| 6 | DPYSL2 | MS4A6A | GZMB |
| 7 | NAGK | ATP5B | BTG1 |
| 8 | HSPA8(I) | HSPA8(A) | HSPA8(I) |
| 9 | NFKBIA | ADM | RPL12 |
| 10 | FGL2 | PTPN6 | SLA |
| 11 | CALM2 | ARHGAP9 | RUNX3 |
| 12 | CCL5 | S100A8 | MGC17330 |
| 13 | RPS2 | DPYSL2 | HSPA1A |
| 14 | DDIT4 | HSPA1A | IL18RAP |
| 15 | C1orf63 | NFKBIA | CIRBP |

TABLE V

| Spot ID | Accession No. | GENE NAME | Symbol | Rank | Fold Chg |
|---|---|---|---|---|---|
| 5490167 | NM_016578 | hepatitis B virus x associated protein (HBXAP), mRNA. (S); or alternatively, called Remodeling and splicing factor 1 | HBXAP or RSF1 | 1 | 1.27 |
| 3890735 | NM_003583 | dual-specificity tyrosine-(Y)-phosphorylation regulated | DYRK2 | 2 | −1.34 |

TABLE V-continued

| Spot ID | Accession No. | GENE NAME | Symbol | Rank | Fold Chg |
|---|---|---|---|---|---|
| | | kinase 2 (DYRK2), transcript variant 1, mRNA. (A) | | | |
| 3840377 | NM_003403 | YY1 transcription factor (YY1), mRNA. (S) | YY1 | 3 | -1.08 |
| 1470605 | NM_001031726 | chromosome 19 open reading frame 12, transcript variant 1, mRNA. (I) | C19orf12 | 4 | 1.36 |
| 4230709 | NM_018473 | thioesterase superfamily member 2 (THEM2), mRNA. (S) | THEM2 | 5 | -1.13 |
| 1430678 | NM_007118 | triple functional domain (PTPRF interacting) (TRIO), mRNA. (S) | TRIO | 6 | -1.16 |
| 1340086 | NM_001020820 | myeloid-associated differentiation marker, transcript variant 4, mRNA. (A) | MYADM | 7 | -1.34 |
| 2940370 | NM_017450 | BAI1-associated protein 2 (BAIAP2), transcript variant 1, mRNA. (I) | BAIAP2 | 8 | -1.34 |
| 6400075 | NM_024589 | leucine zipper domain protein (FLJ22386), mRNA. (S); or alternatively Rogdi homolog (*Drosophila*) | FLJ22386 or ROGDI | 9 | -1.18 |
| 20196 | NM_024920 | DnaJ (Hsp40) homolog, subfamily B, member 14 (DNAJB14), transcript variant 2, mRNA. (I) | DNAJB14 | 10 | -1.14 |
| 7330360 | NM_199191 | brain and reproductive organ-expressed (TNFRSF1A modulator) (BRE), transcript variant 3, mRNA. (A) | BRE | 11 | 1.04 |
| 240280 | NM_080652 | transmembrane protein 41A (TMEM41A), mRNA. (S) | TMEM41A | 12 | 1.15 |
| 3940687 | NM_032307 | chromosome 9 open reading frame 64 (C9orf64), mRNA. (S) | C9orf64 | 13 | -1.14 |
| 4150253 | NM_031424 | chromosome 20 open reading frame 55, transcript variant 1, mRNA. (A); or alternatively, Family with sequence similarity 110, member A | C20orf55 or FAM110A | 14 | -1.14 |
| 1660445 | NM_014801 | pecanex-like 2 (*Drosophila*) (PCNXL2), transcript variant 1, mRNA. (I) | PCNXL2 | 15 | 1.21 |
| 4120187 | NM_005612 | RE1-silencing transcription factor (REST), mRNA. (S) | REST | 16 | 1.29 |
| 7610494 | NM_014173 | HSPC142 protein (HSPC142), transcript variant 2, mRNA. (A); or alternatively, Chromosome 19 open reading frame 62 | HSPC142 or C19orf62 | 17 | 1.10 |
| 4250121 | NM_138779 | hypothetical protein BC015148 (LOC93081), mRNA. (S); or alternatively, Chromosome 13 open reading frame 27 | LOC93081 or C13orf27 | 18 | -1.18 |
| 4810674 | NM_022091 | activating signal cointegrator 1 complex subunit 3 (ASCC3), transcript variant 2, mRNA. (A) | ASCC3 | 19 | 1.83 |
| 3460224 | NM_005628 | solute carrier family 1 (neutral amino acid transporter), member 5 (SLC1A5), mRNA. (S) | SLC1A5 | 20 | -1.16 |
| 1110110 | NM_016395 | protein tyrosine phosphatase-like A domain containing 1, mRNA. (A) | PTPLAD1 | 21 | -1.22 |
| 2630397 | NM_005590 | MRE11 meiotic recombination 11 homolog A (*S. cerevisiae*) (MRE11A), transcript variant 2, mRNA. (A) | MRE11A | 22 | -1.18 |
| 1400541 | NM_033107 | hypothetical protein (DKFZP686A10121), mRNA. (S); or alternatively, GTP- | DKFZP686A10121 or GTPBP10 | 23 | -1.27 |

TABLE V-continued

| Spot ID | Accession No. | GENE NAME | Symbol | Rank | Fold Chg |
|---|---|---|---|---|---|
| | | binding protein 10 (putative), transcript variant 2 | | | |
| 4390100 | BX118737 | BX118737 Soares fetal liver spleen 1NFLS cDNA clone IMAGp998K18127, mRNA sequence (S) | NaN | 24 | −1.40 |
| 1500246 | NM_006217 | serpin peptidase inhibitor, clade I (pancpin), member 2 (SERPINI2), transcript variant 2, mRNA. (S) | SERPINI2 | 25 | −1.41 |
| 6590377 | AK126342 | cDNA FLJ44370 fis, clone TRACH3008902 (S); or alternatively, cAMP responsive element binding protein 1 | NaN or CREB1 | 26 | −1.45 |
| 3710754 | NM_016053 | coiled-coil domain containing 53 (CCDC53), mRNA. (S) | CCDC53 | 27 | −1.07 |
| 990112 | NM_032236 | ubiquitin specific peptidase 48 (USP48), transcript variant 1, mRNA. (I) | USP48 | 28 | −1.17 |
| 2640255 | NM_001007072 | zinc finger and SCAN domain containing 2, transcript variant 3, mRNA (I) | ZSCAN2 | 29 | 1.18 |
| 2370482 | NM_024754 | pentatricopeptide repeat domain 2 (PTCD2), mRNA. (S) | PTCD2 | 30 | |
| 6380040 | NM_025201 | pleckstrin homology domain containing, family Q member 1 mRNA. (S) | PLEKHQ1 | 31 | |
| 6370338 | AW191734 | HIMC10.07.00 human islet cDNA differential display cDNA, mRNA sequence (S) | NaN | 32 | |
| 5340544 | NM_002616 | period homolog 1 (*Drosophila*) (PER1), mRNA. (S) | PER1 | 33 | |
| 5910367 | NM_012154 | eukaryotic translation initiation factor 2C, 2 (EIF2C2), mRNA. (S) | EIF2C2 | 34 | |
| 2570440 | NM_022128 | ribokinase (RBKS), mRNA. (S) | RBKS | 35 | |
| 6100707 | NM_002419 | mitogen-activated protein kinase kinase kinase 11, mRNA. (S) | MAP3K11 | 36 | |
| 2490615 | NM_207443 | FLJ45244 protein (FLJ45244), mRNA. (S) | FLJ45244 | 37 | |
| 6580368 | NM_006611 | killer cell lectin-like receptor subfamily A, member 1, mRNA. (S) | KLRA1 | 38 | |
| 4570553 | NM_016282 | adenylate kinase 3 (AK3), mRNA. (S) | AK3 | 39 | |
| 5130500 | BG741535 | 602635144F1 NCI_CGAP_Skn3 cDNA clone IMAGE: 4780090 5, mRNA sequence (S) | NaN | 40 | |
| 1240026 | NM_001003941 | oxoglutarate (alpha-ketoglutarate) dehydrogenase (lipoamide), nuclear gene encoding mitochondrial protein, transcript variant 2, mRNA. (I) | OGDH | 41 | |
| 2680593 | NM_006582 | glucocorticoid modulatory element binding protein 1 (GMEB1), transcript variant 1, mRNA. (A) | GMEB1 | 42 | |
| 130403 | NM_006567 | phenylalanine-tRNA synthetase 2 (mitochondrial) (FARS2), nuclear gene encoding mitochondrial protein, mRNA. (S) | FARS2 | 43 | |
| 1710338 | NM_170768 | zinc finger protein 91 homolog (mouse), transcript variant 2, mRNA. (A) | ZFP91 | 44 | |
| 150021 | NM_013285 | guanine nucleotide binding protein-like 2 (nucleolar) (GNL2), mRNA. (S) | GNL2 | 45 | |

TABLE V-continued

| Spot ID | Accession No. | GENE NAME | Symbol | Rank | Fold Chg |
|---|---|---|---|---|---|
| 4250703 | XM_498909 | PREDICTED: hypothetical LOC440900 (LOC440900), mRNA. (S) | LOC440900 | 46 | |
| 7000731 | NM_020453 | ATPase, Class V, type 10D (ATP10D), mRNA. (S) | ATP10D | 47 | |
| 4590563 | XM_942240 | PREDICTED: similar to HLA class II histocompatibility antigen, DQ (W1.1) beta chain precursor (DQB1*0501), transcript variant 1 (LOC650557), mRNA. (A) | LOC650557 | 48 | |
| 3310446 | NM_018169 | chromosome 12 open reading frame 35 (C12orf35), mRNA. (S) | C12orf35 | 49 | |
| 3460066 | XM_932088 | PREDICTED: hypothetical protein LOC642788, transcript variant 2 (LOC642788), mRNA. (A) | LOC642788 | 50 | |
| 160152 | NM_003789 | TNFRSF1A-associated via death domain transcript variant 1, mRNA. (A) | TRADD | 51 | |
| 840379 | NM_031212 | solute carrier family 25, member 28 (SLC25A28), mRNA. (S) | SLC25A28 | 52 | |
| 4050402 | BX459101 | BX459101 PLACENTA cDNA clone CS0DE012YP17 5-PRIME, mRNA sequence (S) | NaN | 53 | |
| 3440441 | AK124002 | cDNA FLJ42008 fis, clone SPLEN2031724 (S) | NaN | 54 | |
| 5390504 | NM_001165 | baculoviral IAP repeat-containing 3, transcript variant 1, mRNA. (I) | BIRC3 | 55 | |
| 5490564 | XM_940798 | PREDICTED: similar to Bcl-2-associated transcription factor 1 (Btf), transcript variant 1 (LOC650759), mRNA. (I) | LOC650759 | 56 | |
| 1940220 | XM_940538 | PREDICTED: protein tyrosine phosphatase-like A domain containing 1 (PTPLAD1), mRNA. (A) | PTPLAD1 | 57 | |
| 770221 | NM_005950 | metallothionein 1G (MT1G), mRNA. (S) | MT1G | 58 | |
| 1500647 | NM_005665 | ecotropic viral integration site 5 (EVI5), mRNA. (S) | EVI5 | 59 | |
| 5900730 | NM_005813 | protein kinase D3 (PRKD3), mRNA. (S) | PRKD3 | 60 | |
| 1980689 | NM_024029 | Yip1 domain family, member 2 (YIPF2), mRNA. (S) | YIPF2 | 61 | |
| 770253 | NM_024076 | potassium channel tetramerisation domain containing 15, mRNA. (S) | KCTD15 | 62 | |
| 2260484 | NM_022070 | amplified in breast cancer 1 (ABC1), mRNA. (S) | ABC1 | 63 | |
| 380561 | NM_020773 | TBC1 domain family, member 14 (TBC1D14), mRNA. (S) | TBC1D14 | 64 | |
| 780576 | NM_014238 | kinase suppressor of ras 1 (KSR1), mRNA. (S) | KSR1 | 65 | |
| 240292 | BG564169 | 602590145F1 NIH_MGC_76 cDNA clone IMAGE: 4724074 5, mRNA sequence (S) | NaN | 66 | |
| 6590021 | NM_024804 | zinc finger protein 669 (ZNF669), mRNA. (S) | ZNF669 | 67 | |
| 6330471 | NM_004337 | chromosome 8 open reading frame 1 (C8orf1), mRNA. (S) | C8orf1 | 68 | |
| 3170398 | NM_000747 | cholinergic receptor, nicotinic, beta 1 (muscle) (CHRNB1), mRNA. (S) | CHRNB1 | 69 | |
| 3170477 | NM_001004489 | olfactory receptor, family 2, subfamily AG, member 1, mRNA. (S) | OR2AG1 | 70 | |
| 2510563 | NM_024874 | KIAA0319-like (KIAA0319L), transcript variant 1, mRNA. (I) | KIAA0319L | 71 | |
| 2510280 | NM_015106 | RAD54-like 2 (S. cerevisiae) (RAD54L2), mRNA. (S) | RAD54L2 | 72 | |

TABLE V-continued

| Spot ID | Accession No. | GENE NAME | Symbol | Rank | Fold Chg |
|---|---|---|---|---|---|
| 4670685 | NM_003557 | phosphatidylinositol-4-phosphate 5-kinase, type I, alpha, mRNA. (S) | PIP5K1A | 73 | |
| 4230736 | NM_001329 | C-terminal binding protein 2 (CTBP2), transcript variant 1, mRNA. (I) | CTBP2 | 74 | |
| 7510164 | XM_938545 | PREDICTED: similar to Formin-binding protein 3 (Formin-binding protein 11) (FBP 11), transcript variant 1 (LOC648039), mRNA. (I) | LOC648039 | 75 | |
| 4210576 | NM_022490 | polymerase (RNA) I associated factor 1 (PRAF1), mRNA. (S) | PRAF1 | 76 | |
| 5910376 | NM_003246 | thrombospondin 1 (THBS1), mRNA. (S) | THBS1 | 77 | |
| 2480202 | NM_006933 | solute carrier family 5 (inositol transporters), member 3, mRNA. (S) | SLC5A3 | 78 | |
| 5960035 | NM_170699 | G protein-coupled bile acid receptor 1 (GPBAR1), mRNA. (S) | GPBAR1 | 79 | |
| 5290192 | CR616845 | full-length cDNA clone CS0DF020YJ04 of Fetal brain of (human) (S) | NaN | 80 | |
| 1170301 | NM_014572 | LATS, large tumor suppressor, homolog 2 (Drosophila), mRNA. (S) | LATS2 | 81 | |
| 2340224 | NM_181724 | transmembrane protein 119 (TMEM119), mRNA. (S) | TMEM119 | 82 | |
| 4210008 | NM_022168 | interferon induced with helicase C domain 1 (IFIH1), mRNA. (S) | IFIH1 | 83 | |
| 3060563 | CD639673 | AGENCOURT_14534956 NIH_MGC_191 cDNA clone IMAGE: 30418908 5, mRNA sequence (S) | NaN | 84 | |
| 7320600 | AK123531 | cDNA FLJ41537 fis, clone BRTHA2017985 (S) | NaN | 85 | |
| 520097 | NM_003541 | histone 1, H4k (HIST1H4K), mRNA. (S) | HIST1H4K | 86 | |
| 5270315 | NM_001240 | cyclin T1 (CCNT1), mRNA. (S) | CCNT1 | 87 | |
| 2690008 | BC025734 | Homo sapiens, clone IMAGE: 5204729, mRNA (S) | NaN | 88 | |
| 110044 | NM_001001795 | similar to RIKEN cDNA C030006K11 gene (MGC70857), mRNA. (S) | MGC70857 | 89 | |
| 2030487 | BX118124 | BX118124 Soares_parathyroid_tumor_Nb HPA cDNA clone IMAGp998P234189, mRNA sequence (S) | NaN | 90 | |
| 1170139 | NM_033141 | mitogen-activated protein kinase kinase kinase 9 (MAP3K9), mRNA. (S) | MAP3K9 | 91 | |
| 1190300 | NM_015353 | potassium channel tetramerisation domain containing 2, mRNA. (I) | KCTD2 | 92 | |
| 4760543 | NM_153719 | nucleoporin 62 kDa (NUP62), transcript variant 1, mRNA. (A) | NUP62 | 93 | |
| 7150564 | NM_003171 | suppressor of var1, 3-like 1 (S. cerevisiae) (SUPV3L1), mRNA. (S) | SUPV3L1 | 94 | |
| 5820475 | NM_002690 | polymerase (DNA directed), beta (POLB), mRNA. (S) | POLB | 95 | |
| 870563 | NM_014710 | G protein-coupled receptor associated sorting protein 1, mRNA. (S) | GPRASP1 | 96 | |
| 4640202 | AW962976 | EST375049 MAGE resequences, MAGH cDNA, mRNA sequence (S) | NaN | 97 | |
| 4250332 | XM_932676 | PREDICTED: similar to Gamma-glutamyltranspeptidase 1 precursor (Gamma- | LOC645367 | 98 | |

TABLE V-continued

| Spot ID | Accession No. | GENE NAME | Symbol | Rank | Fold Chg |
|---|---|---|---|---|---|
| | | glutamyltransferase 1) (CD224 antigen), transcript variant 3 (LOC645367), mRNA. (I) | | | |
| 2570017 | NM_023034 | Wolf-Hirschhorn syndrome candidate 1-like 1 (WHSC1L1), transcript variant long, mRNA. (I) | WHSC1L1 | 99 | |
| 3390458 | NM_002243 | potassium inwardly-rectifying channel, subfamily J, member 15 (KCNJ15), transcript variant 2, mRNA. (A) | KCNJ15 | 100 | |
| 5360053 | XM_926644 | PREDICTED: similar to Thyroid hormone receptor-associated protein complex 240 kDa component (Trap240) (Thyroid hormone receptor associated protein 1) (Vitamin D3 receptor-interacting protein complex component DRIP250) (DRIP 250) (Activator-recruited cofactor . . . (LOC643298), mRNA. (S) | LOC643298 | 101 | |
| 6760653 | XM_935750 | PREDICTED: similar to ETS domain protein Elk-1 (LOC641976), mRNA. (S) | LOC641976 | 102 | |
| 3800615 | NM_080549 | protein tyrosine phosphatase, non-receptor type 6 (PTPN6), transcript variant 3, mRNA. (I) | PTPN6 | 103 | |
| 5310452 | NM_153645 | nucleoporin 50 kDa (NUP50), transcript variant 3, mRNA. (A) | NUP50 | 104 | |
| 3850288 | XM_934211 | PREDICTED: similar to Ribosome biogenesis protein BMS1 homolog, transcript variant 2 (LOC653471), mRNA. (I) | LOC653471 | 105 | |
| 7560538 | NM_153209 | kinesin family member 19 (KIF19), mRNA. (S) | KIF19 | 106 | |
| 6250338 | NM_152371 | chromosome 1 open reading frame 93 (C1orf93), mRNA. (S) | C1orf93 | 107 | |
| 3360382 | NM_001625 | adenylate kinase 2 (AK2), transcript variant AK2A, mRNA. (A) | AK2 | 108 | |
| 6960564 | NM_030934 | chromosome 1 open reading frame 25 (C1orf25), mRNA. (S) | C1orf25 | 109 | |
| 1820131 | XM_945571 | PREDICTED: ankyrin repeat domain 13 family, member D, transcript variant 7 (ANKRD13D), mRNA. (I) | ANKRD13D | 110 | |
| 3850255 | NM_001238 | cyclin E1 (CCNE1), transcript variant 1, mRNA. (A) | CCNE1 | 111 | |
| 990523 | NM_006799 | protease, serine, 21 (testisin) (PRSS21), transcript variant 1, mRNA. (A) | PRSS21 | 112 | |
| 4280577 | NM_006749 | solute carrier family 20 (phosphate transporter), member 2, mRNA. (S) | SLC20A2 | 113 | |
| 7160368 | BC039681 | *Homo sapiens*, clone IMAGE: 5218705, mRNA (S) | NaN | 114 | |
| 6020500 | NM_024923 | nucleoporin 210 kDa (NUP210), mRNA. (S) | NUP210 | 115 | |
| 2360253 | NM_007041 | arginyltransferase 1 (ATE1), transcript variant 2, mRNA. (I) | ATE1 | 116 | |
| 160372 | NM_006761 | tyrosine 3-monooxygenase/tryptophan 5-monooxygenase activation protein, epsilon polypeptide (YWHAE), mRNA. (I) | YWHAE | 117 | |
| 3370170 | BX093763 | BX093763 Soares_fetal_heart_NbHH19W cDNA clone | NaN | 118 | |

TABLE V-continued

| Spot ID | Accession No. | GENE NAME | Symbol | Rank | Fold Chg |
|---|---|---|---|---|---|
| 60546 | AK057981 | IMAGp998N10870, mRNA sequence (S) cDNA FLJ25252 fis, clone STM03814 (S) | NaN | 119 | |
| 1710411 | XM_374029 | PREDICTED: hypothetical LOC389089 (LOC389089), mRNA (S) | NaN | 120 | |
| 6900315 | NM_017958 | pleckstrin homology domain containing, family B (evectins) member 2 (PLEKHB2), transcript variant 2, mRNA. (I) | PLEKHB2 | 121 | |
| 1240603 | NM_000887 | integrin, alpha X (complement component 3 receptor 4 subunit), mRNA(I) | ITGAX | 122 | |
| 60707 | NM_001119 | adducin 1 (alpha) (ADD1), transcript variant 1, mRNA. (A) | ADD1 | 123 | |
| 7160707 | NM_198285 | hypothetical protein LOC349136 (LOC349136), mRNA. (S) | LOC349136 | 124 | |
| 2970332 | NM_006328 | RNA binding motif protein 14 (RBM14), mRNA. (S) | RBM14 | 125 | |
| 2760433 | NM_173564 | hypothetical protein FLJ37538 (FLJ37538), mRNA. (S) | FLJ37538 | 126 | |
| 580041 | NM_001252 | tumor necrosis factor (ligand) superfamily, member 7, mRNA. (S) | TNFSF7 | 127 | |
| 4120133 | NM_022827 | spermatogenesis associated 20 (SPATA20), mRNA. (S) | SPATA20 | 128 | |
| 6560647 | NM_018696 | elaC homolog 1 (*E. coli*) (ELAC1), mRNA. (S) | ELAC1 | 129 | |
| 4180195 | NM_001001520 | hepatoma-derived growth factor-related protein 2 (HDGF2), transcript variant 1, mRNA. (A) | HDGF2 | 130 | |
| 6650020 | NM_001124 | adrenomedullin (ADM), mRNA. (S) | ADM | 131 | |
| 2750364 | NM_020847 | trinucleotide repeat containing 6A, transcript variant 2, mRNA. (I) | TNRC6A | 132 | |
| 1850682 | NM_015530 | golgi reassembly stacking protein 2, 55 kDa (GORASP2), mRNA. (S) | GORASP2 | 133 | |
| 50414 | NM_006973 | zinc finger protein 32 (KOX 30) (ZNF32), transcript variant 1, mRNA. (A) | ZNF32 | 134 | |
| 7200373 | NM_194310 | hypothetical protein LOC284837 (LOC284837), mRNA. (S) | LOC284837 | 135 | |
| 3940215 | NM_015453 | THUMP domain containing 3 (THUMPD3), mRNA. (S) | THUMPD3 | 136 | |

TABLE VI

| Rank | Illumina SpotID | Acc No. | Name | Symbol | p-value | POST/PRE fold chg |
|---|---|---|---|---|---|---|
| 1 | 3370291 | NM_024514 | Cytochrome P450, family 2, subfamily R, polypeptide 1 | CYP2R1 | 0.00000 | −1.39 |
| 2 | 6660437 | NM_006111 | Acetyl-Coenzyme A acyltransferase 2 | MYO5B | 0.00001 | −1.34 |
| 3 | 6380402 | NM_080915 | deoxyguanosine kinase (DGUOK), nuclear gene encoding mitochondrial protein, transcript variant 5, mRNA. (I) | DGUOK | 0.00000 | −1.82 |
| 4 | 1990500 | NM_003746 | Dynein, light chain, LC8-type 1 | DYNLL1 | 0.00002 | 1.38 |

TABLE VI-continued

| Rank | Illumina SpotID | Acc No. | Name | Symbol | p-value | POST/PRE fold chg |
|---|---|---|---|---|---|---|
| 5 | 150048 | NM_052873 | Chromosome 14 open reading frame 179 | C14orf179 | 0.00001 | −1.30 |
| 6 | 2230731 | NM_017745 | BCL6 co-repressor | BCOR | 0.00002 | 1.35 |
| 7 | 270070 | BF448693 | 7n93b04.x1 NCI_CGAP_Ov18 cDNA clone IMAGE: 3571927 3, mRNA sequence (S) | NaN | 0.00001 | −1.57 |
| 8 | 6560482 | NM_001280 | Cold inducible RNA binding protein | CIRBP | 0.00000 | −1.35 |
| 9 | 2970332 | NM_006328 | RNA binding motif Protein 14 | RBM14 | 0.00006 | 1.25 |
| 10 | 3890682 | NM_003975 | SH2 domain protein 2A | SH2D2A | 0.00000 | −1.66 |
| 11 | 6560349 | NM_018425 | Phosphatidylinositol 4-kinase type 2 alpha | PI4K2A | 0.00005 | 1.37 |
| 12 | 1710411 | XM_374029 | PREDICTED: hypothetical LOC389089, mRNA (S) | NaN | 0.00007 | −1.44 |
| 13 | 1660019 | NM_001876 | Carnitine palmitoyltransferase 1A (liver) | CPT1A | 0.00003 | −1.33 |
| 14 | 2680161 | NM_006584 | Chaperonin containing TCP1, subunit 6B (zeta 2) | CCT6B | 0.00002 | −1.58 |
| 15 | 4060270 | BC009563 | *Homo sapiens*, clone IMAGE: 3901628, mRNA (S) | NaN | 0.00006 | −1.38 |
| 16 | 2650152 | NM_020698 | Transmembrane and coiled-coil domain family 3 | TMCC3 | 0.00014 | −1.86 |
| 17 | 20451 | NM_148976 | Proteasome (prosome, macropain) subunit, alpha type, 1 | PSMA1 | 0.00040 | −1.49 |
| 18 | 6220672 | NM_001031711 | Endoplasmic reticulum-golgi intermediate compartment 1 | ERGIC1 | 0.00055 | −1.35 |
| 19 | 6840017 | XM_941287 | PREDICTED: solute carrier family 25 (carnitine/acylcarnitine translocase), member 20 (SLC25A20), mRNA. (A) | SLC25A20 | 0.00159 | −1.24 |
| 20 | 870709 | NM_006133 | Diacylglycerol lipase, alpha | DAGLA | 0.00086 | 1.40 |
| 21 | 5860148 | NM_007320 | RAN binding protein 3 | RANBP3 | 0.00179 | −1.38 |
| 22 | 20707 | NM_207584 | Interferon (alpha, beta and omega) receptor 2 | IFNAR2 | 0.00025 | −1.25 |
| 23 | 5900156 | NM_006082 | Tubulin, alpha 1b | TUBA1B | 0.00268 | 1.13 |
| 24 | 6480170 | NM_001005333 | Melanoma antigen family D, 1 | MAGED1 | 0.00001 | −1.27 |
| 25 | 4010605 | NM_001008739 | Similar to RIKEN cDNA 2310039H08 | LOC441150 | 0.00007 | −1.24 |
| 26 | 7210192 | NM_003123 | Sialophorin (leukosialin, CD43) | SPN | 0.00014 | −1.89 |
| 27 | 4260148 | XM_371534 | PREDICTED: similar to CG10806-PB, isoform B, mRNA. (A) | LOC389000 | 0.00075 | −1.33 |
| 28 | 6560020 | NM_017651 | Abelson helper integration site 1 | AHI1 | 0.00379 | −1.33 |
| 29 | 6480661 | NM_002255 | Killer cell Ig-like receptor, two domains, long cytoplasmic tail, 4 | KIR2DL4 | 0.00117 | −2.02 |
| 30 | 650753 | NM_006712 | Fas-activated serine/threonine kinase | FASTK | 0.00003 | −1.40 |
| 31 | 1230528 | NM_006644 | Heat shock 105 kDa/110 kDa protein 1 | HSPH1 | 0.00006 | 1.47 |
| 32 | 6420086 | NM_001539 | DnaJ (Hsp40) homolog, subfamily A, member 1 | DNAJA1 | 0.00009 | 1.26 |

TABLE VI-continued

| Rank | Illumina SpotID | Acc No. | Name | Symbol | p-value | POST/PRE fold chg |
|---|---|---|---|---|---|---|
| 33 | 4120092 | NM_018244 | Ubiquinol-cytochrome c reductase complex chaperone, CBP3 homolog (yeast) | UQCC | 0.00286 | −1.40 |
| 34 | 4250438 | NM_145267 | Chromosome 6 open reading frame 57 | C6orf57 | 0.00188 | −1.15 |
| 35 | 5860477 | NM_005226 | Sphingosine-1-phosphate receptor 3 | S1PR3 | 0.00017 | 1.69 |
| 36 | 5910037 | NM_182757 | Ring finger 144B | RNF144B | 0.00000 | −1.97 |
| 37 | 6020707 | NM_003416 | Zinc finger protein 7 | ZNF7 | 0.00023 | −1.14 |
| 38 | 4260497 | NM_018179 | Activating transcription factor 7 interacting protein | ATF7IP | 0.00092 | 1.40 |
| 39 | 2760068 | NM_005489 | SH2 domain containing 3C | SH2D3C | 0.00007 | 1.34 |
| 40 | 6250056 | NM_152832 | Family with sequence similarity 89, member B | FAM89B | 0.00043 | 1.21 |
| 41 | 6040273 | BX115698 | BX115698 Soares_testis_NHT cDNA clone IMAGp998M211829, mRNA sequence (S) | NaN | 0.00031 | −1.37 |
| 42 | 1990100 | XM_930024 | PREDICTED: hypothetical protein LOC132241, transcript variant 2 (LOC132241), mRNA. (A) | LOC132241 | 0.00005 | −1.21 |
| 43 | 2640066 | NM_001008910 | Serine/threonine kinase 16 | STK16 | 0.00000 | −1.90 |
| 44 | 770605 | NM_145271 | Zinc finger protein 688 | ZNF688 | 0.00000 | −1.58 |
| 45 | 7200356 | NM_001008541 | MAX interactor 1 | MXI1 | 0.00192 | 1.55 |
| 46 | 1690709 | NM_024815 | Nudix (nucleoside diphosphate linked moiety X)-type motif 18 | NUDT18 | 0.00167 | −1.20 |
| 47 | 1300743 | M4_004089 | TSC22 domain family, member 3 | TSC22D3 | 0.00003 | −1.40 |
| 48 | 2100201 | NM_015558 | synovial sarcoma translocation gene on chromosome 18-like 1 (SS18L1), transcript variant 2, mRNA. (A) | SS18L1 | 0.00008 | 1.19 |
| 49 | 1820209 | NM_001659 | ADP-ribosylation factor 3 | ARF3 | 0.00090 | 1.19 |
| 50 | 1780762 | NM_032847 | Chromosome 8 open reading frame 76 | C8orf76 | 0.00037 | −1.15 |

TABLE VII

| # | Rank | ID | Acc No | Gene Name Description | Symbol | p-value | Fold Chg |
|---|---|---|---|---|---|---|---|
| 1 |  | 4880431 | NM_181738 | Peroxiredoxin 2 | PRDX2 | 0.00000 | 1.42 |
| 2 | 16 | 4120187 | NM_005612 | RE1-silencing transcription factor | REST | 0.00034 | 1.40 |
| 3 |  | 4590563 | XM_942240 | PREDICTED: similar to HLA class II histocompatibility antigen, DQ(W1.1) beta chain precursor (DQB1*0501), transcript variant 1 | LOC650557 | 0.00042 | −2.41 |
| 4 |  | 7210129 | NM_178025 | gamma-glutamyltransferase-like 3 (GGTL3), transcript variant 2 | GGTL3 | 0.00018 | 1.35 |
| 5 | 19 | 4810674 | NM_022091 | Activating signal cointegrator 1 complex subunit 3 | ASCC3 | 0.00274 | 1.73 |

TABLE VII-continued

| # | Rank | ID | Acc No | Gene Name Description | Symbol | p-value | Fold Chg |
|---|---|---|---|---|---|---|---|
| 6 |  | 4280722 | NM_005481 | Mediator complex subunit 16 | MED16 | 0.00027 | 1.22 |
| 7 | 23 | 1400541 | NM_033107 | GTP-binding protein 10 (putative) | GTPBP10 | 0.00559 | −1.26 |
| 8 |  | 1190022 | NM_176895 | Phosphatidic acid phosphatase type 2A | PPAP2A | 0.00355 | 1.20 |
| 9 |  | 3060692 | NM_001010935 | RAP1A, member of RAS oncogene family | RAP1A | 0.00018 | −1.35 |
| 10 |  | 2570440 | NM_022128 | Brain and reproductive organ-expressed (TNFRSF1A modulator) | BRE | 0.00282 | 1.10 |
| 11 |  | 4060138 | XM_941904 | PREDICTED: similar to Transcriptional regulator ATRX (X-linked helicase II) (X-linked nuclear protein) (XNP) | LOC652455 | 0.00029 | 1.47 |
| 12 |  | 6180296 | NM_001017969 | KIAA2026 | KIAA2026 | 0.00028 | −1.15 |
| 13 |  | 1430292 | NM_000578 | Solute carrier family 11 (proton-coupled divalent metal ion transporters), member 1 | SLC11A1 | 0.00006 | −1.41 |
| 14 |  | 110112 | NM_005701 | Snurportin 1 | SNUPN | 0.00033 | −1.17 |
| 15 |  | 6330471 | NM_004337 | Oxidative stress induced growth inhibitor family member 2 | OSGIN2 | 0.00204 | −1.09 |
| 16 |  | 5050019 | XM_945607 | PREDICTED: spastic paraplegia 21 (autosomal recessive, Mast syndrome), transcript variant 3 (SPG21), mRNA | SPG21 | 0.02419 | 1.13 |
| 17 | 4 | 1470605 | NM_001031726 | Chromosome 19 open reading frame 12 | C19orf12 | 0.00382 | 1.43 |
| 18 |  | 6620224 | NM_001024662 | Ribosomal protein L6 | RPL6 | 0.00350 | −1.03 |
| 19 |  | 4250133 | NM_005188 | Cas-Br-M (murine) ecotropic retroviral transforming seq. | CBL | 0.00001 | −1.18 |
| 20 | 9 | 6400075 | NM_024589 | Rogdi homolog (*Drosophila*) | ROGDI | 0.00023 | −1.32 |
| 21 |  | 6580491 | NM_001015880 | 3'-phosphoadenosine 5'-phosphosulfate synthase 2 | PAPSS2 | 0.00341 | −1.34 |
| 22 | 8 | 2940370 | NM_017450 | BAI1-associated protein 2 | BAIAP2 | 0.00046 | −1.38 |
| 23 |  | 3360026 | NM_017911 | Family with sequence similarity 118, member A | FAM118A | 0.01598 | 1.94 |
| 24 | 6 | 1430678 | NM_007118 | Triple functional domain (PTPRF interacting) | TRIO | 0.00001 | −1.31 |

For use in the above-noted compositions the PCR primers and probes are preferably designed based upon intron sequences present in the gene(s) to be amplified selected from the gene expression profile. The design of the primer and probe sequences is within the skill of the art once the particular gene target is selected. The particular methods selected for the primer and probe design and the particular primer and probe sequences are not limiting features of these compositions. A ready explanation of primer and probe design techniques available to those of skill in the art is summarized in U.S. Pat. No. 7,081,340, with reference to publicly available tools such as DNA BLAST software, the Repeat Masker program (Baylor College of Medicine), Primer Express (Applied Biosystems); MGB assay-by-design (Applied Biosystems); Primer3 (Steve Rozen and Helen J. Skaletsky (2000) Primer3 on the WWW for general users and for biologist programmers[85] and other publications[86,87,88].

In general, optimal PCR primers and probes used in the compositions described herein are generally 17-30 bases in length, and contain about 20-80%, such as, for example, about 50-60% G+C bases. Melting temperatures of between 50 and 80° C., e.g. about 50 to 70° C. are typically preferred.

In another aspect, a composition for diagnosing lung cancer in a mammalian subject contains a plurality of polynucleotides immobilized on a substrate, wherein the plurality of genomic probes hybridize to three or more gene expression products of three or more informative genes selected from a gene expression profile in the peripheral blood mononuclear cells (PBMC) of the subject, the gene expression profile comprising genes selected from Table I through Table VII. This type of composition relies on recognition of the same gene profiles as described above for the PCR compositions but employs the techniques of a cDNA array. Hybridization of the immobilized polynucleotides in the composition to the gene expression products present in the PBMC of the patient subject is employed to quantitate the expression of the informative genes selected from among the genes identified in Tables I through VII to generate a gene expression profile for the patient, which is then compared to that of a reference sample. As described above, depending upon the identification of the profile (i.e., that of genes of Table I, II, III, IV, V, VI or VII or subsets thereof), this composition enables the diagnosis and prognosis of NSCLC lung cancers. Again, the selection of the polynucleotide sequences, their length and labels used in the composition are routine determinations made by one of skill in the art in view of the teachings of which genes can form the gene expression profiles suitable for the diagnosis and prognosis of lung cancers.

The composition, which can be presented in the format of a microfluidics card, a microarray, a chip or chamber, employs the polynucleotide hybridization techniques described herein. When a sample of PBMC from a selected patent subject is contacted with the hybridization probes in the composition, PCR amplification of targeted informative genes in the gene expression profile from the patient permits detection and quantification of changes in expression in the genes in the gene expression profile from that of a reference gene expression profile. Significant changes in the gene expression of the informative genes in the patient's PBMC from that of the reference gene expression profile correlate with a diagnosis of non-small cell lung cancer (NSCLC).

In yet another aspect, a composition or kit useful in the methods described herein contain a plurality of ligands that bind to three or more gene expression products of three or more informative genes selected from a gene expression profile in the peripheral blood mononuclear cells (PBMC) of the subject. The gene expression profile contains the genes of any of Tables I through VII, as described above for the other compositions. This composition enables detection of the proteins expressed by the genes in the indicated Tables. While preferably the ligands are antibodies to the proteins encoded by the genes in the profile, it would be evident to one of skill in the art that various forms of antibody, e.g., polyclonal, monoclonal, recombinant, chimeric, as well as fragments and components (e.g., CDRs, single chain variable regions, etc.) may be used in place of antibodies. Such ligands may be immobilized on suitable substrates for contact with the subject's PBMC and analyzed in a conventional fashion. In certain embodiments, the ligands are associated with detectable labels. These compositions also enable detection of changes in proteins encoded by the genes in the gene expression profile from those of a reference gene expression profile. Such changes correlate with lung cancer, e.g., NSCLC, or diagnosis of cancer stage or type, or pre/post surgical status and prognosis in a manner similar to that for the PCR and polynucleotide-containing compositions described above.

In yet a further aspect, a useful composition can contain a plurality of gene expression products of three or more informative genes selected from the gene expression profile in the peripheral blood mononuclear cells (PBMC) of the subject immobilized on a substrate for detection or quantification of antibodies to the proteins encoded by the genes of the profiles in the PBMC of a subject. The gene expression profiles include genes selected from any of Tables I through VII, or subsets thereof, such as the 29 gene classifier of Table V (genes ranked 1-29). This type of composition, directed at detecting antibodies to the products of the genes is also useful in identifying and quantitatively detecting changes in expression in the genes in the gene expression profile from that of a reference gene expression profile for the same reasons identified above for the PCR/polynucleotide-containing compositions. As with the other compositions, this type of composition correlates the expression levels of the proteins encoded by the informative genes in the patient's PMBCs with those of a reference control. Significant changes are indicative of a diagnosis of a lung cancer, are useful for monitoring surgical/therapeutic intervention in the disease, and/or for providing a prognosis of same.

For all of the above forms of diagnostic/prognostic compositions, the gene expression profile can, in one embodiment, include at least the first 5 of the informative genes of any of Tables I through VII or subsets thereof. In another embodiment for all of the above forms of diagnostic/prognostic compositions, the gene expression profile can include 10 or more of the informative genes of any of Tables I through VII or subsets thereof. In another embodiment for all of the above forms of diagnostic/prognostic compositions, the gene expression profile can include 15 or more of the informative genes of any of Tables I through VII or subsets thereof. In another embodiment for all of the above forms of diagnostic/prognostic compositions, the gene expression profile can include 24 or more of the informative genes of any of Tables I through III, and V-VII or subsets thereof. In another embodiment for all of the above forms of diagnostic/prognostic compositions, the gene expression profile can include 30 to 50 or more of the informative genes of any of Tables I-III, V and VII or subsets thereof.

These compositions may be used to diagnose lung cancers, such as stage I or stage II NSCLC. Further these compositions are useful to provide a supplemental or original diagnosis in a subject having lung nodules of unknown etiology. The gene expression profiles formed by genes selected from any of Tables I-VII or subsets thereof are distinguishable from an inflammatory gene expression profile. Further, various embodiments of these compositions can utilize reference gene expression profiles including three or more informative genes of any of Tables I-VII or subsets thereof from the PBMC of one or a combination of classes of reference human subjects. Classes of the reference subjects can include a smoker with malignant disease, a smoker with non-malignant disease, a former smoker with non-malignant disease, a healthy non-smoker with no disease, a non-smoker who has chronic obstructive pulmonary disease (COPD), a former smoker with COPD, a subject with a solid lung tumor prior to surgery for removal or same; a subject with a solid lung tumor following surgical removal of the tumor; a subject with a solid lung tumor prior to therapy for same; and a subject with a solid lung tumor during or following therapy for same. Selection of the appropriate class depends upon the use of the composition, i.e., for original diagnosis, for prognosis following therapy or surgery or for specific diagnosis of disease type, e.g., AC vs. LSCC.

IV. Diagnostic Methods Of The Invention

All of the above-described compositions provide a variety of diagnostic tools which permit a blood-based, non-invasive assessment of disease status in a subject. Use of these compositions in diagnostic tests, which may be coupled with other screening tests, such as a chest X-ray or CT scan, increase diagnostic accuracy and/or direct additional testing. In other aspects, the diagnostic compositions and tools described herein permit the prognosis of disease, monitoring response to specific therapies, and regular assessment of the risk of recurrence. The methods and use of the compositions described herein also permit the evaluation of changes in diagnostic signatures present in pre-surgery and post therapy samples and identifies a gene expression profile or signature that reflects tumor presence and may be used to assess the probability of recurrence. The results on pre-post surgery lung cancer identified in the examples below support a similar detectable effect of the tumor on gene expression in patient PBMCs.

Thus, in one aspect, a method is provided for diagnosing lung cancer in a mammalian subject. This method involves identifying a gene expression profile in the peripheral blood mononuclear cells (PBMC) of a mammalian, preferably human, subject. The gene expression profile includes three or more gene expression products of three or more informative genes having increased or decreased expression in lung cancer. The gene expression profiles are formed by selection of three or more informative genes from the genes of any of Tables I-VII or subsets thereof. Comparison of a subject's gene expression profile with a reference gene expression profile permits identification of changes in expression of the informative genes that correlate with a lung cancer (e.g., NSCLC). This method may be performed using any of the compositions described above.

In one embodiment, the method enables the diagnosis of adenocarcinoma specifically. For this purpose, the gene expression profile is desirably selected from the genes of Table II. In another embodiment, the method enables the diagnosis of stage I or II NSCLC. For this purpose, the gene expression profile is desirably formed of three or more genes of Table I or Table V, including the 29 gene classifier.

As described above for the compositions, the gene profiles optionally involve 5, 6, 10, 15, 25, and greater than 30 informative genes from the respective tables, and can utilize any of the diagnostic method formats referred to herein.

As yet another aspect, a method is provided for predicting the likelihood of recurrence of lung cancer in a mammalian subject. This method includes identifying a gene expression profile in the peripheral blood mononuclear cells (PBMC) of the subject after solid tumor resection or chemotherapy. For this purpose, the gene expression profile includes three or more gene expression products of three or more informative genes of Table III or Table VI. In another embodiment, the gene expression products include the top ranked 2 or 4 genes of Table VI. In one embodiment, the gene expression products are those of the top six genes of Table III or VI. In another embodiment, the gene expression products include at least 10 or 15 of the top ranked genes of Table III or VI. Still other combinations of the genes of Table III or VI are useful in forming a gene expression profile for this purpose. The subject's post-surgical or post-therapeutic gene expression profile is compared with said subject's pre-surgical or pre-therapeutic gene expression profile. Significant changes in expression of said informative genes correlate with a decreased likelihood of recurrence. Maintenance of the changed gene profile expression over time is indicative of low recurrence post-surgery or post-therapy. As indicated in the examples below, this change is identifiable in the PBMC of a subject that has a background of smoking and/or has chronic obstructive pulmonary disease (COPD). As stated above, this method may be performed using the diagnostic compositions and general methodologies described elsewhere in this specification.

The diagnostic compositions and methods described herein provide a variety of advantages over current diagnostic methods. Among such advantages are the following. As exemplified herein, subjects with adenocarcinoma or squamous cell carcinoma of the lung, the two most common types of lung cancer, are distinguished from subjects with non-malignant lung diseases including chronic obstructive lung disease (COPD) or granuloma or other benign tumors. These methods and compositions provide a solution to the practical diagnostic problem of whether a patient who presents at a lung clinic with a small nodule has malignant disease. Patients with an intermediate-risk nodule would clearly benefit from a non-invasive test that would move the patient into either a very low-likelihood or a very high-likelihood category of disease risk. An accurate estimate of malignancy based on a genomic profile (i.e. estimating a given patient has a 90% probability of having cancer versus estimating the patient has only a 5% chance of having cancer) would result in fewer surgeries for benign disease, more early stage tumors removed at a curable stage, fewer follow-up CT scans, and reduction of the significant psychological costs of worrying about a nodule. The economic impact would also likely be significant, such as reducing the current estimated cost of additional health care associated with CT screening for lung cancer, i.e., $116,000 per quality adjusted life-year gained. A non-invasive PBMC genomics test that has a sufficient sensitivity and specificity would significantly alter the post-test probability of malignancy and thus, the subsequent clinical care.

A desirable advantage of these methods over existing methods is that they are able to characterize the disease state from a minimally-invasive procedure, i.e., by taking a blood sample. In contrast current practice for classification of cancer tumors from gene expression profiles depends on a tissue sample, usually a sample from a tumor. In the case of very small tumors a biopsy is problematic and clearly if no tumor is known or visible, a sample from it is impossible. No purification of tumor is required, as is the case when tumor samples are analyzed. A recently published method depends on brushing epithelial cells from the lung during bronchoscopy, a method which is also considerably more invasive than taking a blood sample, and applicable only to lung cancers, while the methods described herein are generalizable to any cancer. Blood samples have an additional advantage, which is that the material is easily prepared and stabilized for later analysis, which is important when messenger RNA is to be analyzed.

In one embodiment of the methods described herein is the use of new algorithms for analyzing the gene expression profiles, which are superior for classification to existing algorithms especially in the analysis of noisy or low signal/noise data. When comparing a generalized disease to a generalized non-disease state, the data is likely to be noisy because many different subclasses are being combined in the comparison. This method could be used as an adjunct to existing diagnosis of lung disease at any pulmonary clinic.

V. EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1

Patient Subject and Control Subjects for PBMC Samples

PBMC samples and clinical information were collected from 300 lung cancer patients and 150 controls, including samples from 16 patients collected pre- and post-surgery. Patient subjects and control subjects both have the key risk factor for lung cancer, i.e., smoking, and many of the patient subjects and non-healthy controls (NHCs) have smoking-related diseases such as COPD. The major difference between the 2 classes is the presence of a malignant nodule in the patient class.

A. Patient Subjects

Patient populations useful in providing data for the development of the gene expression profiles described herein include newly diagnosed male and female patients with early stage lung cancer. Inclusion criteria for selection of these patients were patients a representative number of African-American patients (about 15%), Hispanics (5%), and no Pacific Islanders. The age range of the patients was from 50-80 years. They were in moderately good health (ambulatory), although with medical illness. They were excluded if they have had previous cancers, chemotherapy, radiation, or cancer surgery. They must have had a lung cancer diagnosis within preceding 6 months, histologic confirmation, and no systemic therapy, such as chemotherapy, radiation therapy or cancer surgery as biomarker levels may change with therapy. Thus the majority of the cancer patients were early stage (i.e., Stage I and Stage II).

Another group of patients was those cancer patients in which blood was obtained before surgery and then again at a reasonable interval post-surgery (~2-6 months) to ensure that any acute surgical/inflammatory changes have resolved. This allows each patient to serve as his "own control". Inclusion criteria were patients with a diagnosis of Stage I or II lung cancer that is surgically resectable. They were excluded if they have had previous cancers, chemotherapy, radiation, or cancer surgery. Data was collected on 16 pairs of pre vs. post surgery samples that were analyzed on the Illumina platform. These studies show a loss of tumor signature post surgery in 13 of the 16 pairs tested supporting the detection of a tumor-induced signature in the peripheral blood samples monitored.

B. Control Subjects

Rather than using matched healthy controls (non-smokers or "healthy" smokers), the control cohort was derived primarily from matched at-risk pulmonary patients (smokers and ex-smokers) with non-malignant lung disease and patients with benign lung nodules (e.g. granulomas or hamartomas). The control group is referred to here as "non-healthy controls" (NHC). These patients were evaluated at pulmonary clinics, or underwent thoracic surgery for a lung nodule. All samples were collected prior to surgery. Inclusion criteria for controls were patients between 50-80 years old, with a tobacco use of >10 pack years, and a chest X-ray or CT scan within the last six months demonstrating no evidence of lung cancer and no other cancer within preceding 5 years. Control subjects are matched to the patient subjects based on age, race, gender, and smoking status. Thus, the majority of controls were smokers or ex-smokers greater than 50 years of age. Another control group included patients undergoing surgery for lung nodules in which the nodule turns out to be benign. The NHCs are a population that would benefit significantly from regular monitoring due to their increased risk for developing lung cancer.

Example 2

Sample Collection Protocols and Processing

Blood samples were collected in the clinic by the tissue acquisition technician. Blood is collected in two CPT® tubes (Becton-Dickenson). CPT tubes were evacuated blood collection tubes containing FICOLL reagent below a gel insert and an anti-coagulant above the gel. This is a very efficient and easy way to directly isolate PBMC. Blood is collected from the same patients during their 2-6 month follow-up visit in the clinic after surgery. Blood samples were collected in PAXgene tubes from a subset of patients and control subjects. All coded samples, including tissue blocks and blood components (PBMC, serum, and plasma) were stored based on subject identification in marked freezer storage boxes at −80 C.°. Collected samples were processed through a variety of routine steps that have been highly standardized. Samples were processed as batches (usually 20-50 samples) of both cases and controls rather than as individual samples were collected. At every step, they were randomized so that no particular class of patients or controls is processed as a separate group. RNA purification was carried out using TRI-REAGENT (Molecular Research) as recommended. DNA and RNA were extracted from each sample and DNA was archived for future studies. RNA samples were controlled for quality using the Bioanalyzer and only samples with 28S/16S ratios >0.75 were used for further studies. Samples with lower ratios were archived as they were still suitable for PCR validation studies. The same amount (250 ng of total RNA) was amplified (aRNA) using the RNA amplification kit (Ambion). This provided sufficient amplified material (5-10 µg) for multiple repeats of the arrays and for PCR validation studies. All samples were amplified only once.

An alternative sample collection scheme employs the PAXgene Blood RNA System (Preanalytix—a Qiagen/BD company) for stabilizing RNA in whole blood samples. As PAXgene requires no special processing of the blood samples, it permits more ready development of standards for sample collection. To optimize consistent collection of samples collected at multiple sites of a clinical trial, the PAXgene Blood RNA System (Preanalytix—a Qiagen/BD company) integrates the key steps of whole blood collection, nucleic acid stabilization, and RNA purification. It uses standardized BD Vacutainer™ technology which contains a proprietary reagent that immediately stabilizes intracellular RNA for days at room temperature, weeks at 4 C.°, and they can be stored at least a year at minus 80 C.° before purification of the RNA. The PAXgene tubes may be shipped overnight and stored at −80 C.° until use. All tubes remain at room temperature for 2-4 hrs before freezing as this enhances RNA yields. The ability to minimize processing urgency greatly enhances lab efficiency. For more details see http://www.preanalytix.com/RNA.asp.

In many ways, this was the best method for immediately preserving the RNA message populations present at the time of collection. However, the large amount of globin message present in these samples interfered with message determination on microarrays, despite the efforts to surmount this problem. If a PCR assay is employed for the gene expression profiles described herein, the use of PaxGene is preferred, as the globin message does not interfere with PCR assays Example 3

Methods of Processing Data for Gene Expression Profiling

The ILLUMINA BeadChip is a relatively new method of performing multiplex gene analysis. The essential element of BeadChip technology is the attachment of oligonucleotides to silica beads. The beads were then randomly deposited into wells on a substrate (for example, a glass slide). The resultant array was decoded to determine which oligonucleotide-bead combination is in which well. The decoded arrays may be used for a number of applications, including gene expression analysis. These arrays have the same gene coverage as Affymetrix arrays (47,000 probes for 27,000 genes including splice variants) but use 50-mer oligonucleotides rather than 25-mers and thus provide greater specificity.

The data analysis pipeline procedures using Matlab functions, coded PDA and SVM with RFE and SVM-RCE, were routinely and successfully used as evidenced by previous publications and as described herein.

A. Data Pre-Processing and Array Quality Control.

Data were processed as described generally' and expression levels for signal and control probes are exported. A set of negative control probes was used to calculate average background level and to determine signal detection threshold. The probe expression data were normalized using quantile normalization. The data were checked for outliers by calculating an outlier score for each of the samples. First, Spearman correlation coefficients were calculated for every sample pair. Median correlation for each sample (Ms), median correlation for all sample pairs (Mp) and median absolute deviation from Mp (MADp) were calculated. Outlier score (similarly to Z-score) for sample i was then calculated as (Msi−Mp)/MADp. Outlier scores were studied to pick a threshold to mark potential outliers. Usually, the samples with outlier scores of more than 5 were considered as technical outliers. The further identification of outliers is done through multivariate statistics such as principal components (PCA) plots, multi-dimensional scaling, and robust PCA.

In order to reduce the experimental noise, the data is filtered by removing non-informative probes, i.e. probes that were not detected in majority of samples (more than 95%) or probes that do not change at least 1.2 fold between at least two samples. If a sample had replicates, the latest replicate was taken for the analysis.

B. Unsupervised Classification.

Where appropriate, hierarchical clustering was applied using either Euclidean distance or correlation, and multidimensional scaling was used to inspect datasets for evidence of outliers or subclasses. VISDA (53) was utilized for this purpose with good success.

C. Supervised Classification.

Support Vector Machine (SVM) can be applied to gene expression datasets for gene function discovery and classification. SVM has been found to be most efficient at distinguishing the more closely related cases and controls that reside in the margins Primarily SVM-RFE (48, 54) was used to develop gene expression classifiers which distinguish clinically defined classes of patients from clinically defined classes of controls (smokers, non-smokers, COPD, granuloma, etc). SVM-RFE is a SVM based model utilized in the art that removes genes, recursively based on their contribution to the discrimination, between the two classes being analyzed. The lowest scoring genes by coefficient weights were removed and the remaining genes were scored again and the procedure was repeated until only a few genes remained. This method has been used in several studies to perform classification and gene selection tasks. However, choosing appropriate values of the algorithm parameters (penalty parameter, kernel-function, etc.) can often influence performance.

SVM-RCE is a related SVM based model, in that it, like SVM-RFE assesses the relative contributions of the genes to the classifier. SVM-RCE assesses the contributions of groups of correlated genes instead of individual genes. Additionally, although both methods remove the least important genes at each step, SVM-RCE scores and removes clusters of genes, while SVM-RFE scores and removes a single or small numbers of genes at each round of the algorithm.

The SVM-RCE method is briefly described here. Low expressing genes (average expression less than 2× background) were removed, quantile normalization performed, and then "outlier" arrays whose median expression values differ by more than 3 sigma from the median of the dataset were removed. The remaining samples were subject to SVM-RCE using ten repetitions of 10-fold cross-validation of the algorithm. The genes were reduced by t-test (applied on the training set) to an experimentally determined optimal value which produces highest accuracy in the final result. These starting genes were clustered by K-means into clusters of correlated genes whose average size is 3-5 genes. SVM classification scoring was carried out on each cluster using 3-fold resampling repeated 5 times, and the worst scoring clusters eliminated. Accuracy is determined on the surviving pool of genes using the left-out 10% of samples (testing set) and the top-scoring 100 genes were recorded. The procedure was repeated from the clustering step to an end point of 2 clusters. The optimal gene panel was taken to be the minimal number of genes which gives the maximal accuracy starting with the most frequently selected gene. The identity of the individual genes in this panel is not fixed, since the order reflects the number of times a given gene was selected in the top 100 informative genes and this order is subject to some variation.

Using SVM-RCE, the initial assessment of the performance of each individual gene cluster, as a separate feature, allowed for the identification of those clusters that contributed the least to the classification. These were removed from the analysis while those clusters which exhibited relatively better classification performance were removed. Re-clustering of genes after each elimination step was permitted to allow the formation of new, potentially more informative clusters. The most informative gene clusters were retained for additional rounds of assessment until the clusters of genes with the best classification accuracy were identified.

Utilization of the method using gene clusters, rather than individual genes, enhanced the supervised classification accuracy of the same data as compared to the accuracy when either SVM or Penalized Discriminant Analysis (PDA) with recursive feature elimination (SVM-RFE and PDA-RFE) were used to remove genes based on their individual discriminant weights. The method also permitted the arbitrary determination of the number of clusters and cluster size at the onset of the analysis by the investigator and, as the algorithm proceeded, the least informative clusters were progressively removed. The method further provided the top n clusters required to most accurately differentiate the two pre-defined classes. These two methods are further defined in the following examples.

D. Biomarker Selection.

Genes which score highest (by SVM) in discriminating patients from controls were examined for their utility for clinical tests. Factors considered include, higher differences in expression levels between classes, and low variability within classes. When selecting biomarkers for validation an effort was made to select genes with distinct expression profiles to avoid selection of correlated genes (55) and to identify genes with differential expression levels that were robust by alternative techniques including PCR and/or immuno-histochemistry.

E. Validation.

Three methods of validation were considered.

Cross-Validation: To minimize over-fitting within a dataset, K-fold cross-validation (K usually equal to 10) was used, when the dataset is split on K parts randomly and K−1 parts were used for training and 1 for testing. Thus, for K=10 the algorithm was trained on a random selection of 90% of the patients and 90% of the controls and then tested on the remaining 10%. This was repeated until all of the samples have been employed as test subjects and the cumulated classifier makes use of all of the samples, but no sample is tested using a training set of which it is a part. To reduce the randomization impact, K-fold separation was performed M times producing different combinations of patients and controls in each of K folds each time. Therefore, for individual dataset M*K rounds of permuted selection of training and testing sets were used for each set of genes.

Independent Validation: To estimate the reproducibility of the data and the generality of the classifier, one needs to examine the classifier that was built using one dataset and tested using another dataset to estimate the performance of the classifier. To estimate the performance, validation on the second set was performed using the classifier developed with the original dataset.

Resampling (permutation): To demonstrate dependence of the classifier on the disease state, patients and controls from the dataset were chosen at random (permuted) and the classification was repeated. The accuracy of classification using randomized samples was compared to the accuracy of the developed classifier to determine the p value for the classifier, i.e., the possibility that the classifier might have been chosen by chance. In order to test the generality of a classifier developed in this manner, it was used to classify independent sets of samples that were not used in developing the classifier. The cross-validation accuracies of the permuted and original classifier were compared on independent test sets to confirm its validity in classifying new samples.

F. Classifier Performance

Performance of each classifier was estimated by different methods and several performance measurements were used for comparing classifiers between each other. These measurements include accuracy, area under ROC curve, sensitivity, specificity, true positive rate and true negative rate. Based on the required properties of the classification of interest, different performance measurements can be used to pick the optimal classifier, e.g. classifier to use in screening of the whole population would require better specificity to compensate for small (~1%) prevalence of the disease and therefore avoid large number of false positive hits, while a diagnostic classifier of patients in hospital should be more sensitive.

G. Classifier Application

A linear classifier built by SVM for a set of genes based on a training set can be used to assign an SVM-score to any sample. Mathematically, classifier is a set of g+1 coefficients, where g is a number of genes in the set. If $E_1$, $E_g$ are expression values of these genes for a sample, and $C_1, \ldots, C_{g+1}$ are the corresponding coefficients, then the SVM-score for the sample is easily calculated as $C_1E_1 + \ldots + C_gE_g + C_{g+1}$ H. ROC Analysis ROC analysis was performed to estimate each classifier's efficacy that takes into consideration both, sensitivity and specificity. ROC curve is built for a classifier by varying SVM-score cutoff and calculating corresponding sensitivity and specificity. Area under ROC curve (AUC) was calculated to use as the classifier performance measurement. Since random classifier of samples would have AUC of 0.5 and perfect classifier would have AUC of 1.0, the calculated AUC value can be used and reported as percentage expression of the classifier efficacy.

I. Positive and Negative Predictive Values

Calculation of positive predictive values (PPV) and negative predictive values (NPV) take into account not only specificity and sensitivity, but also a prevalence p of the disease:

$$PPV = \frac{sens \cdot p}{sens \cdot p + (1 - spec) \cdot (1 - p)}$$

$$NPV = \frac{spec(1 - p)}{spec(1 - p) + (1 - sens) \cdot p}$$

Thus, PPV is similar to true positive rate and shows a fraction of subjects that actually have disease among positively classified samples, while NPV is similar to true negative rate and shows a fraction of subjects that actually do not have the disease negatively classified samples.

PPV and NPV values were calculated for every possible SVM-score cutoff for various values of prevalence (1%, 5% and 50%). In addition to direct usage of PPV and NPV values this allows identifying an SVM-score cutoff to use for classification in order to achieve specified classifier predictive value.

Example 4

SVM Supervised Classifications (i) SVM-RFE process was applied to a training subset of samples as follows. T-test was performed on genes from the training set to determine the best 1000 genes that separate two classes of samples. For each gene reduction step SVM was run using the remaining number of genes. Coefficients for these genes from the trained classifier were then compared to eliminate genes with the least impact on the discriminant score. Ten percent of the least significant genes were removed and the process was repeated until only 1 gene was left. The performance of classifiers for each number of genes was calculated by using the corresponding classifier on the test set. Each gene received a score that corresponds to the iteration step at which the gene was eliminated. To eliminate over-fitting within a dataset, K-fold cross-validation (K usually equal to 10) was used. The data were split on K parts (folds) and the algorithm was trained on K−1 folds of the case and the control groups, and then tested on the remaining 1 fold. This guaranteed that each sample was employed as a test subject. The random splitting on K-folds was repeated 10 times, resulting in 100 different training-testing subset pairs. Each training-testing data split was analyzed by SVM-RFE separately. A final gene score was then calculated for all genes that were involved in training of at least one classifier. The score was equal to the average gene score across all resampling runs divided by number of elimination iterations. Thus, the hypothetical gene that reaches the maximum elimination iteration step in all of 100 SVM-RFE runs will receive a score of 1, while the gene that was always eliminated at the first step will receive a score of 0. Different numbers of top genes with highest scores were used to calculate performance of the classifier built on these genes. The classifier with the best performance indicates the optimal number of genes to use for the classification.

(ii) The central algorithm of SVM-RCE method was described as a flowchart (in FIG. 3 of reference 1) which consists of three main steps applied on the training part of the data:

Cluster step for clustering the genes; SVM scoring step for computing the Score($X(s_i)$, f, r) of each cluster of genes and RCE step to remove clusters with low score. The SVM-RCE method was performed according to the following:

It was assumed that dataset D has S genes (all of the genes or top n_g genes by t-test) and that the data was partitioned into two parts: one for training (90% of the samples) and the other (10% of the samples) for testing. X denotes a two-class training dataset that consisting of samples and S genes. Score measurement was defined for any list S of genes as the ability to differentiate the two classes of samples by applying linear SVM. The score was calculated by performing a random partition on the training set X of samples into f non-overlapping subsets of equal sizes (f-folds). Linear SVM was trained over f−1 subsets and the remaining subset was used to calculate the performance. This procedure was repeated r times to take into account different possible partitioning.

Score (X(S),f, r) was defined as the average accuracy of the linear SVM over the data X represented by the S genes computed as f-folds cross validation repeated r times. The default values are f=3 and r=5. If the S genes are clustered into sub-clusters of genes $S_1, S_2, \ldots, S_n$ the Score(X($s_i$), f, r) was defined for each sub-cluster while X($s_i$) was the data X represented by the genes of $S_i$. n=initial number of clusters. m=final number of clusters. d=the reduction parameter. While (n≦m) do: 1. Cluster the given genes S into n clusters $S_1, S_2, \ldots, S_n$ using K-means (Cluster step); 2. For each cluster i=1 . . . n calculate its Score(X($s_i$), f, r) (SVM scoring step); 3. Remove the d % clusters with lowest score (RCE step); 4. Merge surviving genes again into one pool S; 5. Decrease n by d %.

The basic approach of the SVM-RCE was to first cluster the gene expression profiles into n clusters, using K-means. A score (Score (X($s_i$), f, r)), was assigned to each of the clusters by linear SVM, indicating its success at separating samples in the classification task. The d % clusters (or d clusters) with the lowest scores were then removed from the analysis. Steps 1 to Step 5 were repeated until the number n of clusters was decreased to m. Let Z denote the testing dataset. At step 4 an SVM classifier was built from the training dataset using the surviving genes S. This classifier was then tested on Z to estimate the performance. See the above-referenced FIG. 3 of (1), the "Test" panel on the right side.

For the current version, the choice of n and m were determined by the investigator. In this implementation, the default value of m was 2, indicating that the method was required to capture the top 2 significant clusters (groups) of genes. However, accuracy was determined after each round of cluster elimination and a higher number of clusters could be more accurate than the final two. The gist-svm package was used for the implementation of SVM-RFE, with linear kernel function (dot product), with default parameters. In gist-svm the SVM employs a two-norm soft margin with C=1 as penalty parameter. The SVM-RCE was coded in MATLAB while the Bioinformatics Toolbox 2.1 release was used for the implementation of linear SVM with two-norm soft margin with C=1 as penalty parameter. The core of PDA-RFE was implemented in C programming language using a JAVA user interface.

In order to ensure a fair comparison and to decrease the computation time, the top 300 (n_g=300) genes were selected by t-test from the training set for all methods. However, the use of t-statistics for reducing the number of onset genes subjected to SVM-RFE was not only efficient, but it also enhanced the performance of the classifier. For all of the results presented, 10% (d=0.1) was used for the gene cluster reduction for SVM-RCE and 10% of the genes with SVM-RFE and PDA-RFE. For SVM-RCE, the experiment was started using 100 (n=100) clusters and ceased when 2 (m=2) clusters remained. 3-fold (f=3) repeated 5 (r=5) times was used in the SVM-RCE method to evaluate the score of each cluster (SVM scoring step in FIG. 3 of reference 1). More stringent evaluation parameters may be utilized by increasing the number of repeated cross-validations, while simultaneous increasing the computational time.

(iii) For evaluating the over-all performance of SVM-RCE and SVM-RFE (and PDA-RFE), 10-fold cross validation (9 fold for training and 1 fold for testing), repeated 10 times, was employed. After each round of feature or cluster reduction, the accuracy was calculated on the hold-out test set. For each sample in the test set, a score assigned by SVM indicated its distance from the discriminate hyper-plane generated from the training samples, where a positive value indicated membership in the positive class and a negative value indicated membership in the negative class. The class label for each test sample was determined by averaging all 10 of its SVM scores and it is based on this value that the sample was classified. This method for calculating the accuracy gave a more accurate measure of the performance, since it captured not only whether a specific sample is positively (+1) or negatively (−1) classified, but how well it is classified into each category, as determined by a score assigned to each individual sample. The score served as a measure of classification confidence. The range of scores provided a confidence interval. Clustering methods are unsupervised techniques where the labels of the samples are not assigned. K-means[67] is a widely used clustering algorithm. It is an iterative method that groups genes with correlated expression profiles into k mutually exclusive clusters. k is a parameter that needs to be determined at the onset. The starting point of the K-means algorithm is to initiate k randomly generated seed clusters. Each gene profile is associated with the cluster with the minimum distance (different metrics could be used to define distance) to its 'centroid'. The centroid of each cluster is then recomputed as the average of all the cluster gene members' profiles. The procedure is repeated until no changes in the centroids, for the various clusters, are detected. Finally, this algorithm aims at minimizing an objective function with k clusters:

$$F(\text{date}; k) = \sum_{j=1}^{k} \sum_{i=1}^{t} \|g_i^j - c_j\|^2$$

where t is number of genes. ps where $\| \|^2$ is the distance measurement between gene $g_i$ profile and the cluster centroid $c_j$. The "correlation" distance measurement was used as a metric for the SVM-RCE approach. The correlation distance between genes $g_r$ and $g_s$ is defined as:

$$d_{rs} = 1 - \frac{(g_r - \bar{g}_r)(g_s - \bar{g}_s)'}{\sqrt{(g_r - \bar{g}_r)(g_r - \bar{g}_r)'} \sqrt{(g_s - \bar{g}_s)(g_s - \bar{g}_s)'}}$$

where $$\bar{g}_r = \frac{1}{t} \sum_j g_{rj} \text{ and } \bar{g}_s = \frac{1}{t} \sum_j g_{sj}$$

K-means is sensitive to the choice of the seed clusters (initial centroids) and different methods for choosing the seed clusters can be considered. At the K-means step, i.e., the cluster step in FIG. 3 of (1), of SVM-RCE, k genes are randomly selected to form the seed clusters and this process is repeated several times (u times) in order to reach the optimal, with the lowest value of the objective function F(data; k).

The SVM-RCE method differs from related classification methods in the art since the SVM-RCE method first groups genes into correlated gene clusters by K-means and then evaluates the contributions of each of those clusters to the classification task by SVM.

Example 5

Use of Support Vector Machine (SVM) Algorithms and Recursive Cluster Elimination (RCE) to Select Significant Genes for Comparative Gene Expression in Lung Cancer In this example, the SVM-RCE algorithm for gene selection and classification was demonstrated using two (2) datasets. As noted above, this novel algorithm combines the K-means algorithm for gene clustering and the machine learning algorithm (SVM) to identify and score (rank) those gene clusters for the purpose of classification and gene cluster ranking. Recursive cluster elimination (RCE) was then applied to iteratively remove those clusters of genes that contribute the least to the classification performance.

This algorithm was performed using the Matlab™ version of the SVM-RCE algorithm which may be downloaded from http://showelab.wistar.upenn.edu under the "Tools->SVM-RCE" tab. In summary, the SVM-RCE algorithm was evaluated in this example using head and neck tumor datasets (I) and (II) set forth below.

For Dataset (I), gene expression profiling was performed on a panel of 18 head and neck (HN) and 10 lung cancer (LC) tumor samples using Affymetrix® U133A arrays, as described in Vachani et al., Accepted Clin. Cancer Res., 2001, which is hereby incorporated by reference. For Dataset (II), gene expression profiling was performed on a panel of 52 patients with either primary lung (21 samples) or primary head and neck (31 samples) carcinomas, using the Affymetrix® HG_U95Av2 high-density oligonucleotide microarray[68].

Three algorithms, i.e., SVM-RCE, PDA-RFE and SVM-RFE, were used to iteratively reduce the number of genes from the starting value in these datasets (I) and (II) using intermediate classification accuracy as a metric. In summary, the accuracy of the SVM-RCE algorithm at the final 2 gene clusters, and two intermediate levels, usually 8 and 32 clusters, which correspond to 8 genes, 32 genes and 102 genes, respectively, was determined. For the SVM-RFE and PDA-RFE algorithms, the accuracy for comparable numbers of genes was also determined. See, Table VIII.

TABLE VIII

| Algorithm | Head & Neck vs. Lung Tumors (I) | | | Head & Neck vs. Lung Tumors (II) | | |
|---|---|---|---|---|---|---|
| | # clusters (#c) | # genes (# g) | accuracy (ACC) (%) | # clusters (#c) | # genes (# g) | accuracy (ACC) (%) |
| SVM-RCE | 2 | 8 | 100 | 2 | 9 | 100 |
| | 8 | 32 | 100 | 6 | 32 | 100 |
| | 28 | 103 | 100 | 25 | 103 | 100 |
| SVM-RFE | | 8 | 92 | | 8 | 98 |
| | | 32 | 90 | | 32 | 98 |
| | | 102 | 90 | | 102 | 98 |
| PDA-RFE | | 8 | 89 | | 8 | 70 |
| | | 31 | 96 | | 32 | 98 |
| | | 109 | 96 | | 102 | 98 |

The results comparing the independent use of the SVM-RCE and SVM-RFE algorithms on dataset (I) illustrated that the SVM-RCE algorithm had an increase in accuracy over in the SVM-RFE algorithm. Specifically, an increase in accuracy of 8%, 10% and 10% with about 8, about 32, and about 103 genes, respectively, was obtained. Similarly, the results using these two algorithms on dataset (II) showed an about 2% increase with the SVM-RCE algorithm, using about 8, about 32, and about 102 of genes (100% ACC). The SVM-RFE algorithm, however, showed an about 98% ACC. These results clearly demonstrate the superiority of the SVM-RCE algorithm over the SVM-RFE algorithm.

It was also noted that the execution time for the SVM-RCE algorithm using the MATLAB code was greater than the execution time for the SVM-RFE algorithm, which uses the C programming language. For example, when the SVM-RCE was applied on a personal computer with a P4-Duo-core 3.0 GHz processor and 2 GB of RAM on the dataset (I), the results were obtained in approximately 9 hours for 100 iterations (10-folds repeated 10 times). The same results were obtained using the SVM-RFE algorithm (with the svm-gist package) in 4 minutes. To determine the reliability of these results, the SVM-RCE algorithm was again performed on dataset (I), while simultaneously tracking the performance at each iteration and over each level of gene clusters. The results obtained using the SVM-RCE algorithm, regardless of the iterations, had a standard deviation of 0.04 to 0.07. The results obtained using the SVM-RFE algorithm had a standard deviation of 0.2 to 0.23. These results show that the SVM-RCE algorithm was more robust and more stable than the SVM-RFE algorithm.

The same superiority of the SVM-RCE algorithm was observed when comparing the SVM-RCE algorithm with the PDA-RFE algorithm. See, published Table 1[1] and FIG. 1 which use hierarchal clustering and multidimensional scaling (MDS) to help illustrate the improved classification accuracy of the SVM-RCE algorithm for dataset (I). The genes selected by the SVM-RCE algorithm clearly separated the two classes while the genes selected by the SVM-RFE algorithm placed one or two samples on the wrong side of the separating margin.

It was also noted that the execution time for the SVM-RCE algorithm using the MATLAB code was greater than the PDA-RFE algorithm, which uses the C programming language.

The convergence of the algorithm to the optimal solution, and to give a more visual illustration of the SVM-RCE algorithm, was also demonstrated. In summary, the mean performance over all of the clusters for each reduction level for dataset (I) was calculated. See, published FIG. 1 in which ACC is the accuracy, TP is the sensitivity, and TN is the specificity of the remaining genes determined on the test set. Avd is the average accuracy of the individual clusters at each level of clusters determined on the test set. The x-axis provides the average number of genes hosted by the clusters.

In summary, 1000 genes were selected by t-test from the training set, distributed into 300 clusters (initial number of clusters (n)=300, final number of clusters (m)=2, the reduction parameter (d)=0.3, n-g=1000) and then recursively decreased to 2 clusters. The mean classification performance on the test set per cluster at each level of reduction (published FIG. 1, line AVG) dramatically improved from about 55% to about 95% as the number of clusters decreased. The average accuracy also increased as low-information clusters were eliminated. These results support the suggestion that less-significant clusters were removed while informative clusters were retained as the RCE algorithm was employed.

The SVM-RCE algorithm was also useful in estimating stability, as evidenced by the results on dataset (I). The stability was estimated by obtaining values of u (u=number of times the process is repeated) of 1, 10, and 100 repetitions and comparing these values to the most informative 20 genes returned from each experiment. About 80% of the genes were common to the three runs, which suggested that the SVM-RCE algorithm results were robust and stable.

In summary, these data illustrate that the SVM-RCE algorithm provides important information that cannot be obtained using algorithms in the art which assess the contributions of each gene individually. Although the initial observations were based on the top 2 clusters needed for separation of datasets with 2 known classes of samples, i.e., datasets (I) and (II), the analysis may be expanded to capture, e.g., the top 4 clusters of genes.

The results suggest that the selection of significant genes for classification, using the SVM-RCE algorithm, was more reliable than the SVM-RFE or PDA-RFE algorithms. The SVM-RFE algorithm uses the weight coefficient, which appears in the SVM formula, to indicate the contribution of each gene to the classifier. The success of the SVM-RCE algorithm suggested that estimates based on the contribution of genes, which shared a similar profile (correlated genes), was important and gave each group of genes the potential to be ranked as a group. Moreover, the genes selected by the SVM-RCE algorithm were guaranteed to be useful to the overall classification since the measurement of retaining or removing genes (cluster of genes) was based on their contribution to the performance of the classifier. The unsupervised clustering used by the SVM-RCE algorithm is also useful in identifying biologically or clinically important sub-clusters of samples.

Example 6

Assay Formats

To provide a biomarker signature that can be used in clinical practice to diagnose lung cancer, a gene expression profile with the smallest number of genes that maintain satisfactory accuracy is provided by the use of three or more of the genes identified in the Table I, II, III or IV. These gene profiles or signatures permit simpler and more practical tests that are easy to use in a standard clinical laboratory. Because the number of discriminating genes is small enough, quantitative real-time PCR platforms are developed using these gene expression profiles.

A. Quantitative RealTime PCR (RT-PCR)

A diagnostic assay as described herein may employ TAQ-MAN® Low Density Arrays (TLDA). The gene expression profiles described herein suggest the number of genes required is compatible with these platforms. RT-PCR has been considered to be the "gold standard" for validating array results. However in building a PCR-based diagnostic, problems of reproducibility increase as the number of genes required for the diagnosis increase and, more critically, if the differences in expression levels are small.

Initially a TAQMAN® Low Density Array microfluidics card designed to assay for 24 genes in duplicate using Multiplexed TAQMAN® assays was used. This particular configuration assays 8 different samples that are loaded in the numbered ports at the top of the card. A profile of 24 genes was tested in duplicate with 8 samples per card. Each sample was assayed in duplicate in wells preloaded with the specific gene assays reducing variability associated with single well assays. The reverse transcription reactions for each of 8 samples were loaded in the wells at the top labeled 1-8. This platform is useful both for validation of array results and for development of a diagnostic platform to be tested on new samples. Using the TLDA cards significantly simplifies array expression validation as well as provides a reasonable alternative to the StaRT PCR and Focused array platforms for classifier validation.

B. StaRT PCR

StaRT PCR (Gene Express) is essentially a competitive PCR with internal standards for both the gene of interest and the housekeeping gene(s). Having internal controls for housekeeping and experimental genes, it has the advantage of providing a known reference in each sample and a direct quantification of message copy numbers rather than relative copy number, as referenced to a standard curve with a reference RNA. This technique is presently the only technology that meets FDA guidelines for Multi-Gene Assay Methods for Pharmacogenomics. The high absolute accuracy of this method is replaced in the methods described herein by the use of multiple genes and internal controls. However, the diagnostic array may be tested against StaRT PCR to compare accuracy and cost.

C. Focused Diagnostic Gene Array

As the diagnostic profiles were developed, the results from Illumina arrays were compared with RT-PCR data from the TLDAs. Either a custom ILLUMINA array or a custom TLDA may be designed for clinical use.

Example 7

Studies Using an Array Diagnostic and PCR Tool to Diagnose Lung Cancer in Samples from Patients with Small, Undiagnosed Lung Nodules The diagnostic utility of the clinical assays described above was validated. The study population consisted of subjects in whom a lung nodule had been identified by either chest X-ray or chest CT scan. This group of patients represented an ideal population for biomarker use for two main reasons. First, the overall risk of lung cancer was relatively high (18-50%)[17] in this group, depending on nodule size (>0.8 cm). Second, there were significant risks and costs associated with the diagnostic evaluation of these patients, which generally involved serial CT scans, PET scans, invasive biopsy procedures, and, in some cases, surgery.

Study subjects were patients with a solitary, non-calcified pulmonary nodule (>0.8 cm and <3 cm in diameter) detected by chest X-ray or chest CT scan. Only subjects without specific symptoms suggestive of malignancy (e.g. hemoptysis, significant weight loss) were included (i.e. asymptomatic patients). Non-specific symptoms (e.g. dyspnea or cough) are fairly common in current or ex-smokers and therefore subjects with these symptoms are included. Patients discovered to have a non-calcified lung nodule were usually evaluated based on the clinical likelihood of malignancy. Thus, all subjects in this cohort were ultimately identified as either a lung cancer case or a control subject based on specific pathologic and clinical criteria discussed above. The case subjects used in this aim were similar to the case subjects described in the examples above.

The control population (subjects with benign nodules) were different from the control population described in the examples above in that only high-risk patients with nodules were included. Controls were confirmed by pathologic analysis or radiographic stability for more than two years.

The data from the quantitative RT-PCR assays or focused gene arrays were evaluated as diagnostic tests. The main analysis estimated the sensitivity and specificity of the gene expression profiles described above. As the sensitivity and specificity depend on the cutoff value of the quantitative RT-PCR value (for a single biomarker) or the linear discriminant score (for an array of biomarkers), a receiver operating characteristics (ROC) analysis was executed that plots the sensitivity and specificity as a function of the cutoff value. The area under the ROC curve was estimated by conventional methods[59].

The positive predictive value (PPV) and the negative predictive value (NPV)—that is, the probability that a subject with a positive test actually has cancer (the PPV) and the probability that a subject with a negative test does not have cancer (the NPV) were estimated. As these quantities depend on the prevalence of cancer in the group being tested, as well as the sensitivity and specificity of the test, these quantities were computed for a range of possible prevalences likely to hold in different clinical populations. Subgroup analysis was performed to determine the effect of race, gender, and smoking status on the accuracy of the discriminant score.

A logistic regression analysis (virtually equivalent to linear discriminant analysis (LDA)) of the target markers was performed, and certain clinical variables were evaluated using the bootstrap approach[60] to correct for over-fitting in the estimation of such indices of prediction as the area under the ROC curve and the Cronbach alpha statistic. Important clinical variables (nodule size, pack-years, years since quitting, age, and gender) were used to create a baseline predictive model. The value of the gene expression biomarkers for predicting lung cancer were evaluated by creating additional models that will incorporate the linear discriminant score. This analysis established the incremental value of the gene expression biomarkers as part of the clinical evaluation of patients with asymptomatic lung nodules.

To determine whether the biomarker is useful as a trigger for change in intervention in a trial, sample size estimates were based on target values for specificity of 0.9 and sensitivity of 0.9. To ensure that confidence intervals for the sensitivity and specificity extend no more than 5% from the estimated values, at least 138 cases and 138 controls were used.

Example 8

Determining Positive (PPV) and Negative (NPV) Predictive Values for the NSCLC vs. NHC Profile Values for the PPV and NPV calculated for the sensitivity and specificity attained testing the combined NSCLC cancers versus NHC samples are shown in Table IX below. Prevalence values suggested by the EDRN Lung Cancer Biomarker Group (LCBG) available at (http://edrn.nci.nih.gov/resources/sample-reference-sets) were adopted for screening purposes. The prevalence value is 0.01 for an at-risk population age>50 and a smoking status>30 pack-years, and 0.05 for an individual exhibiting an abnormal CT scan, with a non-calcified nodule between 0.5 and 3 cm. These PPV and NPV values were compared to the values considered to be useful for additional study by the LCBG, and to the values determined from a recent study using an 80-gene profile obtained from bronchial brushings, assuming the same prevalence. The 15 gene classifier (see Table IV, col. NSCLC/NHC) already exceeds the performance suggested by LCBG for a good biomarker candidate, and also exceeded that of the most recently published lung cancer biomarker specificity.

TABLE IX

Positive and Negative Predictive Values for 15 gene NSCLC vs. NHC Profile

| Subject | Sensitivity | Specificity | Prevalence | PPV | NPV |
|---|---|---|---|---|---|
| 80 gene classifier (Spira et al, 51) | 0.83 | 0.76 | 1% | 0.034 | 0.998 |
| | | | 5% | 0.154 | 0.988 |
| LCGB proposed biomarker | 0.80 | 0.70 | 1% | 0.026 | 0.997 |
| | | | 5% | 0.123 | 0.985 |
| NSCLC vs. NHC 15 gene classifier | 0.86 | 0.79 | 1% | 0.040 | 0.998 |
| | | | 5% | 0.177 | 0.991 |

Example 9

Power Calculations

In order to estimate the number of samples required to achieve a specified accuracy from classification, the method outlined by Mukherjee[52] was used. The estimation was done by building an empirical learning curve that expressed classification error rate e as a function of training set size n, according to: $e(n)=an^{-\alpha}+b$ where a, $\alpha$, b are to be found by fitting the curve to the observed error rates when using a range of training set sizes drawn from a preliminary dataset. The preliminary dataset in this case consisted of 78 NSCLC of mixed cell types and 52 NHC samples, resulting in 130 samples available for power calculations. This was the most difficult classification set. Error rates were recorded taking training subsets of sizes 25, 32, 38, 45, 51, 58, 64, 70 and 77 samples (corresponds to approximately from 20% to 60% of samples) conserving original proportion of NSCLC and NHC cases.

SVM was run 50 times for each training set size using random samples each time classifying samples using the 500 best genes selected by t-test between cases and controls. Average error rates, along with 25% and 75% percentiles for each training set size were used to fit the learning curve. The error rate for this classifier built using 117 (90%) samples as training set is observed on the ROC curve with an AUC of 0.867 (not shown). The accuracy of 83% (error of 17%) lies on the calculated curve (not shown). Actual error rate was 0.17 observed for the maximum training size available from preliminary data. Error rate approximations of 25% and 75% were detected in one set (data not shown).

Example 10

Classification of Early Stage Lung Adenocarcinoma (AC) and Lung Squamous Cell Carcinoma (LSCC) from PBMC Using cDNA Arrays To determine whether it was possible to detect a gene expression signature in the peripheral blood that can be correlated with early NSCLC, samples from AC and LSCC patients were used since these represent about 85% of all NSCLC. Less common forms of NSCLC (e.g. large cell carcinoma) may also be detected by a classifier built on the more common NSCLC types.

Processing of all samples for RNA purification was carried out under standardized conditions.

The inventors generated a classifier by obtaining PBMC RNA from sets of "non-healthy" control patients (NHC) and patients with various types and stages of NSCLC and performing microarray analysis using a cDNA platform, i.e., nylon cDNA arrays manufactured at the Wistar Genomics Core.

The analysis was carried out using Support Vector Machines with Recursive Feature Elimination (SVM-RFE), as described in Examples 4 and 5 and in other publications[48]. In some cases, Support Vector Machines with Recursive Cluster Elimination (SVM-RCE) algorithm (International Patent Application Publication No WO 2004/105573) was used. Initial attempts to classify patients from controls from PBMC using SVM-RFE resulted in error rates for some of the comparisons, in particular all cancer vs. NHC, too high to be useful (average accuracy about 70%). To address the low signal/noise ratio, a new algorithm SVM-RCE was developed which clusters genes (by K-means clustering) into groups whose differential expression is correlated, and recursively eliminates the least informative clusters instead of individual genes. This results in the final selection of groups of genes whose differential expression changes together. On 6 published datasets[1], this method was shown to be more accurate at classification than SVM-RFE or penalized discriminant analysis (PDA-RFE), and in some cases also results in biologically meaningful clustering of samples. It is most useful for data with low signal/noise or high variance since using gene clusters as variables minimizes the effects of both these aspects of the data.

Whether SVM-RFE or SVM-RCE was applied, in order to eliminate over-fitting within a dataset, M-fold cross-validation (with M equal to 10) was used. The algorithm was trained on M−1 folds of the case and the control group, and then tested on the remaining 1 fold. This guarantees that each sample is employed as a test subject. The average score for each patient was calculated as well as the average score for each gene. The least informative gene(s) were eliminated, and the process repeated. Tables XA and XB show the classification accuracy and the sensitivity (true positive rate) and specificity (true negatives rate) versus the number of genes used for classification. The analytical approaches are described in detail above.

Data for the 208 patients and controls listed in Table XA are shown in Table XB. This data were processed in 3 different "batches" of arrays called sets 3, 4, and 5. As described in Table XA, samples were grouped as early stage adenocarcinomas (AC T1T2), late stage adenocarcinomas (AC T3T4), early stage squamous cell lung cancer (LSCC T1T2) and the non-healthy controls (NHCs). Both cases and controls were usually older smokers or ex-smokers.

Second, although the classification of early stage NSCLCs was more difficult, quite good accuracy could be achieved comparing either the ACs vs. NHCs or LSCCs vs. NHCs alone and for a combined AC+LSCC classifier (Table XB—upper 3 lines). The AC+LSCC comparison to NHCs initially required 287 genes to classify combined early stage samples with 80% accuracy NHCs (line 1). However these results suggested it would be possible to develop a more general classifier that would detect either ACs or LSCCs. When the ACs and LSCCs were segregated and classified separately, 160 genes were initially required to distinguish early ACs from the NHCs with 85% accuracy and only 56 genes to identify the LSCC at the same accuracy. The comparison between the early ACs and LSCCs samples was then found to require only 21 genes for the discrimination, confirming the inventors' previous observations of significant differences between these 2 NSCLC cell types. Ultimately, as shown in Table IV, col. "AC/NHC", a gene profile of 15 genes can distinguish AC from other forms of NSCLC. Further analysis is anticipated to demonstrate that as few as 6 genes are necessary for this profile, as with the pre/post surgery profile formed by the top 6 genes of Table IV, col. Pre/Post.

TABLE XA

Summary of Samples Analyzed on cDNA Arrays

| | |
|---|---|
| AC T1T2 | 59 |
| AC T3T4 | 18 |
| LSCC T1T2 | 36 |
| LSCC T3T4 | 12 |
| NHC | 95 |

TABLE XB

| Sample Classes Compared | # Genes Req'd for Classif'n/# clusters | Accuracy of Classif'n | Sensitivity | Specificity |
|---|---|---|---|---|
| [1]AC + LSCC T1T2 vs. NHC | 287/22 | 0.8 | 0.82 | 0.78 |
| [1]AC T1T2 vs. NHC | 160/11 | 0.85 | 0.83 | 0.85 |
| [2]LSCC T1T2 vs. NHC | 105 | 0.87 | 0.72 | 0.93 |
| [2]LSCC T1T2 vs. NHC | 56/2 | 0.85 | 0.90 | 0.84 |
| [2]AC T1T2 vs. LSCC T1T2 | 21 | 0.88 | 0.92 | 0.81 |
| [2]AC T1T2 vs. LSCC T1T2 | 3 | 0.85 | 0.86 | 0.83 |
| AC T1T2 vs. AC T3T4 | 10 | 0.92 | 0.98 | 0.72 |
| [1]AC T3T4 vs. NHC | 15/2 | 0.88 | 0.77 | 0.94 |

[1]SVM-RCE was used for these analyses.
[2]Two accuracies were reported where a small decrease in accuracy results from a large decrease in the number of genes Since the differences in gene expression detected between cases and controls could be caused by a change in some fraction of the PBMC population, a small flow cytometry study comparing PBMC fractions from 14 NHC lymphocytes to lymphocytes from 14 patients with AC, 15 patients with LSCC, and 6 other NSCLC was performed. In agreement with recent findings[49] for patients with malignant melanoma, there was no statistically significant difference in proportions of CD4 or CD8 T-Cells, B-cells, NK-Cells or monocytes between cases and controls.

Example 11

Classification of Early Stage (T1/T2) NSCLCs from NHCs on Illumina Q-PCR Arrays cDNA array results required 287 genes to distinguish the combined classes of NSCLC samples from the NHCs (see Table XB-line 1, above). The Illumina data however permitted development of a more accurate and global classifier for AC/NHC classification with many fewer genes. The Illumina data available for this analysis included 78 NSCLCs (including 51 ACs, 15 LSCCs, 12 unclassified NSCLCs) and 52 NHC samples. The SVM-RFE analysis indicated 15 genes could classify this dataset with an accuracy of 83%. See Table IV above. The SVM scores for the individual patients and controls shown in FIG. 3 were produced from the performance of the 15 gene classifier of Table IV, col. NSCLC/NHC. These results show that a more general classifier can be used to classify the two main NSCLC cell types.

Figure 2:
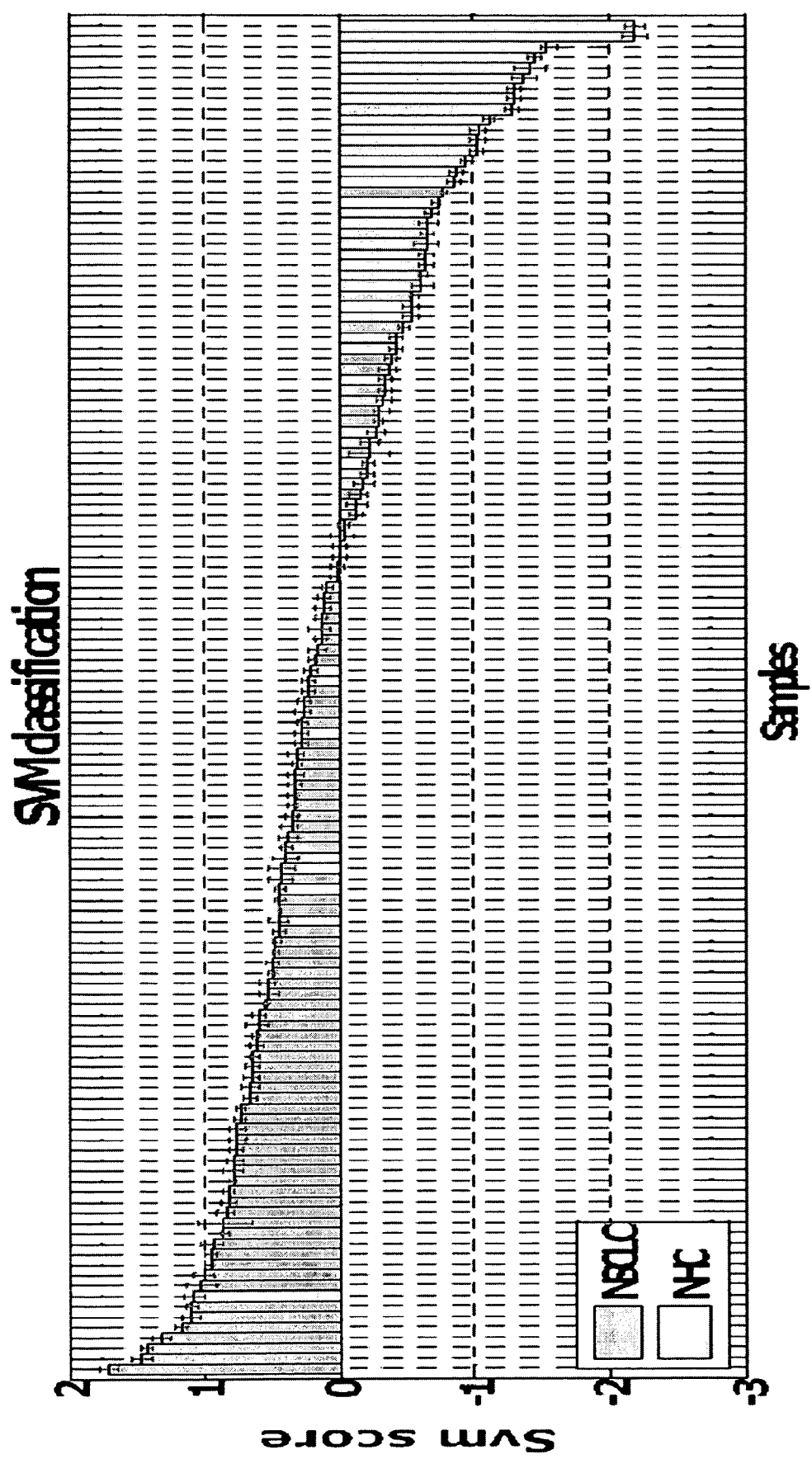
FIG. 2 is a bar graph showing the SVM Classification of combined AC+LSCC (NSCLC; dark bars) and NHC (lighter bars) using the 15 genes selected by SVM-RFE (Table IV, column labeled ALL/NHC). The discriminant scores for the 77 NSCLC samples and 52 NHC samples are shown. Lighter bars with positive scores are misclassified NHC and darker bars with negative scores are misclassified case samples. The ROC curve for the 15 gene classifier produced an AUC of 0.897 (curve not shown).

In one experiment, PBMC from 44 patients with small AC (T1 or T2 size tumors) vs. PBMC from 95 age-, gender- and smoking-matched controls were used. Discriminant scores were generated using nylon arrays and SVM-RCE as described above. The results are provided in FIG. 2. A positive score indicates lung cancer and a negative score indicates no cancer. Each column represents a single patient or control sample. The height of the column is a measure of how well an individual sample is classified. The control samples are on the right and are given a negative score. The patients are on the left. Lighter bars with a positive score are misclassified controls and darker bars with a negative score are misclassified cases. Samples at the margin with scores close to zero should be unclassified. Only the AC T1T2 samples are shown. The samples in the middle where the columns switch from positive to negative or vice/versa are misclassified. Using this classifier employing 15 genes of Table IV, col. AC/NHC, the presence of early stage lung cancer was identified with 85% accuracy.

In still another experiment, forty-four (44) early stage T1T2 AC patient samples were compared to 52 NHC. Genes were filtered by t-test and then SVM-RFE was applied (see Example 4 or 5) and the 15 genes selected by SVM-RFE were used (Table IV, col. AC/NHC). Classification accuracies were analyzed with progressive gene elimination (from 2781 genes to 1) by SVM-RFE[48] (data not shown), measuring True Positives, i.e., the number of patients the classifier correctly assigned a positive SVM-score and True Negatives, i.e., the number of controls the classifier correctly assigned a negative SVM-score. Accuracy was plotted as (TP+TN)/n (n=total number of samples). The favorable s/n and lower variance using the Illumina arrays made the use of the SVM-RCE algorithm unnecessary. SVM-RFE was used for all the Illumina studies as SVM-RCE requires much longer run times then SVM-RFE. The optimal classifier is selected based on the best accuracy with the smallest number of genes. Expression levels of just 15 genes (e.g., the top 15 genes of Table IV, column labeled ALL/NHC, was found to discriminate the early stage T1T2 ACs from the NHCs with an overall accuracy of 85%. This same accuracy was found with cDNA arrays, but 160 genes were initially needed for this degree of separation. These results confirm that the generation of the gene expression profile is not platform specific. The inventor's original discovery of the gene expression profile was affirmed on a second and quite different platform.

Example 12

Changes in Tumor Associated Signatures in PBMC after Removal of the Tumor

To identify a signature that reflects the tumor presence and is useful for the assessing the probability of recurrence, PBMC profiles from the subset of patients with early lung cancers who had blood samples taken before and soon (2-6 months) after "curative" surgery were compared. This minimized background "noise", so that a gene expression signature correlated with the presence of the tumor can be more readily identified. Reversion of the PBMC profile to a "lung cancer" profile thus predicts recurrence.

A. Effect of Presence of the Tumor

Figure 3:
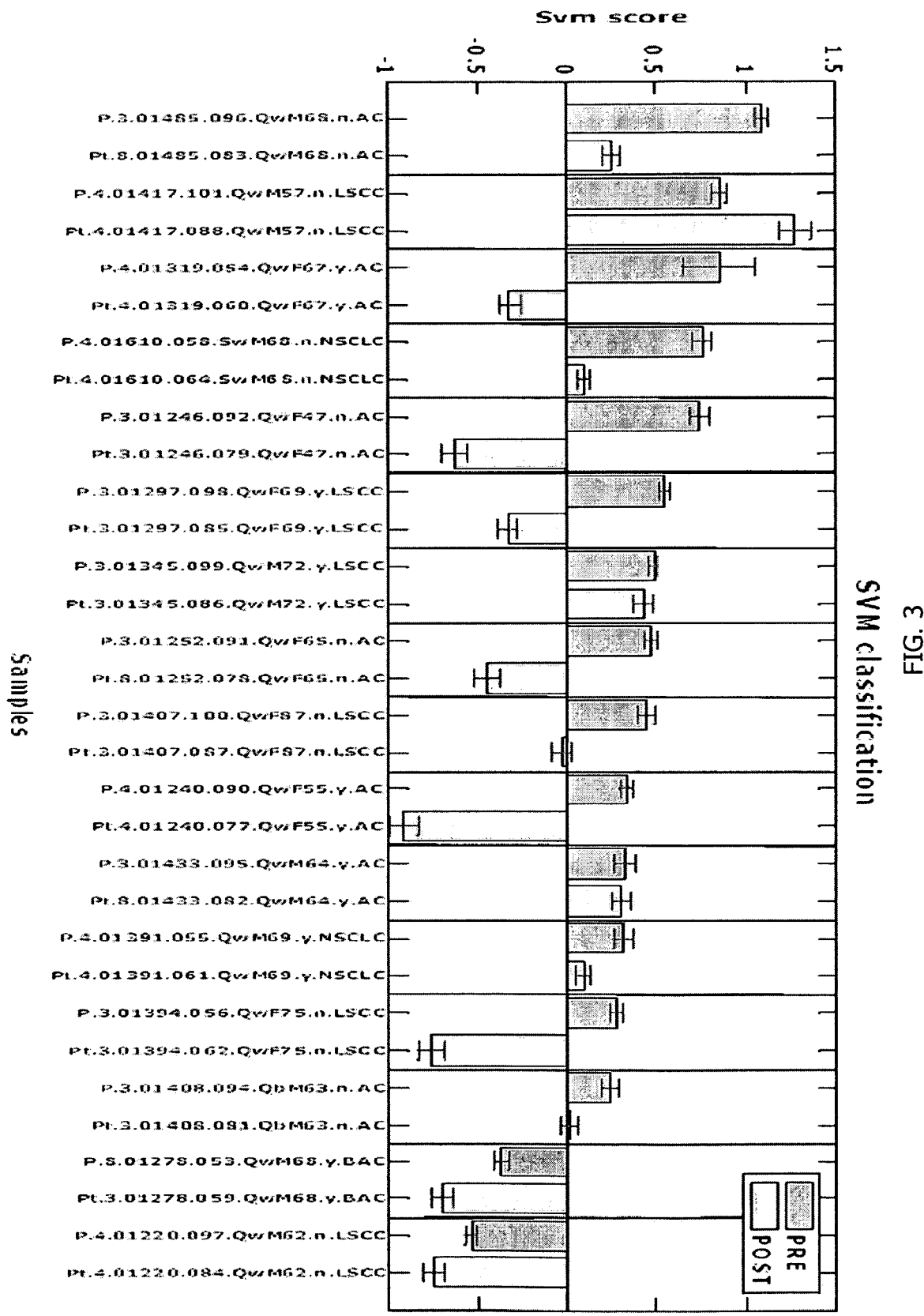
FIG. 3 is a bar graph showing a pairwise comparison of discriminant scores for pre-surgery samples (dark bars) and post-surgery samples (light bars). The 15 genes selected by SVM-RFE (see Table IV, column labeled PRE/POST") were used to assign discriminant scores to the post-surgery samples. These scores are shown with the score for the same patient arranged in pre-post pairs. A negative score indicates this sample is more similar to the NHC samples used to select the 15 gene classifier.
Figure 4:
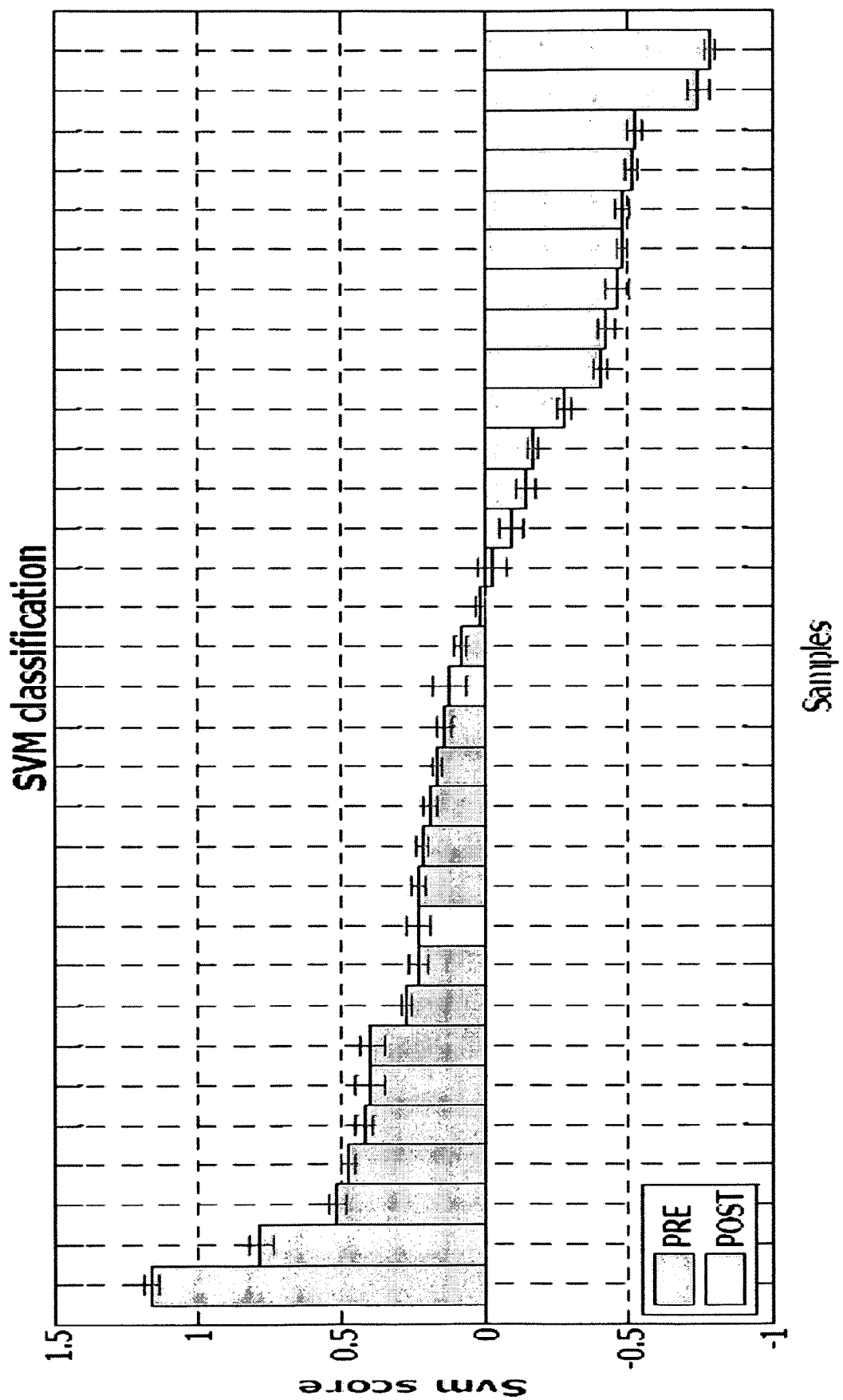
FIG. 4 is a bar graph showing the SVM-RFE analysis of pre-surgery to post-surgery samples. The 16 pre-surgery samples (dark bars) were indicated as the positive class and the 16 post-surgery samples (light bars) as the negative class. SVM-RFE was carried out starting with the top 1,000 genes identified by t-test and then reduced to 1. The classifier built on six genes (the top 6 genes of Table IV, column labeled PRE/POST, namely TSC22D3, CXCR4, DNCL1, RPS3, DDIT4, GZMB) gave an overall accuracy of 93% and these were used to generate the SVM scores. The ROC curve for the 6 gene classifier produced an AUC of 0.96 (curve not shown). A discriminant score was given to each sample (positive is indicative of lung cancer; negative is indicated of no cancer). In all but two samples, the post score is lower than the pre-surgery sample. This data supports the detection of a tumor-related gene expression signature that diminishes after surgery. The extent of those changes reflects the possibility of recurrence.

In order to determine whether the difference in gene expression profiles seen between cases and controls was dependant on the presence of the tumor, the inventors examined how PBMC samples taken from the same NSCLC patient taken pre-surgery and then again ~2-6 months post surgery were classified with the 15 gene classifier that was selected in a comparison of 78 NSCLC patient and 52 NHCs (see FIGS. 3 and 4). The genes selected in this comparison as the pre-post samples were derived from patients with either AC, LSCC or indeterminate NSCLC. The pre-surgery NSCLC samples were included in the analysis shown in FIGS. 3 and 4, but the post-surgery samples were not included. The post surgery samples comprise an independent test set. The rationale was to determine whether the patient samples collected post surgery retained the tumor signature, which in this case is indicated by a positive predictive score, or whether the removal of the tumor would diminish the tumor signature and they would now score more like the controls. The odds of this occurring by chance are <0.01.

Figure 5:
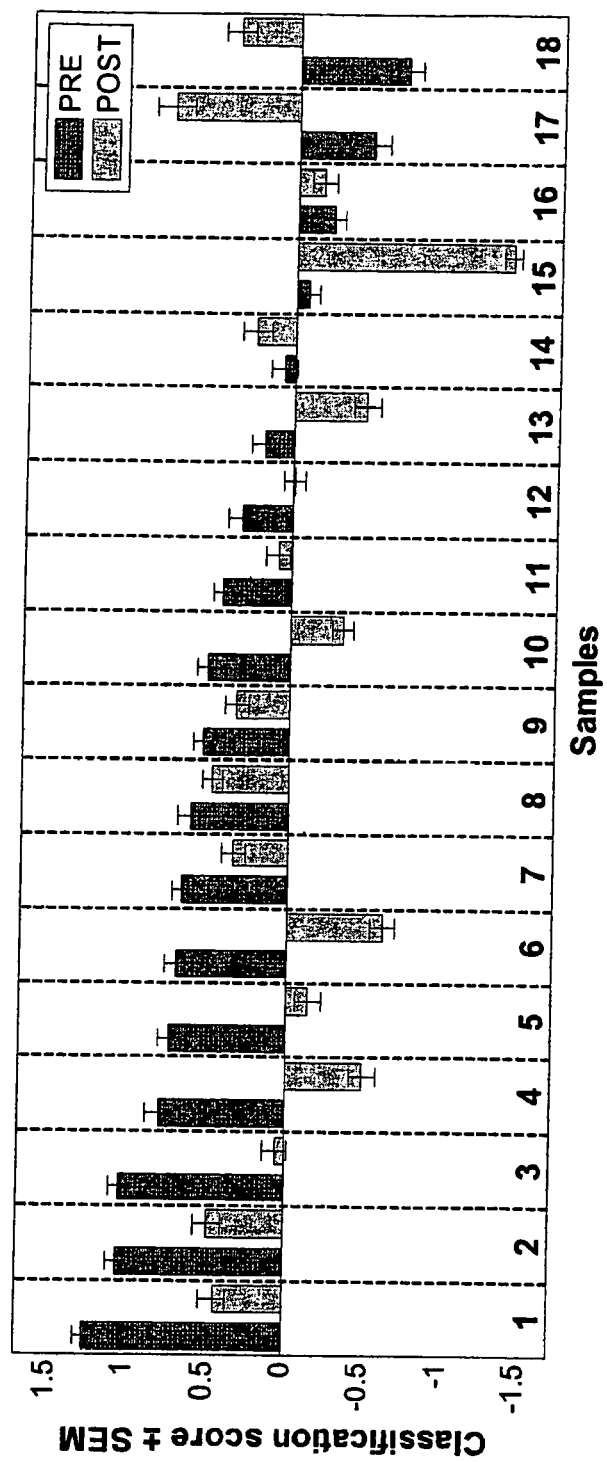
FIG. 5 is a graph showing application of the 29 gene NSCLC classifier to PBMC samples taken pre- and post-surgical resection in 18 patients from the University of Pennsylvania.

13 out of 16 of the patient pairs exhibited a decrease in the tumor predictive score after surgery. Six of the cases have positive pre-surgery scores and a post surgery score that is negative placing them clearly in the control class while 4 additional samples had significant drops in the post-surgery samples bringing them close to zero. Two of the cases had no change in the tumor score after surgery and 1 case had an increase in the tumor score. Two of the cases have a negative pre-surgery score but even in this case it becomes more negative in the post-surgery sample. Additional patient follow up determines the extent to which the post-surgery scores are prognostic for recurrence. The observation that the tumor signature decreased after the removal of the malignancy supported the gene expression profile or signature as a response to the presence of the tumor. See FIGS. 5 and 6.

B. Comparison of Pre- and Post Surgery Samples.

The pre-surgery samples were compared to the post-surgery samples to determine whether the 2 classes of samples could be separated based on the intrinsic differences that were demonstrated in the pairwise analysis in FIG. 3. The 16 pre-surgery samples were compared to the 16 post-surgery samples. SVM-RFE was carried out starting with the top 1,000 genes identified by t-test using 10-fold cross-validation repeated 10 times. Just six genes were determined to distinguish the pre from the post samples with an accuracy of 93%. This 6 gene classifier (the top genes identified in Table IV (col. Pre/Post) was then used to generate the discriminant scores for the pre- and post surgery samples as shown in FIG. 3. The pre-surgery samples (dark shading) are all classified correctly although one sample has a score close to zero. One of the post-surgery samples has a negative score close to zero and 2 are misclassified. This result suggests that a classifier could be developed that might be effective in screening post-surgery patients for recurrence because it would provide the possibility to compare post-surgery scores with the initial pre-surgery score of the same patient over time. Follow-up samples provide a sensitive indicator of recurrence.

In another study, using Illumina array data, genes were selected by comparison of pre-surgery lung cancer samples with NHC smoker controls. Fifty-four (54) genes were used to classify the post-surgery samples. A discriminant score was given to each sample (positive is indicative of lung cancer; negative is indicative of no cancer). In the early analysis (not shown) in all but one comparison, the post score is lower than the pre-surgery sample score, which is adjacent. In three cases, the score of the post surgery sample is negative, classifying those samples with the COPD controls. This data supports the detection of a tumor-related gene expression signature that diminishes after surgery. The extent of those changes reflects the possibility of recurrence.

Given the positive results of the pilot study on 16 paired samples presented here, the utility of this test lies in its application in conjunction with the presence of a lung nodule detected by other procedures such as CT scans. Furthermore, NSCLCs of different cell types (ACs and LSCCs) can be differentiated by a signature designed to make that distinction.

Example 13

Comparison of the Top 15 Genes as Ranked by SVM-RFE for the 3 SVM-RFE Classifiers The 15 top genes by SVM-RFE rank from the 3 Illumina studies are listed in Table IV above. The ranks for each of the genes as assigned in the individual studies by SVM are maintained in Table IV. For the AC/NHC comparison and the comparison of all NSCLC cell types to NHC (ALL/NHC) the 15 genes listed are the genes used to assign the SVM scores shown in FIGS. 2, 4, and 6. The 15 genes for the ALL/NHC comparison were p<3×10$^{-5}$. The 15 AC/NHC genes were p<2×10$^{-4}$ and the Pre/Post genes were p<6×10$^{-3}$. The first 6 genes in the PRE/POST column were used to generate the scores for FIG. 4. The genes shown in bold type are common to either 2 or 3 comparisons. The genes that are not common to the 3 classifiers are not necessarily unique to that comparison but may simply appear at a lower rank position in the extended gene lists. Eight of the top ranked 15 genes for the AC/NHC and the ALL/NHC appear in both lists. Of the top 6 genes used for the PRE/POST classification 3 are listed in either one or both of the other lists. Two probes for HSPA8 are listed. The (A) indicates all HSPA8 isotypes are detected by this probe, (I) indicates a specific isotype (in this case transcript variant 1) is detected by the second HSPA8 probe.

Data on the cDNA array platform reported classification accuracies for comparisons of NSCLCs of different cell types and T stages to NHCs and to each other. The inventors' preliminary data on the Illumina platform was restricted to those patients with early stage AC vs. NHCs or combined NSCLCs vs. NHCs. This was by choice, since ACs are the most common type of NSCLCs and it was important to minimize histological heterogeneity in the initial samples to be analyzed on the new platform. A more general classifier includes a more diversified sample set of cases including LSCCs and indeterminate NSCLCs. Additional samples assayed on the Illumina arrays demonstrate whether the particular subtypes of lung cancer (i.e. AC vs. LSCC) have their own distinct expression patterns as the cDNA arrays suggest and/or whether there is a PBMC signature that can accurately identify all early NSCLCs.

In one embodiment, the ALL/NHC column of Table IV shows the 15 gene profile to identify an NSCLC from controls. In another embodiment, the AC/NHC column of Table IV shows the 15 gene profile to identify an AD. In still another embodiment, PRE/POST column shows the 15 gene profile to identify the efficacy of surgical resection of the tumor and prognosis going forward. As described above, this gene profile has successfully been reduced to only the top 6 genes of that column. It is anticipated that smaller gene selections will be identified for the other two indicated profiles as well. In another embodiment, cell type specific signatures using genes that are present in all three signatures is anticipated to augment the predictive power of these reported scores.

Example 14

29 Gene Expression Signature

To identify a gene expression signature in PBMCs which would accurately distinguish patients with lung cancer from non-cancer controls with similar risk factors (i.e. matched for age, gender, race. smoking history), microarray gene expression profiles in peripheral blood mononuclear cells (PBMC) from patients with NSCLC were compared to a control group with smoking-related non-malignant lung disease. A distinguishing gene signature was found and validated on 2 independent sets of samples not used for gene selection. Gene expression changes were also compared between pre- and post-surgery samples from 18 patients.

A novel 29-gene diagnostic signature (genes ranked 1-29 of Table V) was found which distinguishes individuals with NSCLC from controls with non-malignant lung disease with 91% Sensitivity, 79% Specificity and a ROC AUC of 92%. Accuracies on independent sets of 18 NSCLC samples from the same location and 27 samples from an independent location were 74% and 79%, respectively. The 29 gene signature was significantly reduced after tumor removal in 83% of a subset of 18 patients in whom gene expression was measured before and after surgical resection.

Although both smoking and COPD each affect PBMC gene expression, the additional response to a tumor presence can be identified, allowing the diagnosis of patients with lung cancer from controls with high accuracy. The PBMC signature is particularly useful in the diagnostic algorithm for those patients with a non-calcified lung nodule. The observation that the 29-gene signature diminishes after surgical resection, supports that it is tumor related.

Study Populations: Study participants (Table XVI) for the initial training and validation sets were recruited from the University of Pennsylvania Medical Center (Penn) during the period 2003 through 2007: 91 subjects with a history of tobacco use without lung cancer including 41 subjects that had one non-calcified lung nodule diagnosed as benign after biopsy and 155 patients with newly diagnosed, histopathologically confirmed non-small cell lung cancer. Subjects with any prior history of cancer or cancer treatment except non-melanoma skin cancer were excluded. The study was approved by the Penn Institutional Review Boards. An additional 27 patients and controls were collected at New York University (NYU) Medical Center under IRB approval and are also listed in Table XVI.

TABLE XVI

Summary of demographics

| Category | Number of patients |
| --- | --- |
| All NSCLC vs. NHC experiment samples | |
| Total | 228 |
| Controls | 91 |
| Patients | 137 |
| has COPD | 128 |
| no COPD | 82 |
| unknown COPD | 18 |
| no COPD | 82 |
| Smokers | 34 |
| Quit smoking | 170 |
| Never smokers | 24 |
| Patients from NSCLC vs. NHC experiment | |
| Total | 137 |
| AC | 85 |
| LSCC | 42 |
| NSCLC | 10 |
| has COPD | 63 |
| no COPD | 65 |
| unknown COPD | 9 |
| Stage 1A | 48 |
| Stage 1A + 1B | 75 |
| Stage 4 | 5 |
| Stage ½ | 93 |
| Stage ¾ | 44 |
| Stage 2/3/4 | 62 |
| AC 1A | 30 |
| AC 1 | 48 |
| AC 2/3/4 | 37 |
| LSCC 1A | 16 |
| LSCC 1 | 24 |
| LSCC 2/3/4 | 18 |
| Smokers | 26 |
| Quit smoking | 102 |
| Never smokers | 9 |

TABLE XVI-continued

Summary of demographics

| Category | Number of patients |
|---|---|
| Controls from NSCLC vs. NHC experiment | |
| Total | 91 |
| pure COPD (nothing else) | 38 |
| GI/NM | 41 |
| has COPD | 65 |
| no COPD | 17 |
| unknown COPD | 9 |
| Smokers | 8 |
| Quit smoking | 68 |
| Never smokers | 15 |
| Pre-post pairs | |
| Total | 18 |
| AC | 10 |
| LSCC | 6 |
| NSCLC | 2 |
| NYU samples | |
| Total | 27 |
| AC | 12 |
| NHC | 15 |

PBMC Collection and Processing: Lung cancer patients and patients with non-malignant lung disease had blood collection prior to surgery and/or prior to treatment with chemotherapy. Control patients had blood drawn in conjunction with a clinical visit. Blood samples were drawn in two "CPT" tubes (BD). PBMC were isolated within 90 minutes of blood draw, washed in PBS, transferred into RNA Later (Ambion) and then stored at 4° C. overnight before transfer to −80° C. A subset of patient PBMC's were analyzed by flow cytometry with anti-CD3, CD4, CD8, CD14, CD16, CD19, or CD-56 antibodies or isotype controls (BD Biosciences) and analyzed using Flo-Jo software. Samples from NYU were processed within 2 hours from collection, PBMC were transferred to Trizol (Invitrogen) and stored at −80° C. Extracted RNA was transferred to Wistar for further processing.

Sample Processing: RNA purification of the first set of samples "Penn" was carried out using TriReagent (Molecular Research) as recommended and controlled for quality using the Bioanalyzer. Only samples with 28S/16S ratios >0.75 were used for further studies. A constant amount (400 ng) of total RNA was amplified as recommended by Illumina. The second set of samples "NYU" were DNAse treated before hybridization. Samples were processed as mixed batches of patients and controls and hybridized to the Illumina WG-6v2 human whole genome bead arrays (http://www.illumina.com/pages.ilmn?ID=197)

Array quality control and pre-processing: All arrays were checked for outliers by computing gene-wise between-array median correlation and comparing it with correlation for each array. Non-informative probes were removed if their intensity was low relative to background in majority of samples or if maximum ratio between any 2 samples was not at least 1.2. Arrays were then quantile normalized and background was subtracted from expression values.

Analysis: Classification was performed using a Support Vector Machine with recursive feature elimination (SVM-RFE)[19] using 10-fold cross-validation repeated 10 times. Classification scores for each tested sample were recorded at each reduction step, down to a single gene. Average accuracy for each reduction step was calculated and all the genes at the points of maximal accuracy formed the initial discriminator which then underwent additional reduction to form the final discriminator as described below.

Quantitative RealTime PCR: RT-PCR validation of array results was carried out using the ABI TaqMan System as recommended, in an ABI 7900HT PCR System. Each sample was analyzed in duplicate and samples with CVs between replicates that were more than 0.5 delta Ct were repeated.

The results are reported below:

Clinical and demographic variables of the study samples (case and control) are summarized in Table XVI above for 155 case patients and 91 clinic controls including those with clinically diagnosed benign nodules. The groups were similar in terms of age, race, gender, and smoking history. 84% of the clinical control group and 93% of the NSCLC group were current or previous smokers. These samples were all collected at the University of Pennsylvania Medical Center. An additional 12 patients, and 15 controls were used for external validation. Flow cytometry was performed on 35 cancer cases and 14 controls. There were no significant differences in the percentages of T-cells, CD4 cells, B-cells, monocytes, or NK cells (data not shown). The tumor group had a slightly lower percentage of CD8 cells (18.9%) than the controls (24.5%), which did reach significance.

Gene expression profiles in PBMC samples from 137 patients with NSCLC were compared to 91 controls with non-malignant lung disease (non-healthy controls, NHC) to determine whether consistent differences in gene expression could be detected across the large data set. Gene expression in PBMC were found to identify individuals with a lung cancer, e.g., NSCLC. Over 4500 of 48,000 probes (9%) were significantly changed (two-tail t-test, $p<0.05$, false discovery rate 8%) between cases and controls. For comparison, data reported on lung tumors identified 1649 of 12,600 transcripts (13%) which distinguish adenocarcinomas from normal lung tissue and 1886 (15%) which distinguish squamous cell carcinoma from normal lung at the same significance. The fraction of genes changed in the PBMC of the average NSCLC patient is similar to the reported fraction of genes changed between the tumor and its normal tissue counterpart[20].

A support vector machine with recursive feature elimination (SVM-RFE) and 10-fold cross-validation were next used to find the minimal number of genes which could distinguish the cancer and control groups from their PBMC gene expression. The selection process of the 29 genes by SVM-RFE is described in detail as follows.

Data Pre-Processing/Expression levels and normalization: Samples were processed as mixed batches (total of 12 batches) of patients and controls and hybridized to the Illumina WG-6v2 human whole genome bead arrays. Raw data was processed by the Bead Studio v. 3.0 software. Expression levels were exported for signal and negative control probes. The set of negative control probes was used to calculate average background level for further filtering and background subtraction steps. Average values of the signal probe expression data for the 137 patient (NSCLC) and 91 control (NHC) sample arrays (outliers removed, see below) were used as a base for normalization and all the arrays, including 18 PRE/18 POST samples and NYU samples, were quantile normalized against this base.

Array quality control. After each hybridization batch, gene-wise global correlation was computed as a median Spearman correlation across all pairs of microarrays from all batches using expression levels of all signal probes (>48K). Median absolute deviation of the global correlation was also calculated. Then for each microarray a median spearman correlation against all other arrays was computed. The arrays whose median correlation differs from global correlation more than 8 absolute deviations (threshold was picked empirically) were marked as outliers and were not used for further analysis. 22 outliers were found at various stages, but 11 of these provided valid data on repeated arrays and these were included in the analysis.

Background subtraction. After quantile normalization the average background value (60, as determined for these data) was subtracted from each probe's expression data, which was then floored to one standard deviation of the background (15 for our data), the minimum expression value used in any calculation.

Probe filtering. Based on 137 patient and 91 control sample arrays, non-informative probes were defined to be probes that are not expressed at least 1.5 times background (corresponds to expression value of 30 for background subtracted data) in more than 25% (57) of samples or probes that do not change at least 1.2 fold between at least two samples. The data from all arrays was filtered by removing these non-informative probes, resulting in expression data of 15227 probes for analysis. These procedures result in quantile normalized, outlier removed, background subtracted, non-informative probe filtered data, which were analyzed as follows:

The primary approach involved a classifier for a dataset trained using the SVM algorithm. Recursive Feature Elimination (RFE) strategy was used to reduce number of genes required for the classification. Ten-fold cross-validation was employed to avoid data overfitting and provide unbiased estimation of the classifier accuracy. The trained classifier applied to a sample provided a discriminant score that was used to predict one of two classes (malignant or non-malignant disease, pre or post, etc.) for the sample.

Cross-validation: Ten-fold cross-validation with 10 resamples was used in the classifications of NSCLC vs. NHC (including hold-out and permutation validations) and PRE vs. POST datasets. At each of 10 resample steps, data were randomly split into 10 parts (folds) while retaining the original ratio of the two classes. Each fold was used as a testing subset once while other 9 parts were used as training subsets. This resulted in 10 unique training-testing sets for each resample, and combined with 10 resample steps, 100 unique combinations of 90% samples used for training and 10% samples used for testing. This also ensured that each sample was involved in testing exactly 10 times. The testing was done using classifiers that were not trained on the sample in any way. A discriminant score for each sample was calculated as an average of 10 scores predicted by classifiers that were not trained on a subset including the sample.

RFE: Each of 100 unique training-testing splits provided by cross-validation was used by SVM-RFE independently. From the training subset, 1000 top genes (features) ranked by p-value oft-test between the two classes were retrieved. The classifier was trained using a linear kernel to distinguish between the classes using expression levels of those genes. The classifier was then applied to each sample from the testing subset and discriminant scores were recorded. SVM-RFE then eliminated 10% of the remaining genes that had the smallest absolute coefficients in the classifier's scoring function, i.e. those least important genes that affect the final score the least. The process repeated (50 times) until one gene is left for training.

Performance: 100 cross-validation steps of the SVM-RFE process produced for each sample 10 prediction scores at each feature elimination iteration. A final sample score was computed as an average of these prediction scores for each set of genes tested, from 1000 to 1. Accuracy, sensitivity and specificity of the classification were calculated based on final scores of samples, using $\geq 0$ as the classification threshold, i.e. samples with scores were classified as the positive class, while samples with scores <0—as negative. Classifiers trained at such feature elimination iteration that provided the best accuracy were selected, and a global classifier for all the samples consisted of the genes from each of the 100 optimal classifiers. For example 100 cross-validation steps, each with maximum accuracy at about 8 genes, yielded a global classifier of 136 genes for NSCLC vs. NHC (Table V above) experiment. A ROC curve was built varying classification threshold from maximum between sample scores to minimum.

Classifier minimization: To reduce the number of genes used by classifiers in all cross-validation steps, without retraining and with condition of non-reducing accuracy, unique genes that were involved in classification for a given RFE iteration across all cross-validation steps were ranked by their averaged absolute coefficients in the classifier's scoring function. The least important genes were removed one at a time from all scoring functions. The accuracy was recorded for each removal and minimum number of genes N that provided the same final classification accuracy M was used. The notation "N-gene classifier that has M % accuracy" based on these results was used.

Classifier application: For new samples not used in cross-validation, a classifier selected at the accuracy maximum and then gene-minimized was applied. This classifier was built from 100 sub-classifiers received at each step of the cross-validation for the selected RFE iteration. Final sample score was an average of 100 scores provided by those classifiers. Note, that when applied to a sample that was used in the cross-validation, from 100 sub-classifiers only 10 that were not trained on the sample were used.

137 NSCLC and 91 NHC samples were split into 5 parts. 1 part was used as a hold-out set and 4 parts were used as a dataset that was analyzed using SVM-RFE with 10-fold, 10-resample cross-validation. The final best N-gene classifier was then applied to the hold-out part. Cross-validation and hold-out accuracies were compared. 10 permutation datasets were generated. Labels of 137 NSCLC and 91 NHC were shuffled randomly and the data was analyzed using SVM-RFE with 10-fold, 10-resample cross-validation. The final best accuracy N-gene classifier was selected for each permutation and the accuracy was recorded. Average permutation accuracy across 10 runs was calculated.

Average cross-validation performance of SVM-RFE (figure not shown) indicated that on average, 8 genes were required for best accuracy at each step during 100 cross-validation steps. The 100 steps resulted in the 136 distinct genes reported in Table V above. The 136 genes that provided the best accuracy were further reduced to filter out as many genes as possible without losing accuracy. Polynomial of power 5 was fit to the accuracy to detect the number of genes where the accuracy starts to decline (i.e., at 29 genes). The genes in Table V are ranked in order by their contribution to the final classification score (the most important gene ranking first, etc.). Alternative names and symbols are referenced and the symbol "NaN" indicates that a symbol for the gene is not yet available.

Classification scores were assigned by the 29 gene classifier to 137 NSCLC patients and 91 patients with non-malignant lung disease. A positive score indicated classification as cancer, a negative score as non-malignant disease. Table XI lists the patient ID number, the class of disease (AC-adenocarcinoma, LSCC-lung squamous cell carcinoma, NSCLC-not further characterized, Non-Healthy control samples (NHC) patients with non-malignant lung disease: COPD: only chronic obstructive pulmonary disease, Benign Nodules: (determined by biopsy), Other: various types of lung diseases without defined COPD diagnosis), the classification score of each patient, the standard error of the mean, the diagnosis, and the stage of cancer, if any.

TABLE XI

Individual patient SVM scores from 29-gene NSCLC classifier

| ID | Class | Score | Error | Dx | Stage |
|---|---|---|---|---|---|
| NSCLC.1519 | NSCLC | 1.77 | 0.21 | AC | 3A |
| NSCLC.1138 | NSCLC | 1.65 | 0.07 | LSCC | 3B |
| NSCLC.1471 | NSCLC | 1.64 | 0.32 | NSCLC | 3A |
| NSCLC.1282 | NSCLC | 1.54 | 0.26 | AC | 3B |
| NSCLC.1154 | NSCLC | 1.54 | 0.23 | AC | 3A |
| NSCLC.1222 | NSCLC | 1.51 | 0.24 | AC | 1B |
| NSCLC.1175 | NSCLC | 1.48 | 0.21 | AC | 1A |
| NSCLC.1352 | NSCLC | 1.45 | 0.31 | AC | 1B |
| NSCLC.1600 | NSCLC | 1.40 | 0.29 | NSCLC | 3B |
| NSCLC.1647 | NSCLC | 1.39 | 0.23 | LSCC | 3B |
| NSCLC.1280 | NSCLC | 1.38 | 0.30 | LSCC | 3B |
| NSCLC.1311 | NSCLC | 1.36 | 0.15 | AC | 1A |
| NSCLC.1200 | NSCLC | 1.35 | 0.26 | AC | 3A |
| NSCLC.1602 | NSCLC | 1.35 | 0.22 | LSCC | 1A |
| NSCLC.1192 | NSCLC | 1.34 | 0.19 | LSCC | 1B |
| NSCLC.1177 | NSCLC | 1.32 | 0.11 | AC | 1B |
| NSCLC.1583 | NSCLC | 1.32 | 0.22 | LSCC | 3A |
| NSCLC.1397 | NSCLC | 1.32 | 0.34 | AC | 1A |
| NSCLC.1362 | NSCLC | 1.30 | 0.11 | AC | 3B |
| NSCLC.1403 | NSCLC | 1.30 | 0.18 | AC | 3B |
| NSCLC.1307 | NSCLC | 1.29 | 0.30 | AC | 1A |
| NSCLC.1559 | NSCLC | 1.27 | 0.14 | AC | 3A |
| NSCLC.1589 | NSCLC | 1.26 | 0.19 | AC | 2B |
| NSCLC.1155 | NSCLC | 1.25 | 0.17 | AC | 3A |
| NSCLC.1211 | NSCLC | 1.23 | 0.23 | AC | 1A |
| NSCLC.1631 | NSCLC | 1.23 | 0.18 | AC | 2B |
| NSCLC.1475 | NSCLC | 1.21 | 0.17 | LSCC | 1A |
| NSCLC.1437 | NSCLC | 1.20 | 0.28 | LSCC | 3A |
| NSCLC.1484 | NSCLC | 1.15 | 0.17 | LSCC | 3A |
| NSCLC.1166 | NSCLC | 1.15 | 0.35 | AC | 1B |
| NSCLC.1674 | NSCLC | 1.14 | 0.09 | AC | 3A |
| NSCLC.1454 | NSCLC | 1.13 | 0.19 | LSCC | 2B |
| NSCLC.1316 | NSCLC | 1.12 | 0.28 | AC | 1B |
| NSCLC.1569 | NSCLC | 1.11 | 0.21 | NSCLC | 3A |
| NSCLC.1339 | NSCLC | 1.07 | 0.27 | LSCC | 2B |
| NSCLC.1264 | NSCLC | 1.06 | 0.29 | LSCC | 4 |
| NSCLC.1325 | NSCLC | 1.05 | 0.12 | NSCLC | 3B |
| NSCLC.1632 | NSCLC | 1.05 | 0.15 | AC | 2A |
| NSCLC.1473 | NSCLC | 1.03 | 0.30 | AC | 1B |
| NSCLC.1402 | NSCLC | 1.02 | 0.24 | AC | 4 |
| NSCLC.1557 | NSCLC | 1.01 | 0.23 | NSCLC | 1B |
| NSCLC.1183 | NSCLC | 0.98 | 0.25 | AC | 1A |
| NSCLC.1455 | NSCLC | 0.97 | 0.16 | LSCC | 1A |
| NSCLC.1194 | NSCLC | 0.97 | 0.17 | AC | 4 |
| NSCLC.1193 | NSCLC | 0.96 | 0.20 | AC | 1B |
| NSCLC.1224 | NSCLC | 0.96 | 0.13 | AC | 2A |
| NSCLC.1573 | NSCLC | 0.94 | 0.14 | AC | 3B |
| NSCLC.1375 | NSCLC | 0.94 | 0.25 | NSCLC | 1A |
| NSCLC.1214 | NSCLC | 0.93 | 0.32 | LSCC | 1B |
| NSCLC.1630 | NSCLC | 0.92 | 0.22 | NSCLC | 3A |
| NSCLC.1343 | NSCLC | 0.92 | 0.20 | AC | 3A |
| NSCLC.1561 | NSCLC | 0.91 | 0.21 | LSCC | 2A |
| NSCLC.1435 | NSCLC | 0.89 | 0.25 | AC | 1A |
| NSCLC.1221 | NSCLC | 0.88 | 0.32 | AC | 3A |
| NSCLC.1449 | NSCLC | 0.87 | 0.14 | LSCC | 1A |
| NSCLC.1413 | NSCLC | 0.85 | 0.21 | LSCC | 1B |
| NSCLC.1287 | NSCLC | 0.84 | 0.20 | AC | 1B |
| NSCLC.1387 | NSCLC | 0.84 | 0.21 | AC | 3A |
| NSCLC.1140 | NSCLC | 0.83 | 0.21 | AC | 3B |
| NSCLC.1598 | NSCLC | 0.83 | 0.31 | AC | 1A |
| NSCLC.1415 | NSCLC | 0.78 | 0.20 | AC | 1A |
| NSCLC.1369 | NSCLC | 0.77 | 0.21 | AC | 1B |
| NSCLC.1591 | NSCLC | 0.75 | 0.10 | AC | 1A |
| NSCLC.1469 | NSCLC | 0.75 | 0.25 | AC | 1A |
| NSCLC.1141 | NSCLC | 0.75 | 0.23 | AC | 1B |
| NSCLC.1340 | NSCLC | 0.74 | 0.37 | AC | 1A |
| NSCLC.1178 | NSCLC | 0.73 | 0.13 | LSCC | 3B |
| NSCLC.1604 | NSCLC | 0.73 | 0.21 | AC | 2B |
| NSCLC.1429 | NSCLC | 0.70 | 0.15 | LSCC | 1A |
| NSCLC.1681 | NSCLC | 0.67 | 0.26 | NSCLC | 3B |
| NSCLC.1542 | NSCLC | 0.67 | 0.24 | AC | 1A |

TABLE XI-continued

Individual patient SVM scores from 29-gene NSCLC classifier

| ID | Class | Score | Error | Dx | Stage |
|---|---|---|---|---|---|
| NSCLC.1572 | NSCLC | 0.66 | 0.26 | AC | 1A |
| NSCLC.1143 | NSCLC | 0.66 | 0.31 | AC | 1A |
| NSCLC.1439 | NSCLC | 0.66 | 0.35 | AC | 3B |
| NSCLC.1189 | NSCLC | 0.61 | 0.27 | LSCC | 3A |
| NSCLC.1189 | NSCLC | 0.61 | 0.27 | LSCC | 3A |
| NSCLC.1312 | NSCLC | 0.61 | 0.27 | AC | 2B |
| NSCLC.1323 | NSCLC | 0.61 | 0.32 | AC | 4 |
| NSCLC.1466 | NSCLC | 0.61 | 0.30 | LSCC | 2B |
| NSCLC.1643 | NSCLC | 0.59 | 0.21 | AC | 3B |
| NSCLC.1550 | NSCLC | 0.58 | 0.21 | AC | 2B |
| NSCLC.1423 | NSCLC | 0.55 | 0.26 | LSCC | 1B |
| NSCLC.1468 | NSCLC | 0.54 | 0.19 | LSCC | 1A |
| NSCLC.1167 | NSCLC | 0.54 | 0.31 | AC | 1A |
| NSCLC.1436 | NSCLC | 0.54 | 0.31 | AC | 1A |
| NSCLC.1368 | NSCLC | 0.53 | 0.16 | AC | 1A |
| NSCLC.1158 | NSCLC | 0.52 | 0.41 | AC | 1A |
| NSCLC.1137 | NSCLC | 0.51 | 0.26 | AC | 2B |
| NSCLC.1656 | NSCLC | 0.51 | 0.12 | AC | 3A |
| NSCLC.1592 | NSCLC | 0.50 | 0.20 | LSCC | 1B |
| NSCLC.1489 | NSCLC | 0.48 | 0.29 | AC | 2A |
| NSCLC.1566 | NSCLC | 0.47 | 0.21 | LSCC | 3B |
| NSCLC.1284 | NSCLC | 0.45 | 0.25 | LSCC | 1A |
| NSCLC.1204 | NSCLC | 0.43 | 0.31 | LSCC | 1A |
| NSCLC.1400 | NSCLC | 0.43 | 0.33 | LSCC | 1A |
| NSCLC.1622 | NSCLC | 0.42 | 0.42 | NSCLC | 1A |
| NSCLC.1482 | NSCLC | 0.42 | 0.19 | LSCC | 1A |
| NSCLC.1390 | NSCLC | 0.41 | 0.11 | LSCC | 2B |
| NSCLC.1597 | NSCLC | 0.39 | 0.11 | AC | 3A |
| NSCLC.1388 | NSCLC | 0.36 | 0.27 | NSCLC | 3B |
| NSCLC.1444 | NSCLC | 0.35 | 0.23 | AC | 3A |
| NSCLC.1463 | NSCLC | 0.35 | 0.22 | LSCC | 1A |
| NSCLC.1586 | NSCLC | 0.34 | 0.29 | LSCC | 1A |
| NSCLC.1233 | NSCLC | 0.30 | 0.28 | LSCC | 2A |
| NSCLC.1713 | NSCLC | 0.29 | 0.22 | AC | 3B |
| NSCLC.1344 | NSCLC | 0.29 | 0.28 | AC | 1B |
| NSCLC.1171 | NSCLC | 0.27 | 0.35 | LSCC | 1A |
| NSCLC.1590 | NSCLC | 0.25 | 0.18 | AC | 3A |
| NSCLC.1196 | NSCLC | 0.25 | 0.26 | LSCC | 2B |
| NSCLC.1451 | NSCLC | 0.24 | 0.22 | AC | 1B |
| NSCLC.1709 | NSCLC | 0.24 | 0.23 | LSCC | 3B |
| NSCLC.1560 | NSCLC | 0.23 | 0.30 | AC | 3A |
| NSCLC.1584 | NSCLC | 0.19 | 0.44 | AC | 1A |
| NSCLC.1269 | NSCLC | 0.18 | 0.23 | LSCC | 1A |
| NSCLC.1595 | NSCLC | 0.17 | 0.23 | LSCC | 1B |
| NSCLC.1286 | NSCLC | 0.16 | 0.25 | AC | 1A |
| NSCLC.1202 | NSCLC | 0.14 | 0.31 | AC | 1B |
| NSCLC.1292 | NSCLC | 0.13 | 0.22 | LSCC | 1B |
| NSCLC.1491 | NSCLC | 0.12 | 0.17 | AC | 1B |
| NSCLC.1373 | NSCLC | 0.09 | 0.23 | AC | 1B |
| NSCLC.1303 | NSCLC | 0.09 | 0.20 | LSCC | 1A |
| NSCLC.1614 | NSCLC | 0.08 | 0.28 | LSCC | 1B |
| NSCLC.1337 | NSCLC | 0.05 | 0.31 | AC | 1A |
| NSCLC.1453 | NSCLC | 0.02 | 0.15 | AC | 4 |
| NSCLC.1227 | NSCLC | 0.01 | 0.32 | AC | 1A |
| NSCLC.1216 | NSCLC | −0.01 | 0.38 | AC | 1A |
| NSCLC.1254 | NSCLC | −0.09 | 0.30 | LSCC | 1A |
| NSCLC.1136 | NSCLC | −0.13 | 0.32 | AC | 1A |
| NSCLC.1346 | NSCLC | −0.15 | 0.21 | AC | 2A |
| NSCLC.1445 | NSCLC | −0.32 | 0.35 | AC | 2A |
| NSCLC.1431 | NSCLC | −0.34 | 0.29 | AC | 1A |
| NSCLC.1582 | NSCLC | −0.38 | 0.17 | AC | 1B |
| NSCLC.1427 | NSCLC | −0.43 | 0.24 | AC | 1A |
| NSCLC.1430 | NSCLC | −0.45 | 0.23 | AC | 1A |
| NSCLC.1153 | NSCLC | −0.51 | 0.27 | AC | 1A |
| NSCLC.1262 | NSCLC | −0.51 | 0.29 | AC | 1A |
| NSCLC.1548 | NSCLC | −0.61 | 0.31 | AC | 1B |
| NSCLC.1386 | NSCLC | −0.65 | 0.22 | AC | 1B |
| NHC.1218 | NHC | 1.13 | 0.36 | GI | 0 |
| NHC.1588 | NHC | 0.96 | 0.31 | GI | 0 |
| NHC.1146 | NHC | 0.80 | 0.23 | HAM | 0 |
| NHC.10062 | NHC | 0.77 | 0.33 | COPD | 0 |
| NHC.1554 | NHC | 0.72 | 0.20 | NM | 0 |
| NHC.10027 | NHC | 0.60 | 0.30 | COPD | 0 |
| NHC.1474 | NHC | 0.59 | 0.19 | NM | 0 |
| NHC.1628 | NHC | 0.51 | 0.37 | GI | 0 |
| NHC.10010 | NHC | 0.48 | 0.29 | HTN | 0 |

TABLE XI-continued

Individual patient SVM scores from 29-gene NSCLC classifier

| ID | Class | Score | Error | Dx | Stage |
|---|---|---|---|---|---|
| NHC.1263 | NHC | 0.48 | 0.21 | NM | 0 |
| NHC.1619 | NHC | 0.45 | 0.10 | GI | 0 |
| NHC.1361 | NHC | 0.42 | 0.27 | NM | 0 |
| NHC.1575 | NHC | 0.38 | 0.19 | GI | 0 |
| NHC.1522 | NHC | 0.21 | 0.12 | GI | 0 |
| NHC.1562 | NHC | 0.11 | 0.27 | NM | 0 |
| NHC.10047 | NHC | 0.11 | 0.31 | COPD | 0 |
| NHC.1424 | NHC | 0.04 | 0.21 | GI | 0 |
| NHC.10037 | NHC | 0.02 | 0.32 | COPD | 0 |
| NHC.10063 | NHC | −0.01 | 0.22 | COPD | 0 |
| NHC.1677 | NHC | −0.05 | 0.15 | GI | 0 |
| NHC.10044 | NHC | −0.16 | 0.23 | SARC | 0 |
| NHC.1260 | NHC | −0.16 | 0.25 | NM | 0 |
| NHC.1182 | NHC | −0.23 | 0.38 | PN | 0 |
| NHC.10043 | NHC | −0.25 | 0.31 | COPD | 0 |
| NHC.10064 | NHC | −0.29 | 0.29 | COPD | 0 |
| NHC.1148 | NHC | −0.30 | 0.35 | GI | 0 |
| NHC.1184 | NHC | −0.30 | 0.26 | NM | 0 |
| NHC.1618 | NHC | −0.33 | 0.20 | GI | 0 |
| NHC.10046 | NHC | −0.33 | 0.15 | COPD | 0 |
| NHC.1657 | NHC | −0.37 | 0.25 | SARC | 0 |
| NHC.10034 | NHC | −0.44 | 0.24 | COPD | 0 |
| NHC.10036 | NHC | −0.45 | 0.21 | COPD | 0 |
| NHC.10058 | NHC | −0.47 | 0.23 | COPD | 0 |
| NHC.10054 | NHC | −0.49 | 0.20 | COPD | 0 |
| NHC.10028 | NHC | −0.50 | 0.14 | COPD | 0 |
| NHC.10004 | NHC | −0.52 | 0.32 | PS | 0 |
| NHC.10040 | NHC | −0.53 | 0.20 | COPD | 0 |
| NHC.1442 | NHC | −0.56 | 0.32 | NM | 0 |
| NHC.1438 | NHC | −0.61 | 0.25 | NM | 0 |
| NHC.10038 | NHC | −0.63 | 0.20 | COPD | 0 |
| NHC.1488 | NHC | −0.64 | 0.16 | GI | 0 |
| NHC.10042 | NHC | −0.65 | 0.22 | COPD | 0 |
| NHC.1594 | NHC | −0.66 | 0.17 | GI | 0 |
| NHC.1186 | NHC | −0.66 | 0.36 | NM | 0 |
| NHC.1399 | NHC | −0.66 | 0.29 | GI | 0 |
| NHC.1191 | NHC | −0.68 | 0.27 | NM | 0 |
| NHC.10048 | NHC | −0.69 | 0.30 | COPD | 0 |
| NHC.10061 | NHC | −0.69 | 0.35 | COPD | 0 |
| NHC.10049 | NHC | −0.70 | 0.28 | COPD | 0 |
| NHC.10055 | NHC | −0.70 | 0.25 | COPD | 0 |
| NHC.10023 | NHC | −0.74 | 0.17 | CR | 0 |
| NHC.1242 | NHC | −0.74 | 0.27 | NM | 0 |
| NHC.10003 | NHC | −0.77 | 0.34 | HTN | 0 |
| NHC.10039 | NHC | −0.80 | 0.22 | COPD | 0 |
| NHC.1697 | NHC | −0.84 | 0.14 | GI | 0 |
| NHC.1309 | NHC | −0.86 | 0.25 | NM | 0 |
| NHC.1305 | NHC | −0.92 | 0.19 | GI | 0 |
| NHC.1185 | NHC | −0.93 | 0.21 | NM | 0 |
| NHC.1289 | NHC | −0.94 | 0.28 | NM | 0 |
| NHC.1277 | NHC | −0.94 | 0.27 | NM | 0 |
| NHC.10029 | NHC | −0.95 | 0.21 | COPD | 0 |
| NHC.10053 | NHC | −0.97 | 0.18 | COPD | 0 |
| NHC.1616 | NHC | −1.00 | 0.11 | NM | 0 |
| NHC.10030 | NHC | −1.03 | 0.25 | SARC | 0 |
| NHC.10019 | NHC | −1.07 | 0.10 | NHC | 0 |
| NHC.10035 | NHC | −1.07 | 0.14 | COPD | 0 |
| NHC.10051 | NHC | −1.08 | 0.19 | COPD | 0 |
| NHC.10013 | NHC | −1.08 | 0.28 | COPD | 0 |
| NHC.1251 | NHC | −1.09 | 0.19 | GI | 0 |
| NHC.10008 | NHC | −1.11 | 0.28 | GI | 0 |
| NHC.10018 | NHC | −1.13 | 0.15 | COPD | 0 |
| NHC.10012 | NHC | −1.21 | 0.21 | COPD | 0 |
| NHC.1342 | NHC | −1.22 | 0.21 | GI | 0 |
| NHC.10052 | NHC | −1.25 | 0.25 | COPD | 0 |
| NHC.10041 | NHC | −1.27 | 0.18 | COPD | 0 |
| NHC.10031 | NHC | −1.32 | 0.27 | COPD | 0 |
| NHC.1490 | NHC | −1.34 | 0.15 | NM | 0 |
| NHC.1250 | NHC | −1.37 | 0.26 | NM | 0 |
| NHC.10005 | NHC | −1.40 | 0.13 | CR | 0 |
| NHC.1267 | NHC | −1.43 | 0.12 | NM | 0 |
| NHC.10057 | NHC | −1.52 | 0.27 | COPD | 0 |
| NHC.1450 | NHC | −1.56 | 0.34 | GI | 0 |
| NHC.10001 | NHC | −1.56 | 0.16 | HTN | 0 |
| NHC.10022 | NHC | −1.57 | 0.20 | COPD | 0 |
| NHC.10059 | NHC | −1.65 | 0.15 | COPD | 0 |
| NHC.1328 | NHC | −1.65 | 0.14 | NM | 0 |
| NHC.1314 | NHC | −1.68 | 0.20 | GI | 0 |
| NHC.10050 | NHC | −1.82 | 0.19 | COPD | 0 |
| NHC.10033 | NHC | −1.83 | 0.20 | COPD | 0 |
| NHC.10032 | NHC | −1.89 | 0.15 | COPD | 0 |
| NHC.10056 | NHC | −2.45 | 0.10 | COPD | 0 |

Example 15

Independent Validation Studies on Hold-Out Samples

To address issues of data over-fitting and to test the generality of the classification model before applying it to new samples, the analysis was re-performed, setting aside 20% of the patient and control samples including representatives of each of the subclasses for validation and training on the remaining 80%. 5 separate and non-overlapping holdout sets were subject to this revalidation. The average accuracy over the 5 validation sets was 81% as compared to an average accuracy of 82% for the 5 training sets (data not shown). The similar accuracy of the training and validation sets demonstrated the ability of the algorithm to classify new samples with predicted accuracy. The slightly lower accuracy with the hold-out sets compared to cross validation using all of the data (81% vs. 86%) was a reflection of the smaller number of samples available for training. By contrast the average accuracy of the analysis with permuted sample labels was only 58% across 10 permutation runs. It was concluded that the 29 gene signature of Table V can distinguish patients with either of the two main NSCLC subtypes and any of the four NSCLC tumor stages, from patients with other smoking-related but non-malignant lung diseases.

Example 16

Classification Accuracy for Patient and Control Subclasses Using 29 Genes

The accuracy of the 29 gene classifier was examined for the different types of patients and controls in the data set. Table XII below lists the accuracies for the 29 genes in identifying the various patient and control classes as well as for increasing pathological tumor stages. The individual classification accuracies for AC or LSCC alone were 86% and 98% respectively as compared to 91% for the combined patients. There were half as many LSCC in the dataset, but they were classified with significantly higher accuracy.

Lines 7-12 of Table XII showed an incremental increase in classification accuracy from Stage 1A (83%) to stages 3 and 4 (100%), supporting that the PBMC cancer signature becomes more pronounced with progressive disease. If only the controls with confirmed COPD and no evidence of lung nodules were considered, they classified with an accuracy of 89%, while patients with confirmed benign nodules (regardless of COPD status) had a classification accuracy of 71%. Thus, classification accuracy was influenced by cancer stage,

TABLE XII

Performance of 29 gene classifier on subclasses of patients and controls.

| # | Subclass | Accuracy by Class | Number of Samples |
|---|---|---|---|
| 1 | NSCLC | 91% | 137 |
| 2 | NHC | 80% | 91 |
| 3 | AC | 86% | 85 |
| 4 | LSCC | 98% | 42 |
| 5 | Nodules | 71% | 41 |
| 6 | COPD | 89% | 38 |
| 7 | Stage 1A | 83% | 48 |
| 8 | Stage 1B | 89% | 27 |
| 9 | Stage 1 | 85% | 75 |
| 10 | Stage 2 | 89% | 18 |
| 11 | Stage 3 | 100% | 39 |
| 12 | Stage 4 | 100% | 5 |

Although 29 genes were sufficient to distinguish patient and control classes, many more statistically significant genes were differentially expressed (see Table V). Molecular functions most highly represented included, regulation of gene expression, cell death and cell growth and differentiation. Genes associated with the generation of memory T-cells, T-cell accumulation and mobilization of NK cells were mostly up in cancer, while B-cell receptor signaling pathways were down. Genes associated with activation or chemotaxis of myeloid cells and gluco-corticoid receptor signaling genes were overwhelmingly down in the cancer patients.

The clinical application of the PBMC gene expression signature is clear. Assuming a lung cancer prevalence of 5% for patients with a lung nodule between 0.5 and 3.0 cm, the 29-gene classifier (with a cut-off value of zero) is anticipated to achieve a positive (PPV) and negative predictive value (NPV) of 0.19 and 0.99 respectively, as shown in Table XIII below. These values exceed those established by the EDRN Lung Cancer Biomarker Group that determines if a biomarker is to be considered useful for additional study. These are similar to values for the 80 gene expression panel from bronchial brushings recently described[18]. Importantly, even higher clinical utility could be achieved in many patients by taking advantage of the actual value of the predictive score rather than using a strict positive or negative score cut-off. In the large dataset shown in Table XI above, no subject with an SVM score less than –0.65 had lung cancer and only 5 of 91 non-cancer control patients had an SVM score of >+0.65 were classified as lung cancer. Thus, the actual value of the SVM score is useful for determining which patients require an invasive intervention as opposed to a more conservative approach, such as serial CT imaging.

TABLE XIII

Positive predictive value and negative predictive value for 29-gene NSCLC classifier.

| Study | Sensitivity | Specificity | Prevalence | PPV | NPV |
|---|---|---|---|---|---|
| NSCLC vs. NHC | 0.91 | 0.8 | 1% | 0.044 | 0.999 |
| 29 gene classifier | | | 5% | 0.193 | 0.994 |
| Spira et al., 2007 | 0.8 | 0.84 | 1% | 0.048 | 0.998 |
| 80 gene classifier | | | 5% | 0.208 | 0.988 |
| LCGB | 0.8 | 0.7 | 1% | 0.026 | 0.997 |
| Proposed biomarker | | | 5% | 0.123 | 0.985 |

Example 17

Classification of Patient and Control Samples from an Independent Site

All of the samples used to develop and validate the 29 gene panel were collected at the Hospital of the University of Pennsylvania. To further validate the utility of the classifier we analyzed 27 samples collected at the NYU Lung Cancer Biomarker Center, an Early Detection Research Network (EDRN) Clinical and Epidemiologic Validation Center. The 27 samples included 12 Stage 1 NSCLC (5 of which were never smokers), and 15 smoker and ex-smokers controls, including 6 controls diagnosed by serial CT scans as having non-malignant Ground Glass Opacities (GGO)[21]. No GGO samples were included in our original training set.

Despite the differences in collection sites, sample processing and the different control population, the 27 samples were classified with an overall accuracy of 74% (20 of 27), sensitivity of 67% (8 of 12) and specificity of 80% (12 of 15). The SVM classification is shown in detail in TABLE XIV below.

TABLE XIV

SVM classification scores by NSCLC classifier for NYU validation samples

| ID | Class | Score | Error | Dx |
|---|---|---|---|---|
| NYU.1 | NSCLC | 1.07 | 0.06 | AC |
| NYU.2 | NSCLC | 1.01 | 0.07 | AC |
| NYU.3 | NSCLC | 0.95 | 0.06 | AC |
| NYU.4 | NSCLC | 0.81 | 0.07 | AC |
| NYU.5 | NSCLC | 0.71 | 0.08 | AC |
| NYU.6 | NSCLC | 0.48 | 0.06 | AC |
| NYU.7 | NSCLC | 0.29 | 0.08 | AC |
| NYU.8 | NSCLC | 0.18 | 0.09 | AC |
| NYU.9 | NSCLC | –0.25 | 0.09 | AC |
| NYU.10 | NSCLC | –0.29 | 0.10 | AC |
| NYU.11 | NSCLC | –0.37 | 0.10 | AC |
| NYU.12 | NSCLC | –0.94 | 0.08 | AC |
| NYU.13 | NHC | 1.16 | 0.10 | GGO |
| NYU.14 | NHC | 0.70 | 0.11 | N |
| NYU.15 | NHC | 0.69 | 0.10 | GGO |
| NYU.16 | NHC | –0.12 | 0.08 | N |
| NYU.17 | NHC | –0.13 | 0.09 | GGO |
| NYU.18 | NHC | –0.26 | 0.08 | N |
| NYU.19 | NHC | –0.39 | 0.09 | GGO |
| NYU.20 | NHC | –0.39 | 0.08 | N |
| NYU.21 | NHC | –0.46 | 0.10 | N |
| NYU.22 | NHC | –0.52 | 0.10 | N |
| NYU.23 | NHC | –0.58 | 0.07 | N |
| NYU.24 | NHC | –0.73 | 0.09 | N |
| NYU.25 | NHC | –0.75 | 0.10 | N |
| NYU.26 | NHC | –0.84 | 0.09 | GGO |
| NYU.27 | NHC | –0.94 | 0.08 | GGO |

Dx abbreviations:
AC = adenocarcinoma,
N = normal,
GGO = ground glass opacities

Two of the misclassified patients were never smokers and 2 of the controls were GGOs. The reduced accuracy in the external validation set was most likely due to the differences in the processing of the samples (data not shown).

Example 18

29 Gene Classification of Independent Samples Before and after Tumor Removal

The 29 gene classifier was tested on an independent set of 36 samples from 18 NSCLC patients that included both pre- and post-resection samples. First, as further validation, when using this classifier, fourteen of 18 pre-surgery samples correctly classified as cancer, for a sensitivity of 78%. Second, the SVM scores for 13 of the 14 (92%) showed significant decreases in the classification score after surgical resection. Seven of the post-resection samples had SVM scores that were negative and classified as non-cancer samples in this analysis (data not shown). There was no obvious correlation between the change in the SVM scores and the time of post-resection PBMC collection, although the data set is relatively small Gene expression profiles change in PBMC after tumor removal, as demonstrated below. The analysis shown in FIG. 5 of the pre/post paired samples was carried out to determine whether the 29 gene classifier developed on patients with malignant vs. non-malignant disease would detect a difference in gene expression after the removal of the tumor. Given the observation that this was true for the majority of the samples, the extent of the differences between the sample classes was examined. The sample pairs were directly compared to further assess changes in gene expression that might result from removing the tumor. A significant effect on PBMC gene expression was found; 2060 genes were found to be differentially expressed across the pairs (paired two-tail t-test, p<0.05 with a false discovery rate of 28%).

Figure 6:
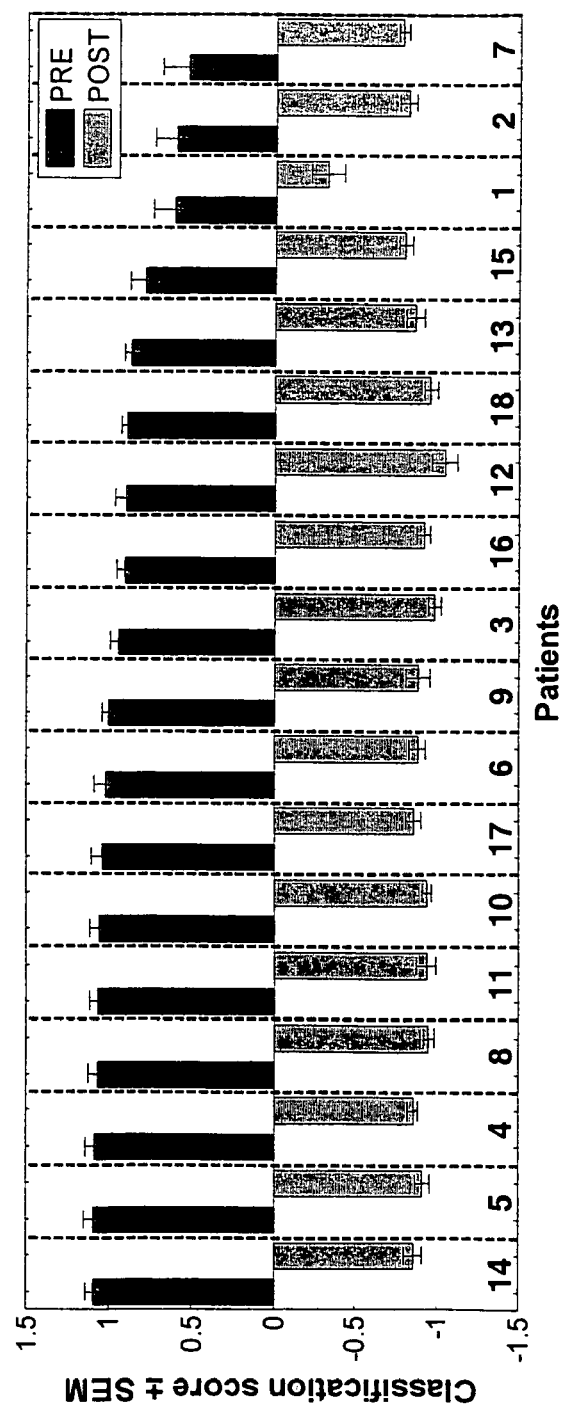
FIG. 6 is a graph showing classification of pre- and post-surgery samples with 4 gene classifier (CYP2R1, MYO5B, DGUOK and DNCL1) trained by SVM-RFE with 10-fold cross-validation.

A separate SVM classifier for the pre- and post-surgery patients was generated and the 50 genes forming that classifier set is reported in Table VI above. One classifier selected from the genes of Table VI was able to perfectly separate the two classes with as few as four genes. The top ranking four genes in this classifier include CYP2R1 (a microsomal vitamin D hydroxylase), MYO5B (mitochondrial 3-oxoacyl-Coenzyme A thiolase), DGUOK (Mitochondrial Deoxyguanosine Kinase), all down-regulated post-surgery and DNCL1 (Dynein, cytoplasmic, light chain 1) which is up-regulated after surgery. Two (CYP2R1 and DGUOK) of the 4 genes were also validated by Quantitative Realtime PCR on 10 sample pairs. The results are indicated in FIG. 6 and Table XV below.

TABLE XV

PRE/POST PBMC surgery expression ratios for 10 patients as determined by Illumina gene expression arrays and QPCR analysis.

| Patient | CYP2R1 Illumina arrays | CYP2R1 PCR | DGUOK Illumina arrays | DGUOK PCR |
|---|---|---|---|---|
| 4 | 1.13 | 1.33 | 1.33 | 1.21 |
| 5 | 1.55 | 1.28 | 1.12 | 1.01 |
| 6 | 1.49 | 1.73 | 1.21 | 1.41 |
| 7 | 1.33 | 1.06 | 1.12 | 1.17 |
| 11 | 1.44 | 1.58 | 1.38 | 1.09 |
| 14 | 1.37 | 1.29 | 1.30 | 1.25 |
| 15 | 1.15 | 2.65 | 1.14 | 2.14 |
| 16 | 1.42 | 0.96 | 1.19 | 0.76 |
| 17 | 1.60 | 1.57 | 1.21 | 1.56 |
| 18 | 1.10 | 1.09 | 1.31 | 1.15 |
| AVERAGE | 1.36 | 1.45 | 1.23 | 1.27 |

Example 19

Gene Expression Signature for Differentiation of Patients with Benign Lung Nodules Since the patients with diagnosis of a benign nodule are the most important control class for differentiation, a separate classifier was developed using only the controls with benign nodules and its accuracy assessed. Using the 41 controls with nodules and a randomly selected group of 54 NSCLC samples, SVM-RFE with cross validation was applied, as described above. The resulting classifier (Table VII, genes 1-24) was 79% accurate, with a specificity of 80% for the nodules and requires as few as 24 genes, 7 of which were included in the 29 gene panel. Table VII lists the rank of the gene "RANK" in NSCLC vs. NHC classifier, the Illumina Spot ID "ID", the Accession No. "Acc. No.", the description of the gene, its symbol, the NSCLC vs. GI.NM p-value "p-value", and the NSCLC/GI.NM fold change "Fold Chg".

VI. REFERENCES

1. Yousef, M., et al., 2007 BMC Bioinformatics, 8: p. 144.
2. Jemal, A., et al., 2006 J Clin 56(2): p. 106-30.
3. Marcus, P. M., et al., 2000 J Natl Cancer Inst, 92(16): p. 1308-16.
4. Palmisano, W. A., et al., 2000 Cancer Res, 60(21): p. 5954-8.
5. Patz, E. F., Jr., et al 2000 N Engl J Med, 343(22): p. 1627-33.
6. Hirsch, F. R., et al., 2001 Clin Cancer Res, 7(1): p. 5-22.
7. Burczynski M E, et al., 2005 Clin Cancer Res., 11(1181-9).
8. Burczynski, M. E., et al., 2005 Curr Mol Med, 5(1): p. 83-102.
9. Chang, H. Y., et al., 2002 Proc Natl Acad Sci USA, 99(20): p. 12877-82.
10. Borczuk, A. C., et al., 2003 Am J Pathol, 163(5): p. 1949-60.
11. Gao, C., et al., 2005 Nitric Oxide, 12(2): p. 121-6.
12. Mulshine, J. L., 2005 Oncology (Williston Park), 19(13): p. 1724-30; disc. 30-1.
13. Haiman, C. A., et al., 2006 N Engl J Med, 354(4): p. 333-42.
14. Diederich, S. and D. Wormanns, 2004 Lung Cancer 45 Suppl 2: p. S13-9.
15. Jett, J. R., 2005 Clin Cancer Res, 11(13 Pt 2): p. 4988s-4992s.
16. Deppermann, K. M., 2004 Lung Cancer, 45 Suppl 2: p. S39-42.
17. MacMahon, H., et al., 2005 Radiology, 237(2): p. 395-400.
18. Berger, M., et al, 2003 AJR Am J Roentgenol, 2003. 181(2): p. 359-65.
19. Mulshine, J. L., 2005 Clin Cancer Res, 11(13 Pt 2): p. 4993s-4998s.
20. Bhattacharjee, A., et al., 2001 Proc. Natl. Acad. Sci, USA, 98:13790-13795
21. Burczynski, M. E. and A. J. Dorner, 2006 Pharmacogenomics, 7(2): p. 187-202.
22. Chaussabel, D., et al., 2005 Ann NY Acad Sci, 2005. 1062: p. 146-54.
23. Burczynski M E, et al., 2005 J. Mol Diagn., 2005. 8(51-61).
24. Deng M C, et al., 2006 Am J. Transplant., 6: p. 150-160.
25. Achiron, A., et al., 2005 Breast Cancer Res Treat, 89(3): p. 265-70.
26. Achiron, A. and M. Gurevich, 2006 Autoimmun Rev, 5(8): p. 517-22.
27. Goronzy, J. J., et al., 2004 Arthritis Rheum, 2004. 50(1): p. 43-54.
28. Bull T M, et al, 2006 Am J Respir Crit Care Med., 4(170): p. 911-919.
29. Achiron, A., et al., 2007 Ann NY Acad Sci, 1107: p. 155-67.

30. Sharp, F. R., et al., 2006 Arch Neurol, 63(11): p. 1529-1536.
31. Forrest, M. S., et al., 2005 Environ Health Perspect, 113(6): p. 801-7.
32. Theodoro, T. R., et al., 2007 Neoplasia, 9(6): p. 504-10.
33. Karimi, K., et al., 2006 Respir Res, 7: p. 66.
34. van Leeuwen, D. M., et al., 2007 Carcinogenesis, 28(3): p. 691-7.
35. Oudijk, E. J., et al., 2005 Thorax, 60(7): p. 538-44.
36. Lampe, J. W., et al., 2004 Cancer Epidemiol Biomarkers Prev, 13(3): p. 445-53.
37. Spira, A., et al., 2004 Proc Natl Acad Sci USA, 101(27): p. 10143-8.
38. Russo, A. L., et al., 2005 Clin Cancer Res, 11(7): p. 2466-70.
39. Kari, L., et al., 2003 J Exp Med, 197(11): p. 1477-88.
40. Talmadge, J. E., et al., 1996 Bone Marrow Transplant, 17(1): p. 101-9.
41. Redente, E. F., et al., 2007 Am J Pathol, 170(2): p. 693-708.
42. Twine, N., et al., 2003 Cancer Res., 6: p. 6069-75.
43. Sharma, P., et al., 2005 Breast Cancer Res, 7: p. 634-44.
44. DePrimo, S. E., et al., 2003 BMC Cancer, 3: p. http://www.biomedcentral.com/1471-2407/3/3.
45. Eady, J. J., et al., 2005 Physiol Genomics, 22(3): p. 402-11.
46. Whitney, A. R., et al., 2003 Proc Natl Acad Sci USA, 100(4): p. 1896-901.
47. Loboda, A., et al., 2003 Proc. Eur. Conf. on Computational Biology, GE-19, p. p 383-84.
48. Guyon, I., et al., 2002 Machine Learning, 46(1-3): p. 389-422.
49. Critchley-Thorne, R. J., et al., 2007 PLoS Med, 4(5): p. e176.
50. Vachani, A., et al., 2007 Clin. Canc. Res., 13(10): p. 2905-2915.
51. Spira, A., et al., 2007 Nat Med, 13(3): p. 361-6.
52. Mulchedee, S., et al., 2003 J Comput Biol, 10(2): p. 119-42.
53. Wang, J., et al., 2007 Bioinformatics, 23(15): p. 2024-7.
54. Vapnik, V., 1999., The Nature of Statistical Learning Theory. Springer-Verlag, 1999. ISBN 0-387-98780-0.
55. Nebozhyn, M., et al., 2006 Blood, 107(8): p. 3189-96.
56. Marron, J. and M. Todd (2003) Distance Weighted Discrimination School of Operations Research and Industrial Engineering, Cornell University
57. Virok, D., et al., 2003 J Infect Dis, 188(9): p. 1310-21.
58. Pepe, M. S., et al., 2003 Biometrics, 59(1): p. 133-42.
59. DeLong, E. R., et al 1988 Biometrics, 44(3): p. 837-45.
60. Harrell, F. E., Jr., et al., WHO/ARI Young Infant Multicentre Study Group. Stat Med, 1998. 17(8): p. 909-44.
61. Benito, M., et al., 2004 Bioinformatics, 20(1):105-114
62. Chung, G T., et al., 1995 Oncogene, 11:2591-2598
63. Hirano, T., et al., 1994 Am J. Pathol., 144:296-302
64. Kishimoto, Y., et al., J Natl Cancer Inst, 1995 87:1224-1229
65. Tibshirani, R., et al., Proc Natl Acad Sci USA, 2002 99:6567-6572
66. Tonon, G., et al., Proc Natl Acad Sci, 2005 102:9625-9630
67. MacQueen, J. Proceedings of the Fifth Berkeley Symposium on Mathematical Statistics and Probability. University of California Press; 1967. Some methods for classification and analysis of multivariate observations; pp. 281-297.
68. Talbot, S G, et al. Cancer Res. 2005; 65:3063-3071.
69. Ausubel et al., Current Protocols in Molecular Biology, Wiley Interscience Publishers, (1995).
70. Sambrook et al., Molecular Cloning: A Laboratory Manual, New York: Cold Spring Harbor Press, 1989
71. B. Lewin. Genes IV Cell Press, Cambridge Mass. 1990
72. Singleton et al., Dictionary of Microbiology and Molecular Biology 2nd ed., J. Wiley & Sons (New York, N.Y. 1994)
73. March, Advanced Organic Chemistry Reactions, Mechanisms and Structure 4th ed., John Wiley & Sons (New York, N.Y. 1992)
74. Parker & Barnes, 1999 Methods in Molecular Biology 106:247-283
75. Hod, 1992 Biotechniques 13:852 854
76. Weis et al., 1992 Trends in Genetics 8:263 264
77. Ausubel et al., Current Protocols of Molecular Biology, John Wiley and Sons (1997)
78. Rupp and Locker, 1987 Lab Invest. 56:A67
79. De Andres et al., 1995 BioTechniques 18:42044
80. T. E. Godfrey et al. 2000 J. Molec. Diagnostics 2: 84 91
81. K. Specht et al., 2001 Am. J. Pathol. 158: 419-29
82. Ding and Cantor, 2003 Proc. Natl. Acad. Sci. USA 100: 3059-3064
83. U.S. Pat. No. 7,081,340
84. International Patent Application Publication No WO 2004/105573, published Dec. 9, 2004
85. Krawetz S, Misener S (eds) Bioinformatics Methods and Protocols: Methods in Molecular Biology. Humana Press, Totowa, N.J., pp 365-386)
86. Dieffenbach, C. W. et al., "General Concepts for PCR Primer Design" in: PCR Primer, A Laboratory Manual, Cold Spring Harbor Laboratory Press, New York, 1995, pp. 133-155
87. Innis and Gelfand, "Optimization of PCRs" in: PCR Protocols, A Guide to Methods and Applications, CRC Press, London, 1994, pp. 5-11
88. Plasterer, T. N. 1997 Methods Mol. Biol. 70:520 527
89. Golub T R, et al 1999 Science. 286:531-537
90. ACS. Cancer Facts and Figures 2007. Atlanta: American Cancer Society; 2008.
91. Amos C I, et al. 2008 Nat Genet, 40:616-22.
92. Kang J U, et al, 2008 Cancer Genet Cytogenet, 184:31-7.
93. Thorgeirsson T E, et al., 2008 Nature, 452:638-42.
94. Henschke C I, et al, 2006 N Engl J Med, 355:1763-71.
95. Bach PB, 2007 JAMA, 297:953-61.
96. Ikeda K, et al, 2007 Chest, 132:984-90.
97. Machida E O, et al. 2006 Cancer Res, 66:6210-8.
98. Patz E F, Jr. et al, 2007 J Clin Oncol, 25:5578-83.
99. Yanagisawa K, et al. 2003 Lancet, 362:433-9.
100. Brichory F M, et al. 2001 Proc Natl Acad Sci USA, 98:9824-9.
101. Pontes E R, et al. 2006 Prostate, 66:1463-73.
102. Belinsky S A, et al. 2006 Cancer Res, 66:3338-44.
103. Ohta Y, et al. 2006 Ann Thorac Surg, 81:1194-7.
104. Osman I, et al. 2006 Clin Cancer Res, 12:3374-80.
105. Subramanian J, Govindan R. 2007 J Clin Oncol, 25:561-70.
106. Sun S, et al, 2007 Nat Rev Cancer, 7:778-90.
107. Hung RJ, et al. 2008 Nature, 452:633-7.
108. Mashima T, Tsuruo T. 2005 Drug Resist Updat, 8:339-43.
109. Ozoren N, El-Deiry W S. 2003 Semin Cancer Biol, 13:135-47.
110. Held et al., Genome Research 6:986 994 (1996).

Each and every patent, patent application, and publication, including the priority application and publicly available gene sequence cited throughout the disclosure is expressly incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

The invention claimed is:

1. A composition for evaluating the existence or progression of a lung cancer in a mammalian subject, said composition consisting essentially of polynucleotides or oligonucleotides, wherein each polynucleotide or oligonucleotide hybridizes to a gene, gene fragment, or gene transcript of a different marker in a mammalian blood sample, each marker being one of the markers in the combination consisting of:
   (a) hepatitis B virus x associated protein (HBXAP or RSF1)
   (b) dual-specificity tyrosine-(Y)-phosphorylation regulated kinase 2 (DYRK2)
   (c) YY1 transcription factor (YY1)
   (d) chromosome 19 open reading frame 12, transcript variant 1 (C19orf12);
   (e) thioesterase superfamily member 2 (THEM2)
   (f) triple functional domain (PTPRF interacting) (TRIO)
   (g) myeloid-associated differentiation marker, transcript variant 4 (MYADM)
   (h) BAI1-associated protein 2 (BAIAP2)
   (i) leucine zipper domain protein (FLJ22386 or ROGDI)
   (j) DnaJ (Hsp40) homolog, subfamily B, member 14 (DNAJB14)
   (k) brain and reproductive organ-expressed TNFRSF1A modulator (BRE),
   (l) transmembrane protein 41A (TMEM41A)
   (m) chromosome 9 open reading frame 64 (C9orf64)
   (n) chromosome 20 open reading frame 55, transcript variant 1 (C20orf55 or FAM110A),
   (o) pecanex-like 2 PCNXL2
   (p) RE1-silencing transcription factor (REST)
   (q) HSPC142 protein (HSPC142 or C19orf62)
   (r) hypothetical protein BC015148 (LOC93081 or C13orf27)
   (s) activating signal cointegrator 1 complex subunit 3 (ASCC3)
   (t) solute carrier family 1, member 5 (SLC1A5)
   (u) protein tyrosine phosphatase-like A domain containing 1 (PTPLAD1)
   (v) MRE11meiotic recombination 11 homolog A (MRE11A)
   (w) hypothetical protein or GTP-binding protein 10 (DKFZP686A10121 or GTPBP10)
   (y) Soares fetal liver spleen 1NFLS cDNA clone IMAGp998K18127
   (z) serpin peptidase inhibitor, clade I (pancpin), member 2 (SERPINI2),
   (aa) cDNA FLJ44370 fis, clone TRACH3008902 or CAMP responsive element binding protein 1 (CREB1)
   (bb) coiled-coil domain containing 53 (CCDC53)
   (cc) ubiquitin specific peptidase 48 (USP48); and
   (dd) zinc finger and SCAN domain containing 2, transcript variant 3 (ZSCAN2).

2. The composition according to claim 1, which is a reagent comprising a substrate upon which said polynucleotides or oligonucleotides are immobilized.

3. The composition according to claim 1, comprising a microarray, a microfluidics card, a chip or a chamber.

4. The composition according to claim 1, which is a kit containing said polynucleotides or oligonucleotides.

5. The composition according to claim 4, wherein said polynucleotides or oligonucleotides are each part of a primer-probe set, and said kit comprises both primer and probe, wherein each said primer-probe set amplifies a different gene or gene fragment.

6. The composition according to claim 1, wherein one or more polynucleotide or oligonucleotide is associated with a detectable label.

7. The composition according to claim 1, wherein the lung cancer is a non-small cell lung cancer of stage I or stage II.

* * * * *